US008785655B2

(12) United States Patent
Gathergood et al.

(10) Patent No.: US 8,785,655 B2
(45) Date of Patent: Jul. 22, 2014

(54) IONIC LIQUID SOLVENTS

(75) Inventors: Nicholas Gathergood, Ashbourne (IE); Bruce Pegot, Limours (FR); Ian Beadham, Southampton (GB); Monika Gurbisz, Dublin (IE); Mukund D. Ghavre, Dublin (IE); Saibh Morrissey, Saint Germain en Laye (FR)

(73) Assignee: Dublin City University, Dublin (IE)

( * ) Notice: Subject to any disclaimer, the term of this patent is extended or adjusted under 35 U.S.C. 154(b) by 0 days.

(21) Appl. No.: 13/203,133

(22) PCT Filed: Feb. 24, 2010

(86) PCT No.: PCT/EP2010/052345
§ 371 (c)(1),
(2), (4) Date: Oct. 19, 2011

(87) PCT Pub. No.: WO2010/097412
PCT Pub. Date: Sep. 2, 2010

(65) Prior Publication Data
US 2012/0071661 A1 Mar. 22, 2012

(30) Foreign Application Priority Data
Feb. 25, 2009 (EP) ..................................... 09002653

(51) Int. Cl.
C07D 233/54 (2006.01)
(52) U.S. Cl.
USPC ...................................................... 548/341.5
(58) Field of Classification Search
USPC ...................................................... 548/341.5
See application file for complete search history.

(56) References Cited

U.S. PATENT DOCUMENTS

| 5,554,620 A | 9/1996 | DeHaven-Hudkins et al. |
| 2006/0014955 A1* | 1/2006 | Armstrong et al. ............... 546/2 |

OTHER PUBLICATIONS

Siyutkin et al. Tetrahedron Letters 49 (2008) 1212-1216.*
Siyutkin et al. Tetrahedron 65 (2009) 1366-1372.*
Bao et al., "Synthesis of Chiral Ionic Liquids from Natural Amino Acids," Journal of Organic Chemistry, 2003, vol. 68, No. 2, pp. 591-593.
Kakehi et al., "Preparation of New Nitrogen-Bridged Heterocycles. Synthesis and Some Reactions of 2, 3-Dihydroindolizin-2-one Derivatives," Journal of Organic Chemistry, 1980, vol. 45, No. 25, pp. 5100-5104.
Katritzky et al., "Isomers and Aza-Analogues of Indoxyl Containing Nitrogen at a Ring-Fusion Position: Coupling Reactions with Electrophiles and Attempted Oxidations," Journal of Heterocyclic Chemistry, vol. 23, No. 5, Sep. 1986, pp. 1315-1325.
Katritzky et al., "Collisionally Activated Dissociation of N-Alkylpyridinium Cations to Pyridinium Cation and Olefins in the Gas Phase," Journal of the American Chemical Society, 1990, vol. 112, No. 7, pp. 2479-2484.
Li et al., "Synthesis of Multicarboxylic Acid Appended Imidazolium Ionic Liquids and Their Application in Palladium-Catalyzed Selective Oxidation of Styrene," New Journal of Chemistry, 2007, vol. 31, No. 12, pp. 2088-2094.
Mani et al., "Stereoselective Synthesis of Z-α-Aryl-α,β-unsaturated Esters," Journal of Organic Chemistry, vol. 71, No. 13, 2006, pp. 5039-5042.
Matos et al., "Synthesis of New Chiral Ionic Liquids Based on (−)-Menthol and (−)-Borneol," Tetrahedron Letters, 2008, vol. 49, No. 10, pp. 1652-1655.
Nguyen et al., "Aminopentadiene Imines for Zincke Salts of 3-Alkylpyridnes. Application to a Synthesis of Pyridinium Salts from Amino Acids," Journal of Organic Chemistry, vol. 72, No. 15, 2007, pp. 5916-5919.
Takeda et al., "A New Method for the Preparation of α-keto Carboxylic Esters by the Photo-Oxidation of 1-(1-ethoxycarbonylalkyl) Pyridinium Iodides," Chemistry Letters, 1976, pp. 347-348.
Tomilov et al., "Cascade Reactions of Nitrogen- and Phosphorus-Containing Ylides with Methyl Diazoacetate and in situ Generated Diazocyclopropane," Russian Chemical Bulletin, vol. 55, No. 1, 2006, pp. 112-117.
International Search Report for PCT/EP2010/052345 mailed Jul. 14, 2010 (4 pages).
Written Opinion for PCT/EP2010/052345 mailed Jul. 14, 2010 (8 pages).
Benjamin List, "Proline-Catalyzed Asymmetric Reactions," Tetrahedron, vol. 58, 2002, pp. 5573-5590.

* cited by examiner

*Primary Examiner* — Nizal Chandrakumar
(74) *Attorney, Agent, or Firm* — Goodwin Procter LLP

(57) ABSTRACT

A chiral ionic compound comprising an alkyl substituted imidazolium or pyridinium cationic core having an alkyl ester side chain (-alkyl-C(O)O—) directly linked to the core and an associated counter anion, characterized in that the —O— atom of the ester side chain is linked to an alpha, a beta or a gamma hydroxycarboxylic acid functionality via the alpha, beta or gamma hydroxy of the acid functionality and the hydroxycarboxylic acid functionality has at least one asymmetric carbon, or characterized in that an —N═ atom of the alkyl substituted imidazolium or pyridinium cationic core is substituted with an alpha, a beta or a gamma hydroxy group of a alpha, a beta or a gamma hydroxycarboxylic acid functionality and the hydroxycarboxylic acid functionality has at least one asymmetric carbon. The chiral ionic liquids (CILs) may be used as novel solvents, in particular for organic synthesis. The CILs have the potential to induce asymmetry into substrates or catalysts in a variety of organic transformations. A number of the compounds have low antimicrobial and low antifungal toxicities and are also biodegradable CILs.

7 Claims, 11 Drawing Sheets

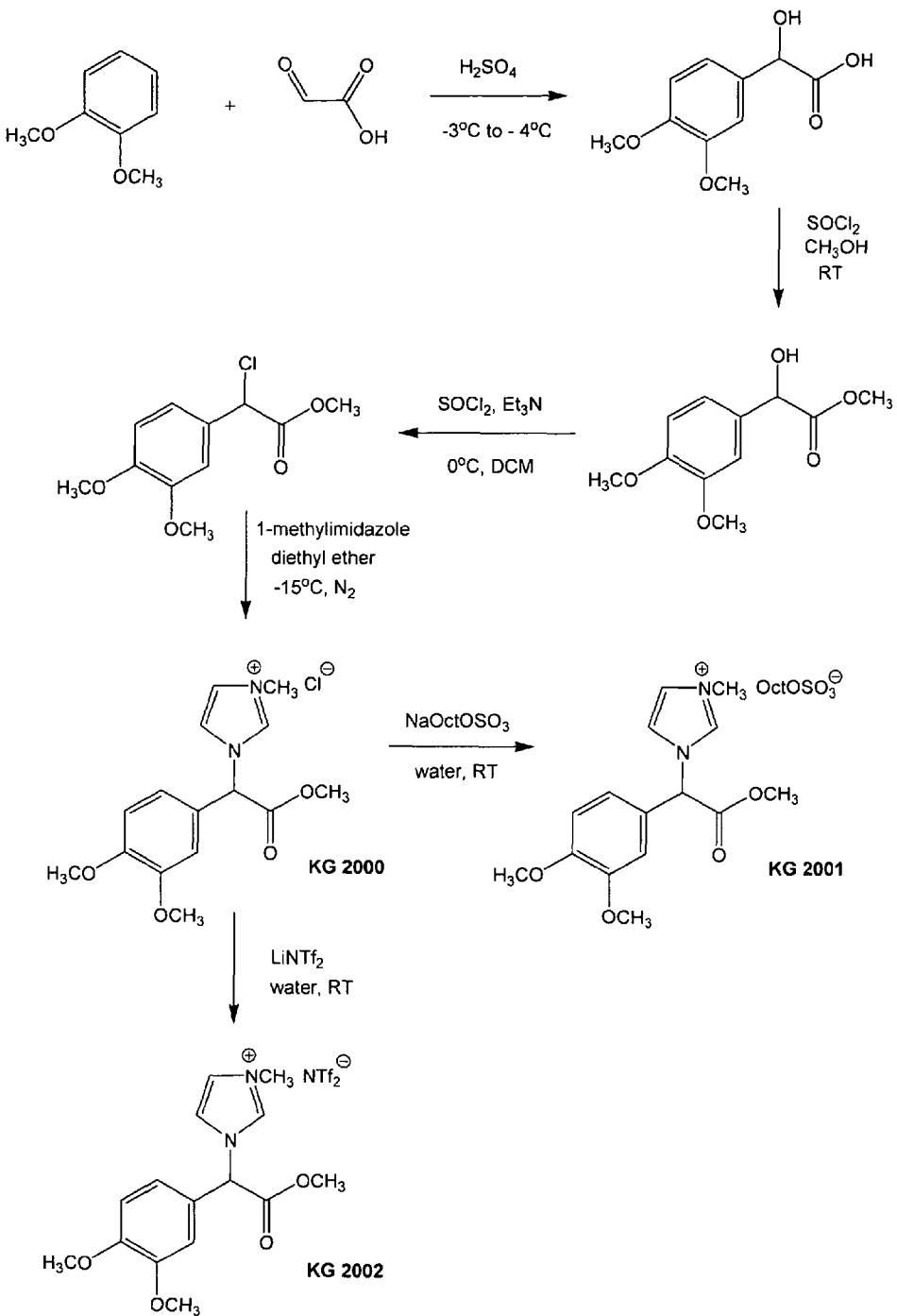
Figure 9: Synthetic route to KG 2000-2002

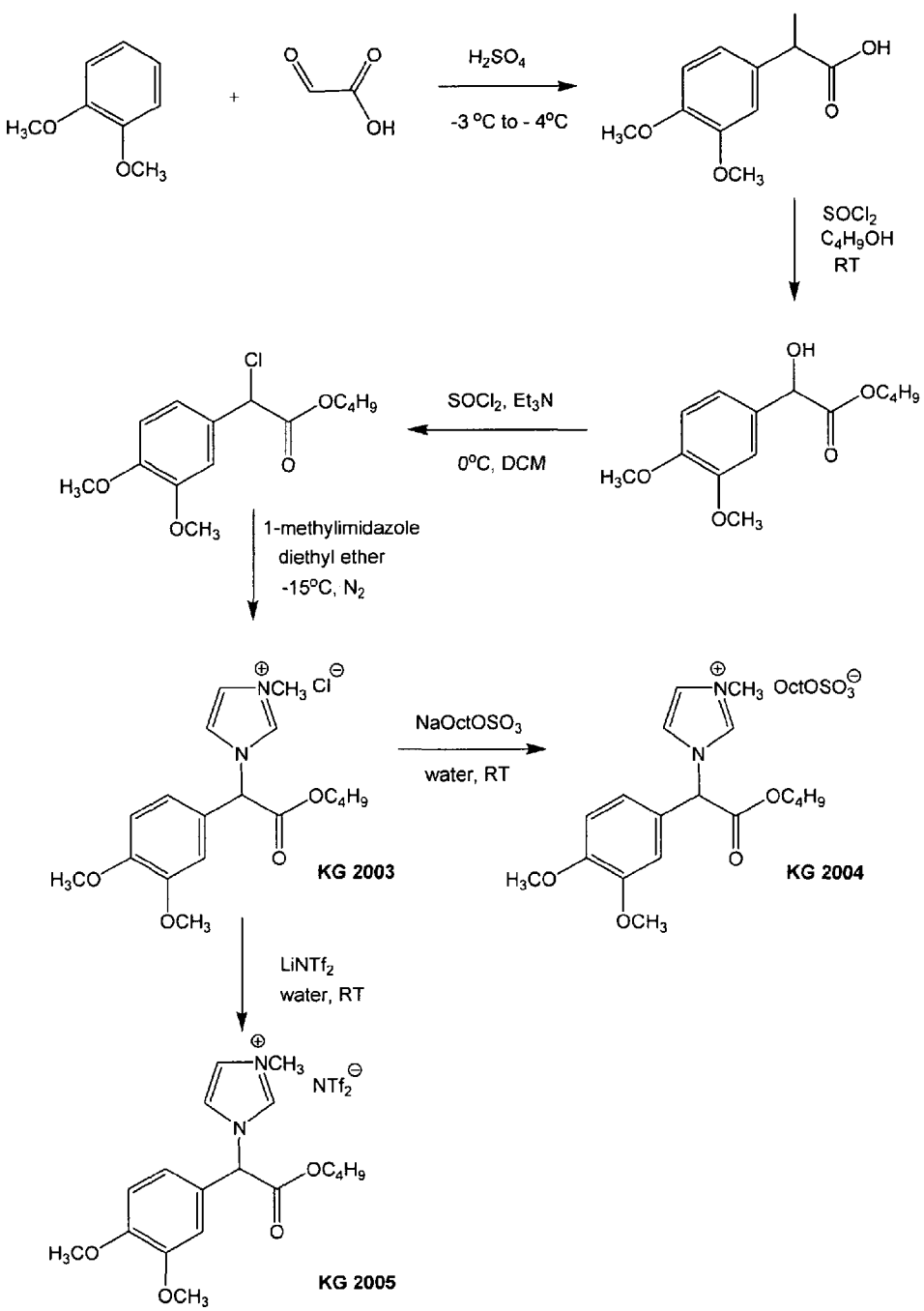
Figure 10: Synthetic route to KG 2003-2005

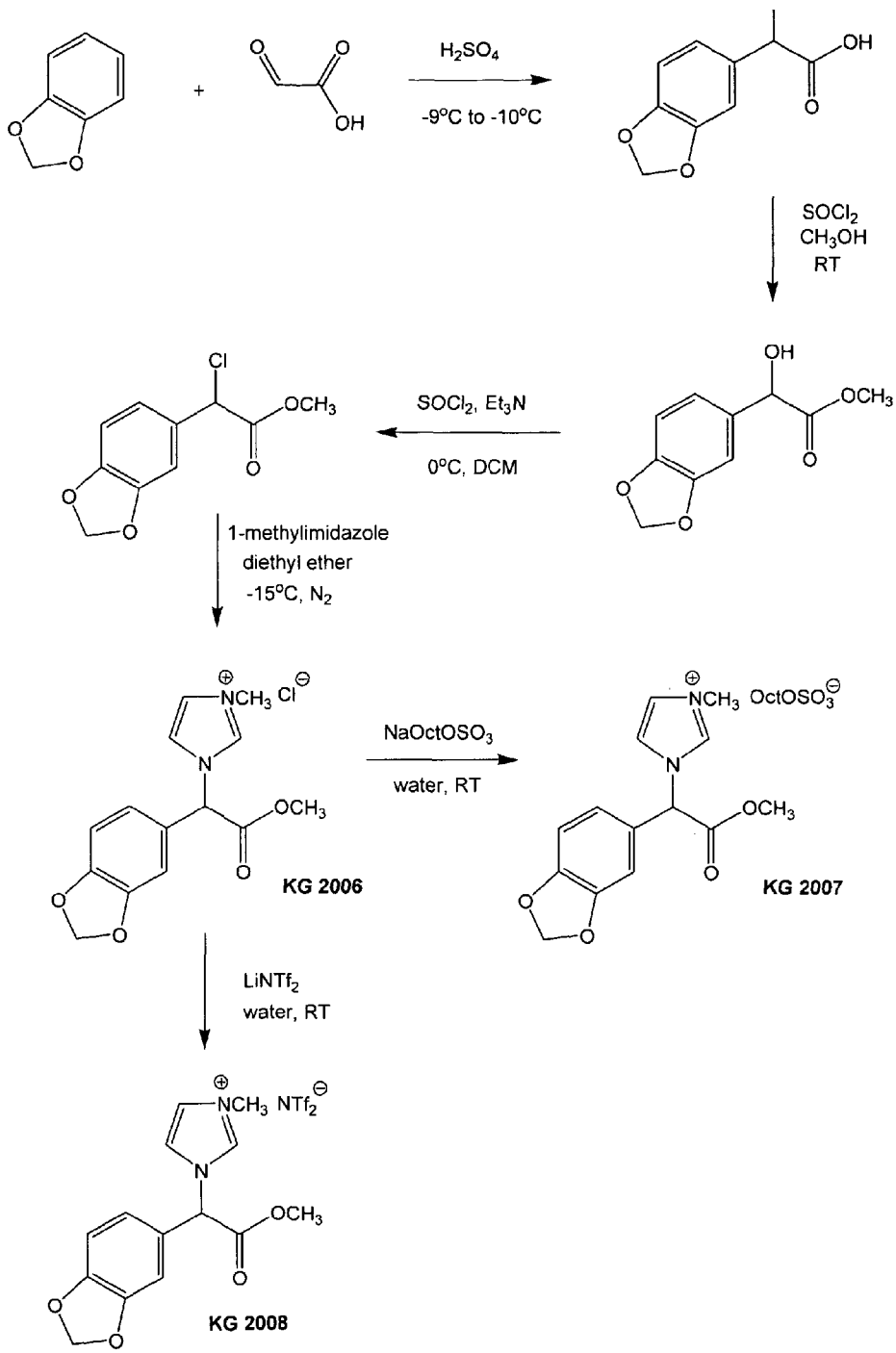
Figure 11: Synthetic Route to KG 2006-2008

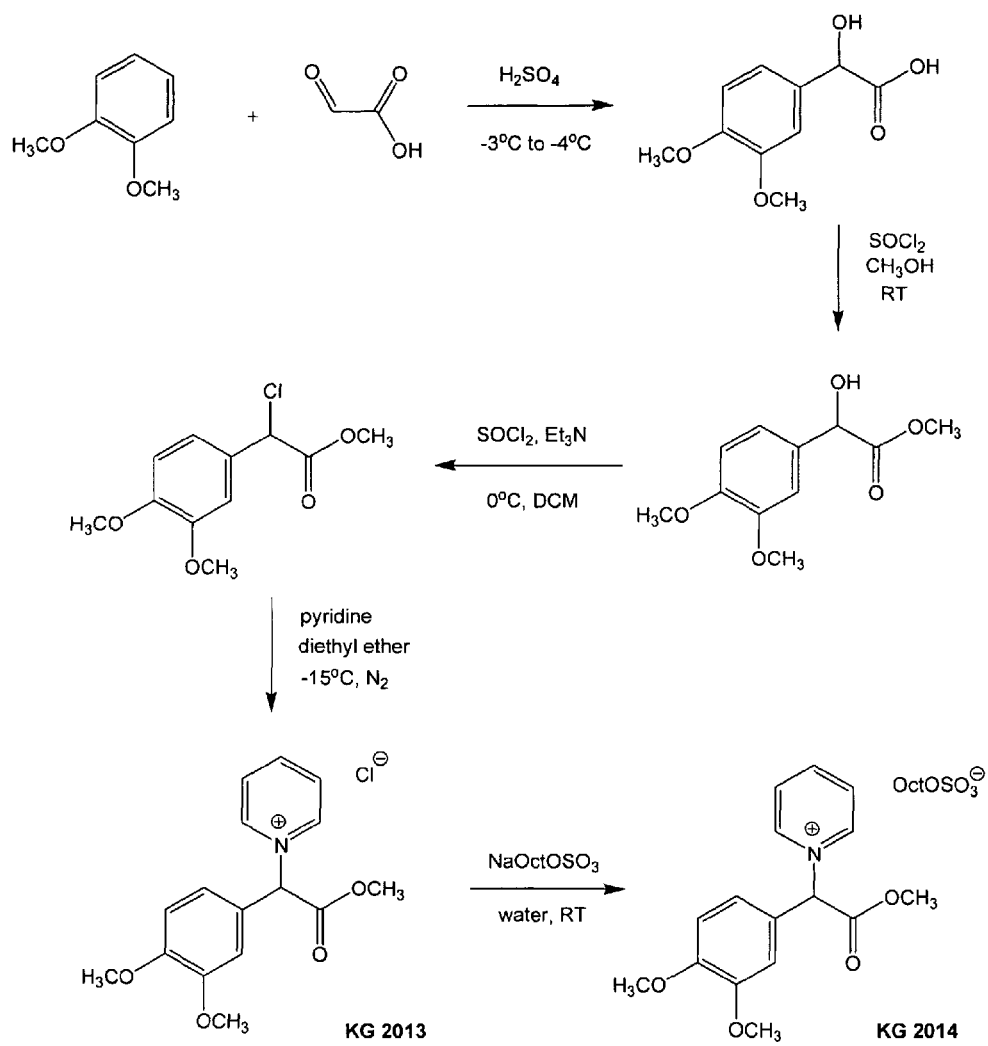
Figure 12: Synthetic route to KG2013-2014

IONIC LIQUID SOLVENTS

RELATED APPLICATIONS

This application is a national stage filing under 35 U.S.C. §371 of PCT/EP2010/052345, filed Feb. 24, 2010, which claims priority to EP09002653.5, filed Feb. 25, 2009, all of which are hereby incorporated by reference.

FIELD OF THE INVENTION

The field of the invention relates to chiral ionic liquids (CILs) as novel solvents. In particular the invention relates to CILs for organic synthesis. More particularly, the invention relates to CILs which have the potential to induce asymmetry into substrates or catalysts in a variety of organic transformations. In particular, the invention relates to biodegradable CILs suitable for these applications.

BACKGROUND TO THE INVENTION

Ionic liquids (ILs) have been used as alternative solvents for a wide range of chemical processes. Over the past decade, while the "greenness" of ILs has been debated, the emergence of industrial processes which make use of ILs to improve their environmental profiles (West) continues to fuel the explosion in research focused on ILs. ILs are of industrial value in the "green" sense, as they possess favourable properties including very low volatility and facile separation of products in suitable cases. This means that ILs have very low vapour pressure and produce virtually no hazardous vapours when compared with traditional volatile solvents. ILs are also attractive as their properties may be tailored or fine-tuned to meet various needs, and ILs now have applications as solvents, chiral coordinating solvents and directing catalysts. ILs now also find uses in applications such as electrochemistry, for example, in wet cell batteries, and also in photochemistry and organic synthesis, as both solvents and as catalysts.

ILs based on aromatic heterocyclic cations, such as imidazolium and pyridinium cation-based ILs are particularly popular due to their ease of modification, low charge density about the aromatic ring and cation stability under acidic conditions. The low aromatic charge density, in particular, means it is easy to synthesize low melting salts (low melting point being a fundamental property of ILs). Unfortunately, traditional ILs based on N-alkylimidazolium and N-alkylpyridinium cores do not lend themselves to biodegradability. In fact, it is well known that dialkyl substituted imidazoles and unsubstituted N-alkylpyridinium rings have limited biodegradability. Biodegradability can be improved with fuctionalisation of the core sidechain(s). In particular, introduction of ester functionality into the IL is known to improve the overall biodegradability.

In 2002, Gathergood and Scammells designed environmentally friendly biodegradable achiral ILs, containing sidechains which act as potential sites of enzymatic hydrolysis. Subsequent studies by Gathergood, directed towards the development of biodegradable, low toxicity solvents that have performance advantages over established solvent media indicated that the presence of an ester linkage in the side chain of the IL cation promoted biodegradation. The IL counterion was also a significant factor, with octylsulfate examples proving readily biodegradable. The Gathergood group recently reported that key features which improve biodegradation and reduce antimicrobial toxicity were also required for improved catalyst performance in the selective hydrogenation of phenoxyocta-2,7-diene. Further investigations by Gathergood into changes in conversion and selectivity in the hydrogenation reactions of cinnamaldehydes and benzyl cinnamate using novel biodegradable and/or low toxicity ILs and recycling of the catalyst/IL media resulted in a communication being published in the journal Green Chemistry (Morrissey et al).

International Patent Application No. PCT/EP2008/060978 describes ionic liquid (IL) solvents for chemical synthesis based on an N-alkylimidazolium cation core which have enhanced biodegradability and reduced toxicity relative to existing imidazolium bases ILs such as 1-butyl-3-methylimidazolium (bmim) salts, many of which produce a score of over 60% biodegradability over 28 days in the Sturm Test, the Closed Bottle Test (OECD 301D) or the $CO_2$ Headspace Test (ISO 14593).

Several groups have approached the problem of increasing biodegradability by developing biorenewable ILs based on cheap, readily available molecules from biological molecules that can be sourced from nature and recycled in known biochemical pathways (e.g. Han's choline cations combined with proline carboxylate anion). While these biorenewables are intended to take the place of synthetic quaternary nitrogen cations such as the alkylammonium, dialkylimidazolium and pyridinium components often found in previous generation ILs, it is sometimes the case that a biorenewable molecule, such as choline (derived from lipids and important as an acetate in neurotransmission) is more cheaply available via a synthetic process (choline is prepared commercially from ethylene oxide and trimethylamine via the Davy Process). Research has led to new ILs where cations are derived from alpha-amino acids and alpha-amino acid ester salts. Since amino acids are essentially a 'food source', they can be taken up by bacteria, fungi etc., into the usual biochemical pathways where they are degraded. These ILs are particularly advantageous compounds, since stereocentres have been retained in the final IL product (Chen et al).

However robust, imidazolium-based ILs, which are stable to a wide range of chemical environments (with notable exceptions) and can be accessed by short, simple synthetic routes, still dominate the field.

The special characteristic that chiral ionic liquids (CILs) possess of being tunable solvents, in which solvent interactions such as polarity, hydrophobicity, and π-π stacking interactions can be tailor-made to an application means that CILs are attracting considerable interest as chiral solvents (Baudequin et al) with many possible applications. Thus, chiral ionic liquids (CILs) are attracting much interest. Solvent chirality is achievable with complex solvents such as ILs. Chirality may be found in either or both of the IL cation and anion.

Although chiral solvents have been known for many years, their major application has been in NMR detection of enantiomeric excesses in chiral compounds. Since Seebach's landmark discovery of modest asymmetric with a chiral solvent in 1975, only a few examples of asymmetric induction using chiral solvents have appeared. Excessive cost, a paucity of applications and modest performance have limited their usefulness. In 2007, Hüttenhain achieved an optimum enantiomeric excess of only 59% in the reduction of acetophenone to 1-phenylethanol at −78° C. using $BH_3$ together with $ZnCl_2$ and (S)-methyl lactate as the solvent, together with a THF co-solvent.

Earle et al reported a first chiral IL solvent possessing chirality in the anion, comprising [bmim][lactate] (bmim=butyl methyl imidazolium), having a chiral anion of (S)-configuration and its use in reaction of dienes and dienophiles. However the products of the reaction were not asymmetric. The [bmim][lactate] ionic liquid was synthesised by the reaction of sodium (S)-2-hydroxypropionate and [bmim]Cl in acetone. The resultant precipitate of sodium chloride was filtered off and the acetone evaporated.

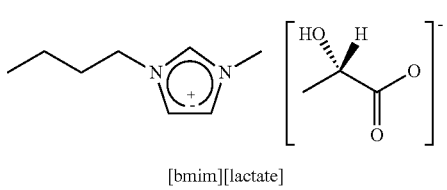

[bmim][lactate]

Chinese Patent Application Publication No. 1 749 249 describes a chiral ionic liquid for use as a chiral catalyst and a chiral solvent, the ionic liquid comprising a cation and a chiral lactate anion.

N-alkylated methyl ephedrine has been used as a chiral cation for ILs in a Baylis-Hillman reaction and chirality was induced in the product. It was proposed that asymmetric induction resulted from the hydroxyl group of methyl ephedrine which could assemble the reagents into a highly ordered transition-state, favouring the desired configuration (Pegot et al).

United States Patent Publication No. US 2005/0065020 describes ionic liquids which have a secondary hydroxyl group and an atom efficient method for the preparation of these ionic liquids by opening an epoxide with an alkylimidazole in the presence of acid. This procedure leads directly to chiral ILs, where chirality is conferred on the cation. Preferably the ILs contain an N-(2-hydroxyalkyl) substituent to provide compounds of general formula (I*), wherein X represents an anion:

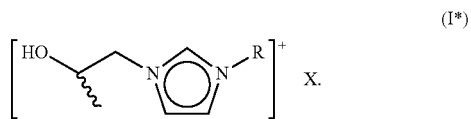

Howarth et al, described [N,N-di(2'S-2'-methylbutane) imidazolium bromide]. This imidazolium ion has two chiral side chains and was used in a catalytic Diels-Alder reaction. The products were produced in minimal enantiomeric excess only. Furthermore, this chiral IL is likely to be expensive to make in an optically enhanced form, since the synthesis requires an optically enhanced bromide compound or alternative alkylating agent in the synthesis.

United States Patent Publication No. US 2003/0149264 describes chiral ionic liquids of the general formula: [A]$^{n+}$ [Y]$^{n-}$, whereby n=1 or 2 and the anion is an anion of an organic or inorganic proton acid and the cation is an optically active organic ammonium cation with up to 50 carbon atoms and at least one chiral centre and at least one functional group, whereby the functional group can produce a coordination by forming hydrogen bridges or providing free electron pairs and at least one chiral centre has a distance of up to 5 atomic bonds from the functional group. The ILs described herein may be used to separate racemates into individual enantiomers, as solvents for asymmetric inorganic and organic synthesis and also as solvents for asymmetric catalysis in organic and inorganic reactions. Typically the ILs find use as solvents for Diels-Alder reactions, benzoin reactions and asymmetric catalysis, in particular hydration and hydrovinylation.

More recently, tetra-n-hexyl-dimethylguanidinium (R)-mandelate, a chiral ionic liquid in which a mandelate anion is providing chirality, has been used as a solvent for asymmetric rhodium(II) carbenoid insertion by Alfonso.

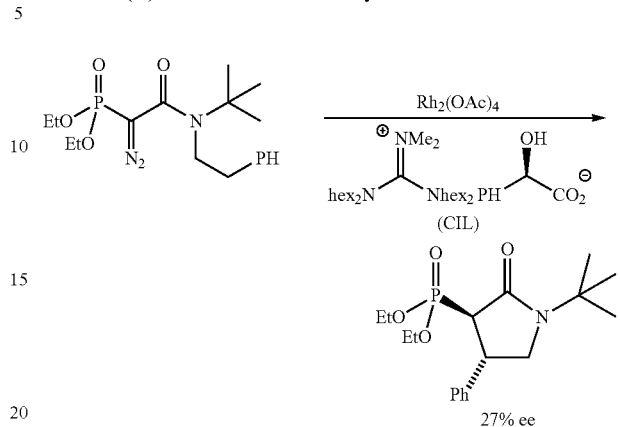

27% ee

In this reaction an α-phosphono-α-diazoacetate was cyclized via a C—H insertion reaction in the presence of Rh$_2$(OAc)$_4$ with a CIL solvent to give a γ-lactam in 72% yield, as a trans/cis mixture (67/33) and with 27% enantiomeric excess. However, undesirably, the IL may not be inert since the mandelate anion may potentially act as a nucleophile or base in many reactions.

Chiral ILs have also found use in the separation sciences. For example, United States Patent Publication No. US 2006/0025598 describes diionic liquid salts having a solid/liquid transition temperature of about 400° C. or less. The diionic liquid salt includes two monoionic groups separated by a bridging group and either two monoionic counter ions or at least one diionic counter ion. The diionic liquid salts may be immobilized as stationary phases for gas chromatography (GC). The IL stationary phases are said to be highly selective, stable and resistant to temperature degradation. In a preferred embodiment, the stationary phases are made from diionic species which are chiral and optically enhanced. In one embodiment the diion or the salt-forming species is chiral, with at least one stereogenic centre to provide racemic or optically enhanced mixtures.

U.S. patent application Ser. No. 11/177,093 describes optically enhanced chiral ionic liquids for gas chromatography and as a reaction solvent. Both optically enhanced chiral cationic and optically enhanced chiral anionic liquids are described. Optically enhanced chiral cations include (−)—N-benzyl-N-methylephedrinium NTf$_2$, isoleucine-based ILs, menthol-substituted methyl imidazolium IL, (−)-cotinine OTf, 1-((R)-1,2-propanediol)-3-methylimidazolium chloride, and a (+)-chloromethyl methyl ether imidazolium IL salts, amongst others.

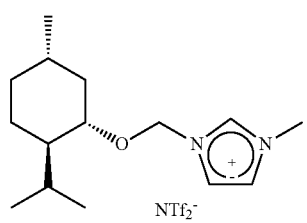

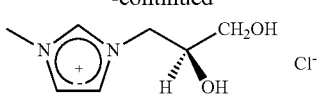

Menthol Substituted IL
1-((R)-1,2-propanediol)-3-methylimidazolium chloride

Chinese Patent Application Publication No. 1 847 201 discloses chiral ionic liquids comprising an imidazole structure substituted with an amino containing group, and its preparation process and application in organic asymmetric catalytic Michael reactions, in which there is said to be excellent chiral catalytic performance. Examples of such compounds include:

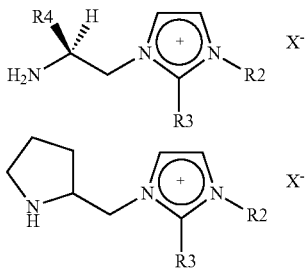

Matos et al recently described CILs based on menthol and borneol moieties linked to alkyl substituted imidazoles through ester functionalities. The introduction of the ester group is said to lead to improved properties such as polymer stabilization. The biodegradability of the compounds is not discussed nor is their success in the induction of chirality in non-chiral substrates.

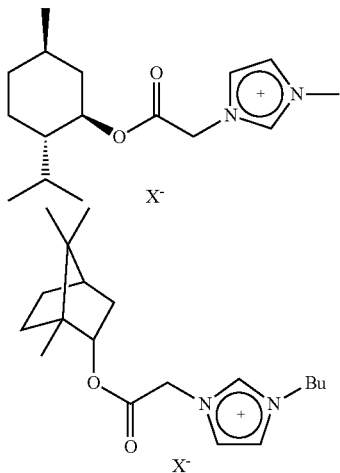

Recently, Luo et al published a review of functionalised chiral ionic liquids. This review gives an excellent overview of chiral ionic liquids role as organocatalysts or non-classical chiral ligands. Two examples of chiral pyridinium ionic liquids were included. Examples shown below:

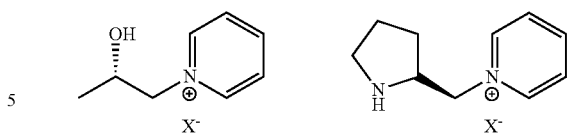

No biodegradation data or toxicity data has been reported, or indeed even discussed in this review. The environmental impact of the chiral ionic liquids as assessed by biodegradation and toxicity studies, has not been investigated by groups working in this area.

Many common ILs have been investigated as alternative solvents for catalytic hydrogenations. Of these studies, the greater part focus on common commercially available ILs of the form Rmim$^+$ (R: alkyl chain) X$^-$. Palladium on Carbon is well known as a universal catalyst for olefin hydrogenation. However, its efficient catalytic activity may lead to poor selectivity.

Accordingly there is a need for additional ILs which combine desirable solvent properties such biodegradability and coordination ability in a solvent that can be tailored to the specific needs of reactions, for example, enhanced conversion and/or selectivity of product. Further examples of chiral ionic liquids are desirable, particularly those which have proven ability to act catalytically and/or induce chirality into the reaction manifold. Although some data clearly exist which indicate that chiral ionic liquids (CILs) have a degree of asymmetric catalytic ability, highly efficient CIL catalysts are limited in number. Thus the need for superior CILs which can optimize asymmetric induction, whilst minimizing any environmental impact is clearly desirable.

In summary, despite the "green" designation, many existing ILs have less than favourable biodegradation profiles and/or have associated toxicity to plant, animal and marine life. Therefore, more biodegradable and/or less toxic ILs are highly desired, particularly those which have the capability to provide a highly polar chiral solvent environment, with negligible vapour pressure and low flammability and that can be recycled after convenient separation of chemical reaction products for chemical reactions (especially those of industrial importance). The invention addresses these deficiencies to a useful degree.

SUMMARY OF THE INVENTION

According to a first aspect of the invention, there is provided a compound comprising an alkyl substituted imidazolium cationic core or an alkyl substituted pyridinium cationic core, having an alkyl ester side chain (-alkyl-C(O)O—) linked thereto and an associated counter anion, characterized in that the —O— atom of the ester side chain links the side chain to an alpha, a beta or a gamma hydroxycarboxylic acid functionality via an alpha, a beta or a gamma hydroxy of the hydroxycarboxylic acid functionality, the hydroxycarboxylic acid functionality having at least one asymmetric carbon.

In a preferred embodiment, the compound of the invention comprises an alkyl substituted imidazolium cationic core.

It will be appreciated that an alkyl substituted imidazolium cationic core and an alkyl substituted pyridinium cationic core comprises at least one N atom in the cyclic core. It will be further appreciated that the core may comprises at least one —N= atom in the cyclic core.

Accordingly, in a preferred embodiment, there is provided a compound comprising an alkyl substituted imidazolium cationic core or an alkyl substituted pyridinium cationic core, having an associated counter anion, characterized in that an —N= atom of the alkyl substituted imidazolium cationic core or an —N= atom of the alkyl substituted pyridinium cationic core is substituted with an alpha, a beta or a gamma hydroxy group of an alpha, a beta or a gamma hydroxycarboxylic acid functionality and the hydroxycarboxylic acid functionality has at least one asymmetric carbon.

In other words, the unsubstituted —N— atom of the 1-substituted imidazole or the pyridine directly replaces the alpha, beta, or gamma-hydroxyl of alpha, beta or gamma hydroxy of the acid functionality to give an imidazolium-substituted or the pyridinium-substituted carboxylic acid functionality that has at least one asymmetric carbon.

The skilled person will appreciate that the —N= atom of the cationic core (imidazolium or pyridinium) is substituted for the alpha, beta or gamma —OH group of the alpha, a beta or a gamma hydroxycarboxylic acid functionality. In other words, the —N= atom replaces the —OH group of the alpha, a beta or a gamma hydroxycarboxylic acid functionality.

In a preferred embodiment, the —N= atom is of an alkyl substituted imidazolium cationic core.

In a preferred embodiment, the alkyl substituted imidazolium cationic core or the alkyl substituted pyridinium cationic core is substituted with an alkyl group of the general formula $C_nH_{2n+1}$ derived from aliphatic hydrocarbons. Alkyl chains can be straight or branched. Particularly preferred are $C_1$-$C_4$ alkyl groups.

The compounds of the invention may be utilised as ionic liquid solvents, particularly chiral ionic liquid solvents (CILs). Advantageously, incorporating the hydroxyl carboxylic acid moiety into the cationic part of the chiral ionic liquid (CIL) molecule, blocks both the normally nucleophilic acid and hydroxyl groups as esters and so (provided there are no strong nucleophiles present, or strong hydrolytic acid or base), the CIL should not interfere with a reaction process and will remain relatively inert. Furthermore, the chirality of the molecule advantageously may assist in inducing stereochemistry into the reaction products and/or enhancing the selectivity and/or reaction conversion rates.

The compounds of the invention are desirable, since they form part of an expandable designer library of ionic liquid solvents that possess tuneable characteristics and yet are economically viable, robust and ideally suited to the preparation of drugs. The ionic liquids of the invention yield an excellent commercial source for tuneable chiral coordinating, biodegradable and non-toxic solvents.

In a preferred embodiment, a compound of the invention may have general formula (I)

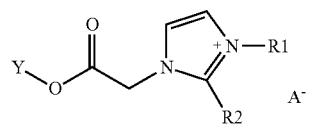

(I)

wherein $R^1$ is a $C_1$-$C_4$ alkyl or $C_1$-$C_4$ alkoxy;

$R^2$ is a —H or $C_1$-$C_4$ alkyl; and

Y is:

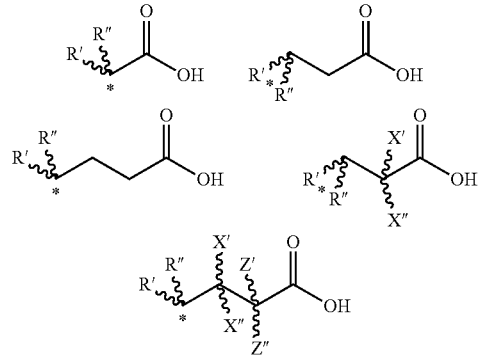

R', R", X', X", Z' and Z" are independently —H; —OH; —$CF_3$; a cyclohexyl; an aryl; a heterocyclic; heteroaryl group; a $C_1$-$C_6$ alkyl or a $C_1$-$C_6$ alkyl ether group, either of which may be branched or unbranched, and the alkyl ether group comprises at least one ether linkage in the alkyl chain;

wherein the cyclohexyl, aryl, heterocyclic or heteroaryl groups may be mono-, di-, tri- or tetra-substituted with substituents independently selected from —H; hydroxy; $C_1$-$C_6$ alkyl; $C_1$-$C_6$ alkoxy; nitro; halo; acyl; phosphine ($PR_2$); diarylphosphine ($PAr_2$); phosphate; phosphite; sulfate; sulfite; phosphonamide; phosphinamide; sulfonamide; sulfonimide; sulfinamide; sulfinimide; carboxylic ester; carbonate; carbamate; or wherein two adjacent substitutions together form a $C_1$-$C_4$ alkylenedioxy ring, and wherein the heterocyclic or heteroaryl group comprises at least one heteroatom N, O or S, with the provision that R' and R" are not simultaneously identical groups; and wherein Y is linked to the ester group oxygen of general formula I at the alpha, beta or gamma asymmetric carbon (*) of the group Y.

It will be appreciated that $A^-$ is a counter anion. In a preferred embodiment, a compound of the invention may have general formula (II)

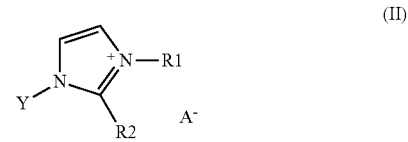

(II)

wherein $R^1$ is a $C_1$-$C_4$ alkyl or $C_1$-$C_4$ alkoxy;

$R^2$ is a —H or $C_1$-$C_4$ alkyl; and

Y is:

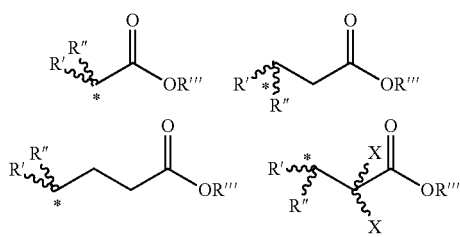

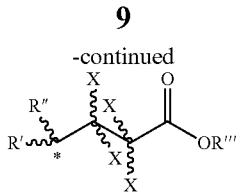

R' and R" and X are independently —H; —OH; —CF$_3$; a cyclohexyl; an aryl; a heterocyclic; heteroaryl group; a C$_1$-C$_6$ alkyl or a C$_1$-C$_6$ alkyl ether group, either of which may be branched or unbranched, and the alkyl ether group comprises at least one ether linkage in the alkyl chain;

R''' is —H, —CF$_3$, a cyclohexyl, an aryl, a heterocyclic, heteroaryl group, a C$_1$-C$_6$ alkyl, a C$_1$-C$_6$ alkyl ether group, either of which may be branched or unbranched, and the alkyl ether group comprises at least one ether linkage in the alkyl chain;

wherein the cyclohexyl, aryl, heterocyclic or heteroaryl groups may be mono-, di-, tri- or tetra-substituted with substituents independently selected from —H; hydroxy; C$_1$-C$_6$ alkyl; C$_1$-C$_6$ alkoxy; nitro; halo; acyl; phosphine (PR$_2$); diarylphosphine (PAr$_2$); phosphate; phosphite; sulfate; sulfite; phosphonamide; phosphinamide; sulfonamide; sulfonimide; sulfinamide; sulfinimide; carboxylic ester; carbonate; carbamate; or wherein two adjacent substitutions together form a C$_1$-C$_4$ alkylenedioxy ring, and wherein the heterocyclic or heteroaryl group comprises at least one heteroatom N, O or S, with the provision that R' and R" are not simultaneously identical groups; and wherein Y is linked to the ester group oxygen of general formula II at the alpha, beta or gamma asymmetric carbon (*) of the group Y.

It will be appreciated that A$^-$ is a counter anion.

Compounds of this aspect of the invention include those based on the following structures:

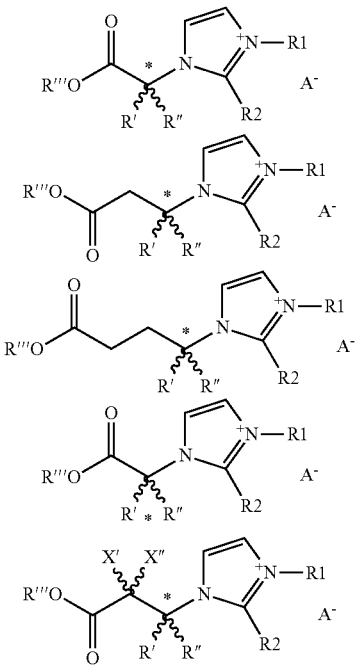

wherein R$^1$ is a C$_1$-C$_4$ alkyl or C$_1$-C$_4$ alkoxy;
R$^2$ is a —H or C$_1$-C$_4$ alkyl; and
R', R", X", X', Y' and Y" are independently —H; —OH; —CF$_3$; a cyclohexyl; an aryl; a heterocyclic; heteroaryl group; a C$_1$-C$_6$ alkyl or a C$_1$-C$_6$ alkyl ether group, either of which may be branched or unbranched, and the alkyl ether group comprises at least one ether linkage in the alkyl chain;

R''' is —H; —CF$_3$; a cyclohexyl; an aryl; a heterocyclic; heteroaryl group; a C$_1$-C$_6$ alkyl or a C$_1$-C$_6$ alkyl ether group, either of which may be branched or unbranched, and the alkyl ether group comprises at least one ether linkage in the alkyl chain;

wherein the cyclohexyl, aryl, heterocyclic or heteroaryl groups may be mono-, di-, tri- or tetra-substituted with substituents independently selected from —H; hydroxy; C$_1$-C$_6$ alkyl; C$_1$-C$_6$ alkoxy; nitro; halo; acyl; phosphine (PR$_2$); diarylphosphine (PAr$_2$); phosphate; phosphite; sulfate; sulfite; phosphonamide; phosphinamide; sulfonamide; sulfonimide; sulfinamide; sulfinimide; carboxylic ester; carbonate; carbamate; or wherein two adjacent substitutions which together form a C$_1$-C$_4$ alkylenedioxy ring, and wherein the heterocyclic or heteroaryl group comprising at least one heteroatom N, O or S, with the provision that R' and R" are not simultaneously identical groups.

It will be appreciated that A$^-$ is a counter anion.

In a particularly preferred embodiment, a compound of the invention may have general formula (III)

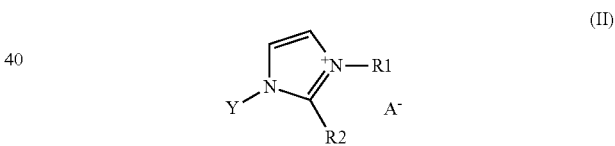

(II)

wherein R$^1$ is a C$_1$-C$_4$ alkyl or C$_1$-C$_4$ alkoxy;
R$^2$ is a —H or C$_1$-C$_4$ alkyl; and
Y is:

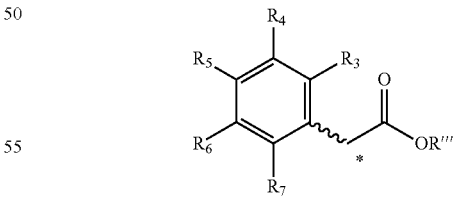

R''' is —H, —CF$_3$, a cyclohexyl, an aryl, a heterocyclic, heteroaryl group, a C$_1$-C$_6$ alkyl, a C$_1$-C$_6$ alkyl ether group, either of which may be branched or unbranched, and the alkyl ether group comprises at least one ether linkage in the alkyl chain; and R$^3$, R$^4$, R$^5$, R$^6$ and R$^7$ are independently —H; —OH; —CF$_3$; a cyclohexyl; an aryl; a heterocyclic; heteroaryl group; a nitro; halo; acyl; phosphine (PR$_2$); diarylphosphine (PAr$_2$); phosphate; phosphite; sulfate; sulfite; phosphonamide; phosphinamide; sulfonamide; sulfonimide; sulfinamide; sulfinimide; carboxylic ester; carboxylic amide; carbonate; carbamate; or wherein two adjacent substitutions which together form a $C_1$-$C_4$ alkylenedioxy ring, and wherein the cyclohexyl, aryl, heterocyclic or heteroaryl groups may be mono-, di-, tri- or tetra-substituted with substituents independently selected from —H; hydroxy; $C_1$-$C_6$ alkyl; $C_1$-$C_6$ alkoxy; nitro; halo; acyl; phosphine ($PR_2$); diarylphosphine ($PAr_2$); phosphate; phosphite; sulfate; sulfite; phosphonamide; phosphinamide; sulfonamide; sulfonimide; sulfinamide; sulfinimide; carboxylic ester; carbonate; carbamate; or wherein two adjacent substitutions together form a $C_1$-$C_4$ alkylenedioxy ring, and wherein the heterocyclic or heteroaryl group comprises at least one heteroatom N, O or S; and wherein Y is linked to the ester group oxygen of general formula II at the alpha, beta or gamma asymmetric carbon (*) of the group Y.

In another preferred embodiment, a compound of the invention may have general formula (III)

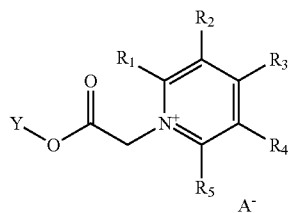

(III)

wherein $R^1$, $R^2$, $R^3$, $R^4$, $R^5$ are independently —H; —OH; —$CF_3$; a cyclohexyl; an aryl; a heterocyclic; heteroaryl group; a nitro; halo; acyl; phosphine ($PR_2$); diarylphosphine ($PAr_2$); phosphate; phosphite; sulfate; sulfite; phosphonamide; phosphinamide; sulfonamide; sulfonimide; sulfinamide; sulfinimide; carboxylic ester; carboxylic amide; carbonate; carbamate; or wherein two adjacent substitutions which together form a $C_1$-$C_4$ alkylenedioxy ring, and wherein the cyclohexyl; aryl; heterocyclic or heteroaryl groups may be mono-, di-, tri- or tetra-substituted with substituents independently selected from —H; hydroxy; $C_1$-$C_6$ alkyl; $C_1$-$C_6$ alkoxy; nitro; halo; acyl; phosphine ($PR_2$); diarylphosphine ($PAr_2$); phosphate; phosphite; sulfate; sulfite; phosphonamide; phosphinamide; sulfonamide; sulfonimide; sulfinamide; sulfinimide; carboxylic ester; carboxylic amide; carbonate; carbamate or wherein two adjacent substitutions which together form a $C_1$-$C_4$ alkylenedioxy ring, and wherein the heterocyclic or heteroaryl group comprises at least one heteroatom N, O or S;

Y is:

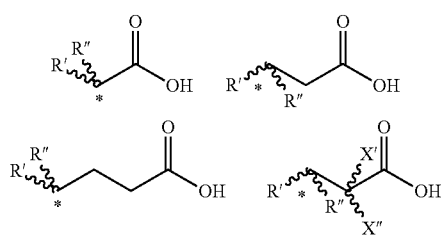

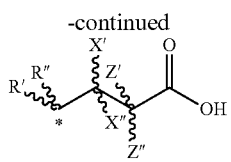

R', R", X', X", Z' and Z" are independently —H; —OH; —$CF_3$; a cyclohexyl; an aryl; a heterocyclic; a heteroaryl group; a $C_1$-$C_6$ alkyl or a $C_1$-$C_6$ alkyl ether group, either of which may be branched or unbranched, and the alkyl ether group comprises at least one ether linkage in the alkyl chain;

wherein the cyclohexyl, aryl, heterocyclic or heteroaryl groups may be mono-, di-, tri- or tetra-substituted with substituents independently selected from —H; hydroxy; $C_1$-$C_6$ alkyl; $C_1$-$C_6$ alkoxy; nitro; halo; acyl; phosphine ($PR_2$); diarylphosphine ($PAr_2$); phosphate; phosphite; sulfate; sulfite; phosphonamide; phosphinamide; sulfonamide; sulfonimide; sulfinamide; sulfinimide; carboxylic ester; carboxylic amide; carbonate; carbamate or wherein two adjacent substitutions which together form a $C_1$-$C_4$ alkylenedioxy ring, and wherein the heterocyclic or heteroaryl group comprises at least one heteroatom N, O or S, with the provision that R' and R" are not simultaneously identical groups; and wherein Y is linked to the ester group oxygen of general formula III at the alpha, beta or gamma asymmetric carbon (*) of the group Y.

It will be appreciated that $A^-$ is a counter anion.

In a preferred embodiment, a compound of the invention may have general formula (IV)

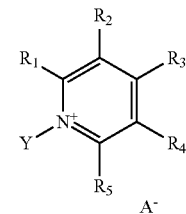

(IV)

wherein $R^1$, $R^2$, $R^3$, $R^4$, $R^5$ are independently —H; —OH; —$CF_3$; a cyclohexyl; an aryl; a heterocyclic; heteroaryl group; a nitro; halo; acyl; phosphine ($PR_2$); diarylphosphine ($PAr_2$); phosphate; phosphite; sulfate; sulfite; phosphonamide; phosphinamide; sulfonamide; sulfonimide; sulfinamide; sulfinimide; carboxylic ester; carboxylic amide; carbonate; carbamate or wherein two adjacent substitutions which together form a $C_1$-$C_4$ alkylenedioxy ring, and wherein the cyclohexyl, aryl, heterocyclic or heteroaryl groups may be mono-, di-, tri- or tetra-substituted with substituents independently selected from —H; hydroxy; $C_1$-$C_6$ alkyl; $C_1$-$C_6$ alkoxy; nitro; halo; acyl; phosphine ($PR_2$); diarylphosphine ($PAr_2$); phosphate; phosphite; sulfate; sulfite; phosphonamide; phosphinamide; sulfonamide; sulfonimide; sulfinamide; sulfinimide; carboxylic ester; carboxylic amide; carbonate; carbamate or wherein two adjacent substitutions which together form a $C_1$-$C_4$ alkylenedioxy ring; and wherein the heterocyclic or heteroaryl group comprising at least one heteroatom N, O or S; and Y is:

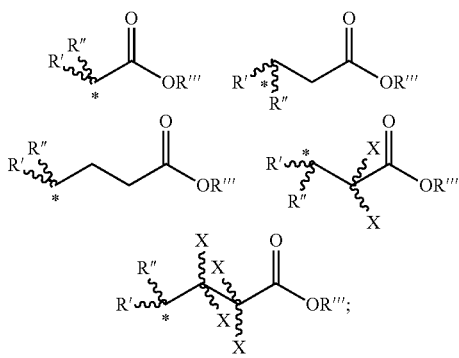

and

R' and R" and X are independently —H; —OH; —CF$_3$; a cyclohexyl; an aryl; a heterocyclic; heteroaryl group; a C$_1$-C$_6$ alkyl or a C$_1$-C$_6$ alkyl ether group, either of which may be branched or unbranched, and the alkyl ether group comprises at least one ether linkage in the alkyl chain;

R'" is —H; —CF$_3$; a cyclohexyl; an aryl; a heterocyclic; heteroaryl group; a C$_1$-C$_6$ alkyl or a C$_1$-C$_6$ alkyl ether group, either of which may be branched or unbranched, and the alkyl ether group comprises at least one ether linkage in the alkyl chain; and wherein the cyclohexyl, aryl, heterocyclic or heteroaryl groups may be mono-, di-, tri- or tetra-substituted with substituents independently selected from —H; hydroxy; C$_1$-C$_6$ alkyl; C$_1$-C$_6$ alkoxy; nitro; halo; acyl; phosphine (PR$_2$); diarylphosphine (PAr$_2$); phosphate; phosphite; sulfate; sulfite; phosphonamide; phosphinamide; sulfonamide; sulfonimide; sulfinamide; sulfinimide; carboxylic ester; carboxylic amide; carbonate; carbamate or wherein two adjacent substitutions which together form a C$_1$-C$_4$ alkylenedioxy ring, and wherein the heterocyclic or heteroaryl group comprising at least one heteroatom N, O or S, with the provision that R' and R" are not simultaneously identical groups; and wherein Y of general formula (IV) is linked to the alpha, beta or gamma asymmetric carbon (1 of the group Y.

It will be appreciated that A$^-$ is a counter anion.

Compounds of this aspect of the invention include those based on the following structures:

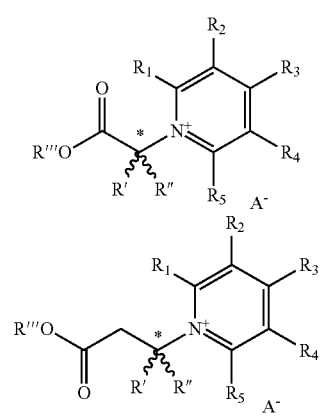

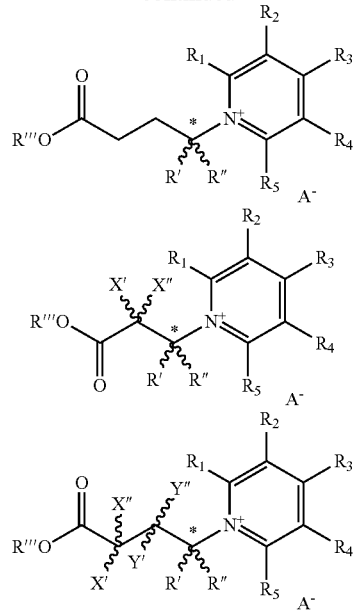

wherein R$^1$, R$^2$, R$^3$, R$^4$, R$^5$ are independently —H; —OH; —CF$_3$; a cyclohexyl; an aryl; a heterocyclic; heteroaryl group; a nitro; halo; acyl; phosphine (PR$_2$); diarylphosphine (PAr$_2$); phosphate; phosphite; sulfate; sulfite; phosphonamide; phosphinamide; sulfonamide; sulfonimide; sulfinamide; sulfinimide; carboxylic ester; carboxylic amide; carbonate; carbamate or wherein two adjacent substitutions which together form a C$_1$-C$_4$ alkylenedioxy ring; and wherein the cyclohexyl; aryl, heterocyclic or heteroaryl groups may be mono-, di-, tri- or tetra substituted with substituents independently selected from —H; hydroxy; C$_1$-C$_6$ alkyl; C$_1$-C$_6$ alkoxy; nitro; halo; acyl; phosphine (PR$_2$); diarylphosphine (PAr$_2$); phosphate; phosphite; sulfate; sulfite; phosphonamide; phosphinamide; sulfonamide; sulfonimide; sulfinamide; sulfinimide; carboxylic ester; carboxylic amide; carbonate; carbamate or wherein two adjacent substitutions which together form a C$_1$-C$_4$ alkylenedioxy ring, and wherein the heterocyclic or heteroaryl group comprising at least one heteroatom N, O or S; and R', R", X", X', Y' and Y" are independently —H; —OH; —CF$_3$; a cyclohexyl; an aryl; a heterocyclic; heteroaryl group; a C$_1$-C$_6$ alkyl or a C$_1$-C$_6$ alkyl ether group, either of which may be branched or unbranched, and the alkyl ether group comprises at least one ether linkage in the alkyl chain;

R'" is —H, —CF$_3$, a cyclohexyl, an aryl, a heterocyclic, heteroaryl group, a C$_1$-C$_6$ alkyl, a C$_1$-C$_6$ alkyl ether group, either of which may be branched or unbranched, and the alkyl ether group comprises at least one ether linkage in the alkyl chain;

wherein the cyclohexyl, aryl, heterocyclic or heteroaryl groups may be mono-, di-, tri- or tetra-substituted with substituents independently selected from —H; hydroxy; C$_1$-C$_6$ alkyl; C$_1$-C$_6$ alkoxy; nitro; halo; acyl; phosphine (PR$_2$); diarylphosphine (PAr$_2$); phosphate; phosphite; sulfate; sulfite; phosphonamide; phosphinamide; sulfonamide; sulfonimide; sulfinamide; sulfinimide; carboxylic ester; carboxylic amide; carbonate; carbamate or wherein two adjacent substitutions which together form a C$_1$-C$_4$ alkylenedioxy ring, and wherein the heterocyclic or heteroaryl group comprising at least one heteroatom N, O or S, with the provision that R' and R" are not simultaneously identical groups.

It will be appreciated that A⁻ is a counter anion.

In a preferred embodiment, a compound of the invention may have general formula (V)

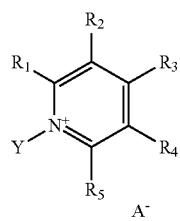

(V)

wherein $R^1$, $R^2$, $R^3$, $R^4$, $R^5$ are independently —H; —OH; —$CF_3$; a cyclohexyl; an aryl; a heterocyclic; heteroaryl group; a nitro; halo; acyl; phosphine ($PR_2$); diarylphosphine ($PAr_2$); phosphate; phosphite; sulfate; sulfite; phosphonamide; phosphinamide; sulfonamide; sulfonimide; sulfinamide; sulfinimide; carboxylic ester; carboxylic amide; carbonate; carbamate or wherein two adjacent substitutions which together form a $C_1$-$C_4$ alkylenedioxy ring, and wherein the cyclohexyl, aryl, heterocyclic or heteroaryl groups may be mono-, di-, tri- or tetra-substituted with substituents independently selected from —H; hydroxy; $C_1$-$C_6$ alkyl; $C_1$-$C_6$ alkoxy; nitro; halo; acyl; phosphine ($PR_2$); diarylphosphine ($PAr_2$); phosphate; phosphite; sulfate; sulfite; phosphonamide; phosphinamide; sulfonamide; sulfonimide; sulfinamide; sulfinimide; carboxylic ester; carboxylic amide; carbonate; carbamate or wherein two adjacent substitutions which together form a $C_1$-$C_4$ alkylenedioxy ring; and wherein the heterocyclic or heteroaryl group comprising at least one heteroatom N, O or S; and Y is:

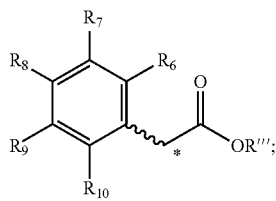

R''' is —H, —$CF_3$, a cyclohexyl, an aryl, a heterocyclic, heteroaryl group, a $C_1$-$C_6$ alkyl, a $C_1$-$C_6$ alkyl ether group, either of which may be branched or unbranched, and the alkyl ether group comprises at least one ether linkage in the alkyl chain; and $R^6$, $R^7$, $R^8$, $R^9$ and $R^{10}$ are independently —H; —OH; —$CF_3$; a cyclohexyl; an aryl; a heterocyclic; heteroaryl group; a nitro; halo; acyl; phosphine ($PR_2$); diarylphosphine ($PAr_2$); phosphate; phosphite; sulfate; sulfite; phosphonamide; phosphinamide; sulfonamide; sulfonimide; sulfinamide; sulfinimide; carboxylic ester; carboxylic amide; carbonate; carbamate or wherein two adjacent substitutions which together form a $C_1$-$C_4$ alkylenedioxy ring, and wherein the cyclohexyl, aryl, heterocyclic or heteroaryl groups may be mono-, di-, tri- or tetra-substituted with substituents independently selected from —H; hydroxy; $C_1$-$C_6$ alkyl; $C_1$-$C_6$ alkoxy; nitro; halo; acyl; phosphine ($PR_2$); diarylphosphine ($PAr_2$); phosphate; phosphite; sulfate; sulfite; phosphonamide; phosphinamide; sulfonamide; sulfonimide; sulfinamide; sulfinimide; carboxylic ester; carboxylic amide; carbonate; carbamate or wherein two adjacent substitutions which together form a $C_1$-$C_4$ alkylenedioxy ring, and wherein the heterocyclic or heteroaryl group comprising at least one heteroatom N, O or S, with the provision that R' and R" are not simultaneously identical groups; and wherein Y of general formula (V) is linked to the alpha, beta or gamma asymmetric carbon (*) of the group Y.

It will be appreciated that A⁻ is a counter anion. Used herein, an alkyl group is any of a series of univalent groups of the general formula $C_nH_{2n+1}$ derived from aliphatic hydrocarbons. Alkyl chains can be straight or branched. The skilled person will appreciate that straight means linear and unbranched. The methyl group (—$CH_3$) represents a $C_1$ alkyl group, ethyl (—$C_2H_5$) represents a $C_2$ alkyl group, nonyl group represents a $C_9$ alkyl group, dodecyl group represents a $C_{12}$ group, etc.

An ether group has an oxygen atom connected to two alkyl groups, which may be further derivatized (general formula R—O—R'). A typical example is ethoxyethane ($CH_3$—$CH_2$—O—$CH_2$—$CH_3$).

An ester group may be represented by RC(O)—OR and comprises an acid hydroxy group adjacent to a carbonyl group, wherein the acid hydroxy group is esterified. An alkyl ester group may be represented by -alkyl-C(O)—O—R, wherein the alkyl group is as defined above.

An acid amide may be represented by RC(O)NHR, in the case of a primary amide. A secondary amide group may be represented by RC(O)NR'R", wherein the R' and R" may be the same or different.

A thioester may be represented by the group RC=S—OR.

As described herein, when an alkyl group is said to comprises at least one ether linkage, this is intended to mean that at least one carbon (—HCH—) in the alkyl chain is substituted by an oxygen (—O—) atom, to give an alkyl chain containing at least one ether linkage. The number of carbon atoms substituted by oxygen depends on the number of ether linkages provided in the chain.

A chiral or stereogenic carbon is a carbon atom which is asymmetric. A chiral or asymmetric carbon to be chiral, it follows that the carbon atom is $sp^3$-hybridized and there are four different groups attached to the carbon atom or stereogenic centre.

In a preferred embodiment, the compounds of the invention have an alkyl ester side chain in which the alkyl terminus is directly attached to the imidazole ring at the 3-position or pyridine ring at the 1 position. This means that the -alkyl-C(O)OR side chain is directly attached to a nitrogen of the imidazolium ring or nitrogen of the pyrdinium ring through the -alkyl-group end of the side chain. For example, if the -alkyl-C(O)OR side chain is a methyl ester side chain, then the ester functionality is one carbon away from the nitrogen heterocycle core. If the -alkyl-C(O)OR side chain is an ethyl ester side chain, then the ester functionality is two carbon atoms away from the core, and so on. It is preferred that the alkyl ester side chain comprises a methyl, ethyl or propyl alkyl group, the alkyl terminus of which is preferably directly linked to the nitrogen atom of the imidazolium ring or nitrogen of the pyridinium ring. Most preferred of all, are compounds which comprise methyl ester side chains (—$CH_2$C(O)OR) wherein the methyl groups links the ester functionality to the nitrogen of the imidazolium ring. These structures are favoured because a good balance between easy of synthesis, stability, low antimicrobial toxicity and high biodegradability is achieved.

In one embodiment, the compounds of the invention comprise an alpha or a beta or a gamma hydroxycarboxylic acid functionality, wherein the acid functionality may be a carboxylic acid group (—COOH), a $C_1$-$C_6$ acid ester group (—COOR), a $C_1$-$C_6$ acid amide group (—CONHR or —CONRR) or a $C_1$-$C_6$ acid thioester group (—CSOR), wherein R independently represents a $C_1$-$C_6$ alkyl group or a $C_1$-$C_6$ alkyl ether group, both of which may be branched or unbranched, and the alkyl ether group comprises at least one ether linkage in the alkyl chain. In particularly preferred compounds, R is a $C_1$-$C_6$ alkyl ether group having one ether oxygen substituted into the alkyl chain to replace one carbon atom therein.

Thus, the compounds of the invention may be derived from any of the chiral alpha, beta or gamma hydroxy carboxylic acid building blocks shown below or derivates of same, wherein the molecules may be derivatized by further substitution with groups R, —OH, X or Y, as described later herein.

The CIL compounds of the invention comprise an alkyl ether side chain linked to the IL core, wherein the —O— atom of the alkyl ester bond is derived from the alpha hydroxyl group of a chiral alpha hydroxycarboxylic acid functionality or comprise a chiral beta hydroxy group of a beta hydroxycarboxylic acid functionality or a chiral gamma hydroxy group of a gamma hydroxycarboxylic acid functionality (—O— atom of the alkyl ester bond is highlighted in bold as the oxygen of the hydroxy group in the moieties below). The hydroxy group from which the alkyl ester bond is derived is indicated in bold in the representative structure below.

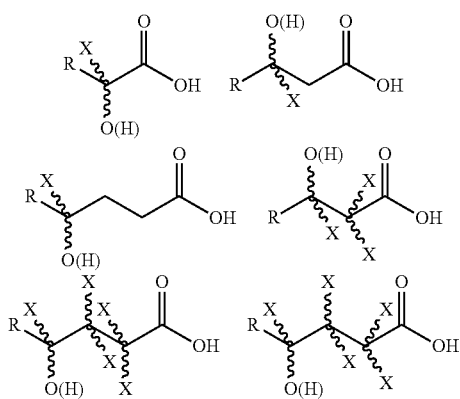

Preferably, the compounds of the invention comprise at least one chiral (asymmetric) centre. at The least one chiral centre is preferably located at the asymmetric (stereogenic) carbon which is substituted with the alkyl ester group which links the chiral moiety to the IL core (corresponds to the carbon substituted with the hydroxy of the carboxylic acid moiety, the hydroxy is indicated in bold above). Other possible asymmetric carbon sites are shown in the representative molecules above, to which the groups X may be directly attached. The chiral centre(s) have four different groups attached thereto. Suitably, R and X may be different and may be independently selected from the group consisting of —H, —OH, —$CF_3$, a cyclohexyl, an aryl, a heterocyclic, heteroaryl group, $C_1$-$C_6$ alkyl, a $C_1$-$C_6$ alkyl ether group, either of which may be branched or unbranched and the alkyl ether group comprises at least one ether linkage in the alkyl chain; wherein the cyclohexyl, aryl, heterocyclic or heteroaryl groups may be mono-, di- or tri-substituted with substituents independently selected from hydrogen, hydroxy, $C_1$-$C_6$ alkyl, $C_1$-$C_6$ alkoxy, nitro, halo, acyl, phosphine ($PR_2$), diarylphosphine ($PAr_2$), phosphate, phosphite, sulfate, sulfite, phosphonamide, phosphinamide, sulfonamide, sulfonimide, sulfinamide, sulfinimide, carboxylic ester, carbonate, carbamate or two adjacent substitutions which together form a $C_1$-$C_4$ alkylenedioxy ring, and wherein the heteroaryl group comprising at least one heteroatom N, O or S; with the provision that R and X are not both simultaneously identical groups. In other words, substituents R and X cannot be identical, since if this is the case, the carbon to which the groups are attached is not asymmetric (the molecule may still be chiral if an axis of chirality is present even without stereocentres). Accordingly, the compounds of the invention comprise compounds in racemic mixtures where the enantiomers are present in equal amounts or in enantiomeric mixtures wherein one enantiomer is present in excess of another or indeed enantiomerically pure where the compound of the invention is available as 100% enantiomer.

In one preferred embodiment, the compounds of the invention comprise a chiral alpha, a chiral beta or a chiral gamma hydroxycarboxylic acid functionality, wherein the acid functionality is a $C_1$-$C_6$ acid ester group —COOR, wherein R is a $C_1$-$C_6$ alkyl group or a $C_1$-$C_6$ alkyl ether group, either of which may be branched or unbranched, and the alkyl ether group comprises at least one ether linkage in the alkyl chain. The compounds are advantageous since they may easily be further derivatized at any of the reactive groups present. Furthermore, the compounds containing coordinating carbonyl and ester oxygen sites which may advantageously interact with reactants in a positive manner with regard to promoting or enhancing stereoinduction, product selectivity and conversion in a chemical reaction in which the CIL is employed as solvent or co-solvent etc.

In another embodiment, the compounds of the invention comprise a chiral alpha, a chiral beta or a chiral gamma hydroxycarboxylic acid functionality, wherein the acid functionality is a $C_1$-$C_6$ acid amide group —CONHR or —CONRR, wherein R is independently a $C_1$-$C_6$ alkyl group or a $C_1$-$C_6$ alkyl ether group, either of which may be branched or unbranched, and the alkyl ether group comprises at least one ether linkage in the alkyl chain, or R and R together may form a heterocyclic ring having 5 to 7 atoms, wherein the ring may comprise at least one other heteroatom in addition to the amide nitrogen. Preferably the heterocyclic ring comprises 6 atoms in the ring. Particularly preferred compounds comprise a heteroatom ring, which comprises at least one oxygen atom, such as cyclic ethers. Such compounds would be desirable, since they may have improved stability over the ester analogous compounds. In addition, the amides may have superior co-coordinating properties than the ester versions. Primary and secondary amide CILs may advantageously have additional desirable hydrogen bonding properties.

In a different embodiment, the compounds of the invention comprise an alpha, a beta or a gamma hydroxycarboxylic acid functionality, wherein the acid functionality is a $C_1$-$C_6$ thioester group —CSOR, wherein R a $C_1$-$C_6$ alkyl group or a $C_1$-$C_6$ alkyl ether group both of which may be branched or unbranched and the alkyl ether group comprises at least one ether linkage in the alkyl chain. These ILs may be advantageous in reactions involving enzymes. They may be desirable in reactions that involve heavy metals.

In a preferred embodiment, the compounds of the invention comprise a chiral alpha hydroxycarboxylic acid functionality, which may be a malic acid functionality, a lactic acid functionality or mandelic acid functionality. However, the malic acid functionality, a lactic acid functionality or mandelic acid functionality are particularly preferred in the CIL compound of the present invention.

In another preferred embodiment, the compounds of the invention comprise a chiral beta hydroxycarboxylic acid functionality which may be a 3-hydroxybutyric acid functionality, a 3-hydroxyvaleric acid functionality, a 3-hydroxyhexanoic acid functionality or a 3-hydroxy-3-phenyl propanoic acid functionality. Particularly preferred are 3-hydroxy acid functionalities of bacterial origin that will advantageously have high biodegradability and/or biorenewability. Advantageously, β-hydroxy acids readily link into biochemical pathways because of β-oxidation in fatty acid chains. Notably β-hydroxy carbonyls are aldols and the sidechain can readily cleave by elimination, which favours CIL degradation.

The compounds of the invention have imidazolium or pyridinium cores which may be substituted around the imidazolium or pyridinium ring by at least one $C_1$-$C_5$ alkyl substituent, $C_1$-$C_5$ alkoxy substituent or by at least one halogenated alkyl substituents. Suitably, the alkyl substituted imidazolium core may possess a $C_1$-$C_4$ alkyl substituent at the 1-position of the imidazolium core. However, $C_1$-$C_2$ alkyl substituents at the 1-position are the preferred substituents. The most favoured substituents are methyl substituents at the 1-position.

It is also possible to have further substituents on the imidazolium or pyrimidium ring, such further substituent may be at least one $C_1$-$C_5$ alkyl substituent or at least one halogenated alkyl substituent, such as trifluoromethyl.

Thus, the compounds of the invention comprise IL compounds having an alkyl substituted imidazole ring which may be substituted in at least one position with an alkyl group selected from the group consisting of 1-methyl, 2-methyl, 4-methyl, 5-methyl, 1-ethyl, 2-ethyl, 4-ethyl, 5-ethyl, 1-propyl, 2-propyl, 4-propyl, 5-propyl or a 4-trifluoromethyl group, which may be suitably branched or unbranched. The most preferred compounds of the invention comprise a 1-methyl or 1 ethyl substituent on the imidazolium core. However, the most preferred alkyl substituent is a 1-methyl substituent on the 1 position of the imidazolium ring.

Suitably, the negatively charged counter anion (A) may be selected from the group consisting of: Cl, Br, I, $PF_6$, $BF_4$, $OctOSO_3$, $CH_3OSO_3$, $SO_4$, $NTf_2$ or $N(CN)_2$, tosylate, hydroxylate, camphorsulfonate, mandelate, lactate, tartrate, quinate, carboxylate derivatives of aminoacids, hydrogen sulfate, methyl sulfate, ethyl sulfate, butyl sulfate, hexyl sulfate, heptadecafluorooctanesulfonate, 2-(2-methoxyethoxy)-ethylsulfate, methanesulfonate, trifluoromethanesulfonate, nonafluorobutanesulfonate, p-toluenesulfonate, phosphate, dimethyl phosphate, diethyl phosphate, dibutyl phosphate, dihexyl phosphate, dioctyl phosphate, bis(pentafluoroethyl) phosphinate, bis(2,4,4-trimethylpentyl)-phosphinate, tris(pentafluoroethyl)trifluorophosphate, tris(heptafluoropropyl)trifluorophosphate, tris(nonafluorobutyl)trifluorophosphate, diethylphosphate, nitrate, thiocyanate, tricyanomethanide, bis(pentafluoroethylsulfonyl)imide, bis(trifluoromethyl)imide, tris(trifluoromethylsulfonyl)methide, bis(methanesulfonyl)amide, 2,2,2-trifluoro-N-(trifluoromethylsulfonyl)acetamide, tetracyanoborate, bis[oxalato]borate, bis-[1,2-benzenediolato(2-)]borate, bis-[salicylato(2-)]borate, bis-[malonato(2-)]-borate, bis-[2,2'biphenyl-diolato-(2-)-O,O']-borate, acetate, trifluoroacetate, decanoate, hexafluoroantimonate, tetrachloroaluminate and cobalttetracarbonyl.

Particularly preferred anions are Cl, Br, I, $PF_6$, $BF_4$, $OctOSO_3$, $CH_3OSO_3$, $SO_4$, $NTf_2$ or $N(CN)_2$.

Suitably, the negatively charged counter anion may be Br, $PF_6$, $BF_4$, $OctOSO_3$, $CH_3OSO_3$, $SO_4$, $NTf_2$ or $N(CN)_2$. Desirably, anions may be $OctOSO_3$, $NTf_2$ or $N(CN)_2$.

The most preferred anion is $OctOSO_3$. The person skilled in the art will appreciate that many other counteranions may be suitably used, with low toxicity examples such as $OctOSO_3$, $CH_3OSO_3$, $HSO_4$, and $SO_4$ being especially preferred.

In a particularly preferred embodiment, the compounds of the invention have general formula V or VI

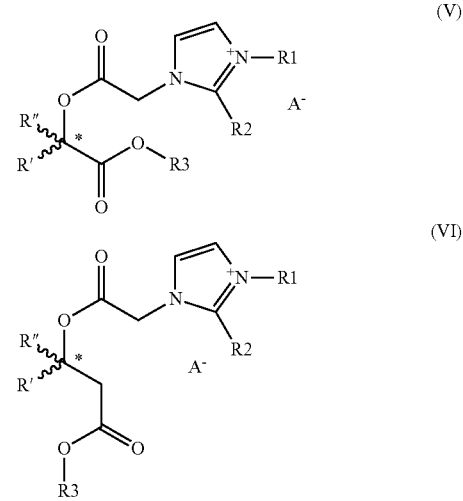

wherein $R^1$ is a $C_1$-$C_4$ alkyl or $C_1$-$C_4$ alkoxy;

$R^2$ is a —H or $C_1$-$C_4$ alkyl;

R' is —H, —OH, —$CF_3$, a cyclohexyl, an aryl, a heterocyclic, heteroaryl group, a $C_1$-$C_6$ alkyl, a $C_1$-$C_6$ alkyl ether group, either of which may be branched or unbranched, and the alkyl ether group comprises at least one ether linkage in the alkyl chain;

R" is a —H, —OH, —$CF_3$, a cyclohexyl, an aryl, a heterocyclic, heteroaryl group, $C_1$-$C_6$ alkyl, a $C_1$-$C_6$ alkyl ether group, either of which may be branched or unbranched, and the alkyl ether group comprises at least one ether linkage in the alkyl chain wherein the cyclohexyl, aryl, heterocyclic or heteroaryl groups may be mono-, di-, tri- or tetra-substituted with substituents independently selected from —H, hydroxy, $C_1$-$C_6$ alkyl, $C_1$-$C_6$ alkoxy, nitro, halo, acyl, phosphine ($PR_2$), diarylphosphine ($PAr_2$), phosphate, phosphite, sulfate, sulfite, phosphonamide, phosphinamide, sulfonamide, sulfonimide, sulfinamide, sulfinimide, carboxylic ester, carbonate, carbamate or wherein two adjacent substitutions which together form a $C_1$-$C_4$ alkylenedioxy ring, and wherein the heterocyclic or heteroaryl group comprising at least one heteroatom N, O or S, with the provision that R' and R" are not simultaneously identical groups;

$R^3$ is a $C_1$-$C_6$ alkyl, or a $C_1$-$C_6$ alkyl ether group, either of which may be branched or unbranched and the alkyl ether group comprises at least one ether linkage in the alkyl chain; and $A^-$ is Br, $PF_6$, $BF_4$, $OctOSO_3$, $NTf_2$ or $N(CN)_2$.

Suitably, the $C_1$-$C_6$ alkyl ether group may include groups such as —$CH_2CH_2OCH_3$, —$CH_{—2}CH_2OCH_2CH_3$, —$CH_2CH_2OCH_2CH_2CH_3$ or —$CH_2CH_2OCH_2CH_2OCH_2CH_3$. Branched analogues also fall within the scope of the invention.

Suitable aryl groups include phenyl, suitable heterocyclic rings include pyrrolidine and heteroaryl rings comprise pyridine or pyrrole etc.

In a particularly preferred embodiment, the compounds of the invention have general formula V or VI

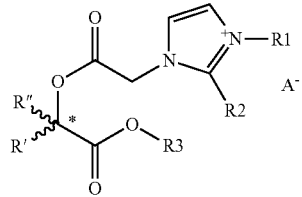

(V)

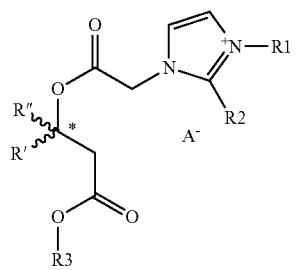

(VI)

wherein $R^1$ is a $C_1$-$C_4$ alkyl;

$R^2$ is a —H or a $C_1$-$C_4$ alkyl;

R' is —H, —OH, —$CF_3$, a cyclohexyl, an aryl, a heterocyclic, heteroaryl group, a $C_1$-$C_6$ alkyl or a $C_1$-$C_6$ alkyl ether group, either of which may be branched or unbranched and the alkyl ether group comprises at least one ether linkage in the alkyl chain;

R" is a —H, —OH, —$CF_3$, a cyclohexyl, an aryl, a heterocyclic, heteroaryl group, $C_1$-$C_6$ alkyl or a $C_1$-$C_6$ alkyl ether group, either of which may be branched or unbranched, and the alkyl ether group comprises at least one ether linkage in the alkyl chain, with the provision that R' and R" are not simultaneously identical groups;

wherein the cyclohexyl, aryl, heterocyclic or heteroaryl groups may be mono-, di-, tri or tetra-substituted with substituents independently selected from —H; hydroxy; $C_1$-$C_6$ alkyl; $C_1$-$C_6$ alkoxy; nitro; halo; acyl; phosphine ($PR_2$); diarylphosphine ($PAr_2$); phosphate; phosphite; sulfate; sulfite; phosphonamide; phosphinamide; sulfonamide; sulfonimide; sulfinamide; sulfinimide; carboxylic ester; carbonate; carbamate or wherein two adjacent substitutions which together form a $C_1$-$C_4$ alkylenedioxy ring, and wherein the heterocyclic or heteroaryl group comprises at least one heteroatom N, O or S; and $R^3$ is a $C_1$-$C_6$ alkyl, or a $C_1$-$C_6$ alkyl ether group, either of which may be branched or unbranched, and the alkyl ether group comprises at least one ether linkage in the alkyl chain; and A is $OctOSO_3$ or $NTf_2$.

In a particularly preferred embodiment, R" is —$CH_3$.

Suitably, the $C_1$-$C_6$ alkyl ether group may be —$CH_2CH_2OCH_3$, —$CH_2CH_2OCH_2CH_3$, —$CH_2CH_2OCH_2CH_2CH_3$ or —$CH_2CH_2OCH_2CH_2OCH_3$. Branched alkyl ester analogues also fall within the scope of the invention.

Suitably, the preferred compounds of the invention have a chiral alpha hydroxycarboxylic acid functionality which comprises a lactic acid functionality or a mandelic acid functionality. Particularly preferred compounds are those comprising the mandelate functionality having an aryl group substituent on the asymmetric carbon to which the chiral alpha hydroxy group (esterified in the CIL molecule) is attached, since these examples are expected to exhibit superior potential substrate interaction sites. In one embodiment, the compounds comprise a chiral beta hydroxycarboxylic acid functionality, which may be a chiral beta-hydroxybutyric acid functionality or a chiral 3-hydroxy-3-phenyl propanoic acid functionality. Suitably, the cyclohexyl, aryl, heterocyclic or heteroaryl groups of the mandelic acid functionality or the 3-hydroxy-3-phenyl propanoic acid functionality may be mono-, di-, tri- or tetra-substituted with substituents independently selected from the group consisting of: —H, hydroxy, $C_1$-$C_6$ alkyl, $C_1$-$C_6$ alkoxy, nitro, halo, acyl, phosphine ($PR_2$), diarylphosphine ($PAr_2$), phosphate, phosphite, sulfate, sulfite, phosphonamide, phosphinamide, sulfonamide, sulfonimide, sulfinamide, sulfinimide, carboxylic ester, carbonate and carbamate or wherein two adjacent substitutions which together form a $C_1$-$C_4$ alkylenedioxy ring, and wherein the heterocyclic or heteroaryl group comprises at least one heteroatom N, O or S. Preferred compounds are those having a chiral esterified hydroxy carboxylic acid functionality with a di-substituted cyclohexyl, aryl, heterocyclic or heteroaryl ring. Preferred ring di-substitutions include adjacent hydroxy, $C_1$-$C_6$ alkoxy substitutions or examples where the di substitutions form a 3,4 methylenedioxy ring structure The remaining position on the chiral alpha asymmetric carbon may be substituted with —OH, —$CF_3$, a cyclohexyl, an aryl, a heterocyclic, heteroaryl group, $C_1$-$C_6$ alkyl, a $C_1$-$C_6$ alkyl ether group, either of which may be branched or unbranched, and the alkyl ether group comprises at least one ether linkage in the alkyl chain; wherein the cyclohexyl, aryl, heterocyclic or heteroaryl groups may be mono-, di-, tri- or tetra-substituted with substituents independently selected from the group consisting of: —H, hydroxy, $C_1$-$C_6$ alkyl, $C_1$-$C_6$ alkoxy, nitro, halo, acyl, phosphine ($PR_2$), diarylphosphine ($PAr_2$), phosphate, phosphite, sulfate, sulfite, phosphonamide, phosphinamide, sulfonamide, sulfonimide, sulfinamide, sulfinimide, carboxylic ester, carbonate and carbamate or wherein two adjacent substitutions which together form a $C_1$-$C_4$ alkylenedioxy ring, and wherein the heterocyclic or heteroaryl group comprises at least one heteroatom N, O or S.

In a preferred embodiment, the compounds of the invention have general formula VI or VII

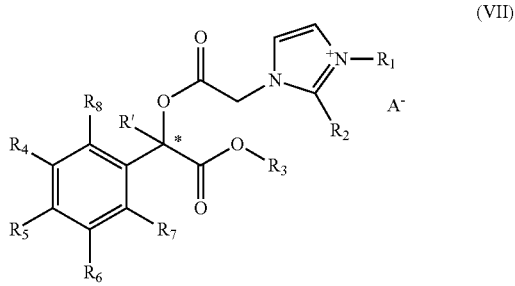

(VII)

-continued (VIII)

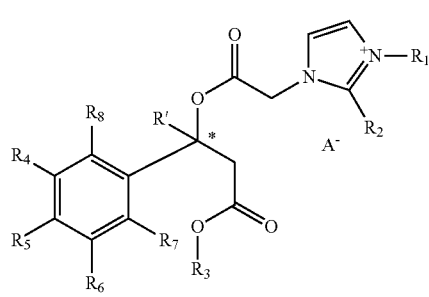

wherein $R^1$ is a $C_1$-$C_4$ alkyl or $C_1$-$C_4$ alkoxy;

$R^2$ is —H or a $C_1$-$C_4$ alkyl;

R' is —H, —OH, —CF$_3$, a cyclohexyl, an aryl, a heterocyclic, a heteroaryl group, a $C_1$-$C_6$ alkyl, a $C_1$-$C_6$ alkyl ether group, either of which may be branched or unbranched, and the alkyl ether group comprises at least one ether linkage in the alkyl chain, wherein the cyclohexyl, aryl, heterocyclic or heteroaryl groups may be mono-, di-, tri- or tetra-substituted with substituents independently selected from —H, hydroxy, $C_1$-$C_6$ alkyl, $C_1$-$C_6$ alkoxy, nitro, halo, acyl, phosphine (PR$_2$), diarylphosphine (PAr$_2$), phosphate, phosphite, sulfate, sulfite, phosphonamide, phosphinamide, sulfonamide, sulfonimide, sulfinamide, sulfinimide, carboxylic ester, carbonate, carbamate or wherein two adjacent substitutions which together form a $C_1$-$C_4$ alkylenedioxy ring, and wherein the heterocyclic or heteroaryl group comprising at least one heteroatom N, O or S, with the provision that R' is not simultaneously identical with the $R^4$, $R^5$ disubstituted aryl group;

$R^3$ is a $C_1$-$C_6$ alkyl, or a $C_1$-$C_6$ alkyl ether group, either of which may be branched or unbranched, and the alkyl ether group comprises at least one ether linkage in the alkyl chain; and $R^4$ $R^5$ $R^6$ $R^7$ and $R^8$ are independently from —H, hydroxy, $C_1$-$C_6$ alkyl, $C_1$-$C_6$ alkoxy, nitro, halo, acyl, phosphine (PR$_2$), diarylphosphine (PAr$_2$), phosphate, phosphite, sulfate, sulfite, phosphonamide, phosphinamide, sulfonamide, sulfonimide, sulfinamide, sulfinimide, carboxylic ester, carbonate, carbamate or two adjacent substitutions which together form a $C_1$-$C_4$ alkylenedioxy ring, A is OctOSO$_3$NTf$_2$ or N(CN)$_2$.

Suitably, the $C_1$-$C_6$ alkyl ether group may be —CH$_2$CH$_2$OCH$_3$, —CH$_2$CH$_2$OCH$_2$CH$_3$, —CH—$_2$CH$_2$OCH$_2$CH$_2$CH$_3$ or —CH$_2$CH$_2$OCH$_2$CH$_2$OCH$_2$CH$_3$. Branched alkyl ester analogues also fall within the scope of the invention.

In a particularly preferred embodiment, R' is —H.

In a preferred embodiment, the compounds of the invention have general formula IX or X -continued (X)

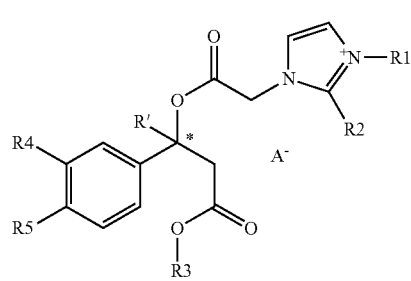

wherein $R^1$ is a $C_1$-$C_4$ alkyl or $C_1$-$C_4$ alkoxy;

$R^2$ is —H or a $C_1$-$C_4$ alkyl;

R' is —H, —OH, —CF$_3$, a cyclohexyl, an aryl, a heterocyclic, a heteroaryl group, a $C_1$-$C_6$ alkyl, a $C_1$-$C_6$ alkyl ether group, either of which may be branched or unbranched, and the alkyl ether group comprises at least one ether linkage in the alkyl chain, wherein the cyclohexyl, aryl, heterocyclic or heteroaryl groups may be mono-, di-, tri- or tetra-substituted with substituents independently selected from —H, hydroxy, $C_1$-$C_6$ alkyl, $C_1$-$C_6$ alkoxy, nitro, halo, acyl, phosphine (PR$_2$), diarylphosphine (PAr$_2$), phosphate, phosphite, sulfate, sulfite, phosphonamide, phosphinamide, sulfonamide, sulfonimide, sulfinamide, sulfinimide, carboxylic ester, carbonate, carbamate or wherein two adjacent substitutions which together form a $C_1$-$C_4$ alkylenedioxy ring, and wherein the heterocyclic or heteroaryl group comprising at least one heteroatom N, O or S, with the provision that R' is not simultaneously identical with the $R^4$, $R^5$ disubstituted aryl group;

$R^3$ is a $C_1$-$C_6$ alkyl, or a $C_1$-$C_6$ alkyl ether group, either of which may be branched or unbranched, and the alkyl ether group comprises at least one ether linkage in the alkyl chain; and $R^4$ and $R^5$ are independently from —H, hydroxy, $C_1$-$C_6$ alkyl, $C_1$-$C_6$ alkoxy, nitro, halo, acyl, phosphine (PR$_2$), diarylphosphine (PAr$_2$), phosphate, phosphite, sulfate, sulfite, phosphonamide, phosphinamide, sulfonamide, sulfonimide, sulfinamide, sulfinimide, carboxylic ester, carbonate, carbamate or two adjacent substitutions which together form a $C_1$-$C_4$ alkylenedioxy ring, A is OctOSO$_3$NTf$_2$ or N(CN)$_2$.

Suitably, the $C_1$-$C_6$ alkyl ether group may be —CH$_2$CH$_2$OCH$_3$, —CH$_2$CH$_2$OCH$_2$CH$_3$, —CH—$_2$CH$_2$OCH$_2$CH$_2$CH$_3$ or —CH$_2$CH$_2$OCH$_2$CH$_2$OCH$_2$CH$_3$. Branched alkyl ester analogues also fall within the scope of the invention.

In a particularly preferred embodiment, R' is —H.

In a preferred embodiment, the compounds of the invention have general formula IX or X (IX)

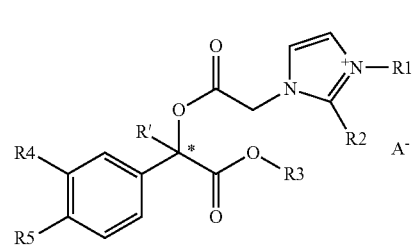

(IX)

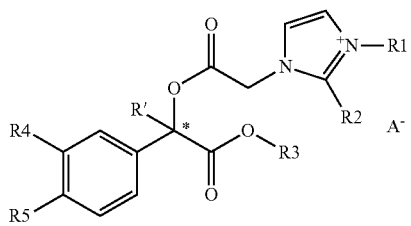

-continued

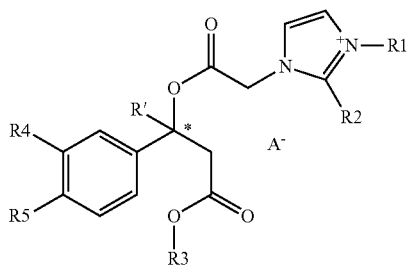
(X)

wherein R$^1$ is a C$_1$-C$_4$ alkyl;

R$^3$ is a C$_1$-C$_6$ alkyl or a C$_1$-C$_6$ alkyl ether group, either of which may be branched or unbranched, and the alkyl ether group comprises at least one ether linkage in the alkyl chain;

R$^4$ and R$^5$ are independently from hydrogen, hydroxy, C$_1$-C$_6$ alkyl, C$_1$-C$_6$ alkoxy, nitro, halo, acyl, phosphine (PR$_2$), diarylphosphine (PAr$_2$), phosphate, phosphite, sulfate, sulfite, phosphonamide, phosphinamide, sulfonamide, sulfonimide, sulfinamide, sulfinimide, carboxylic ester, carbonate, carbamate or two adjacent substitutions which together form a C$_1$-C$_4$ alkylenedioxy ring; and A is OctOSO$_3$, NTf$_2$ or N(CN)$_2$.

Suitably, the C$_1$-C$_6$ alkyl ether group may be —CH$_2$CH$_2$OCH$_3$, —CH$_2$CH$_2$OCH$_2$CH$_3$, —CH$_2$CH$_2$OCH$_2$CH$_2$CH$_3$ or —CH$_2$CH$_2$OCH$_2$CH$_2$OCH$_2$CH$_3$. Branched alkyl ester analogues also fall within the scope of the invention.

In a preferred embodiment, the compounds of the invention have general formula IX or X

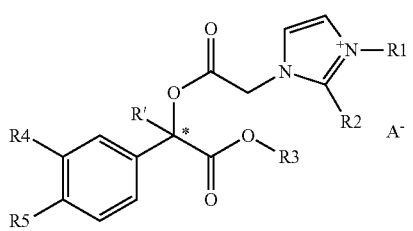
(IX)

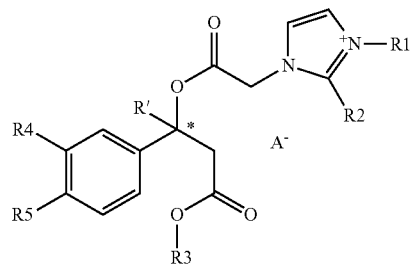
(X)

wherein R$^1$ is a C$_1$-C$_4$ alkyl;

R$^4$ and R$^5$ are independently —H, a C$_1$-C$_6$ alkyl, a C$_1$-C$_6$ alkoxy or together form a methylenedioxy ring;

R$^3$ is a C$_1$-C$_6$ alkyl, a C$_1$-C$_6$ alkyl ether group, either of which may be branched or unbranched, and the alkyl ether group comprises at least one ether linkage in the alkyl chain; and A is OctOSO$_3$ or NTf$_2$.

Suitably, the C$_1$-C$_6$ alkyl ether group may be —CH$_2$CH$_2$OCH$_3$, —CH$_2$CH$_2$OCH$_2$CH$_3$, —CH$_2$CH$_2$OCH$_2$CH$_2$CH$_3$ or —CH$_2$CH$_2$OCH$_2$CH$_2$OCH$_2$CH$_3$. Branched alkyl ester analogues also fall within the scope of the invention.

In a preferred embodiment, the compounds of the invention have general formula IX or X

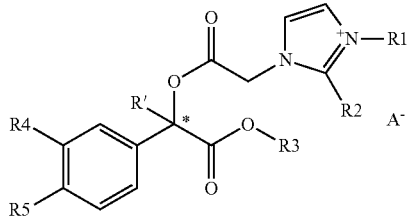
(IX)

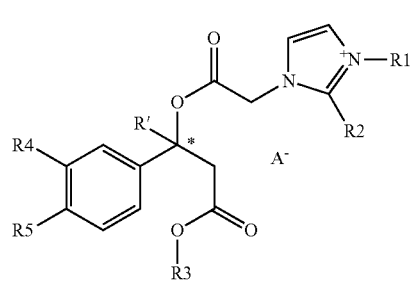
(X)

wherein R$^1$ is a C$_1$-C$_4$ alkyl;

R$^4$ and R$^5$ are independently —H, a C$_1$-C$_6$ alkyl, a C$_1$-C$_6$ alkoxy or together form a methylenedioxy ring;

R$^3$ is a C$_1$-C$_6$ alkyl; and

A is OctOSO$_3$ or NTf$_2$.

In one embodiment, the compounds of the invention comprising a chiral hydroxy carboxylic acid functionality having an aryl substituent on the asymmetric carbon (such as the mandelate based system), is considerably more versatile because the aromatic ring can be readily functionalised. Thus, the ionic liquids in the present invention allow convenient solvent tailoring.

These functionalised aromatic rings have a great deal of potential, either for hydrogen bonding (to catalyse reactions (e.g. Diels-Alder or aid chromatography), to bind metals (e.g. iron) or attach groups such as phosphoryl (with organocatalytic possibilities) and sulfonyl or to activate the aromatic ring to scavenge electrophiles, especially cations (e.g. in peptide deprotection from a solid support) or act as an anti-oxidant as a biodegradable alternative to Song's and Wang's electrophile-scavenging ILs. The possibility of forming separate phases, especially triphasic systems means that the CILs in the present invention present an alternative to expensive fluorous scavengers (Basle). Furthermore, the presence of electron-donating groups on the aromatic will make it easier to further functionalise the ring by electrophilic aromatic substitution, e.g. with nitro or halogens. Suitable substitutions have already been discussed earlier.

In a different preferred embodiment, the compounds of the invention comprise general formula XI, XII or XIII

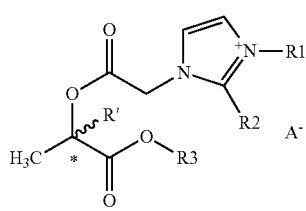
XI

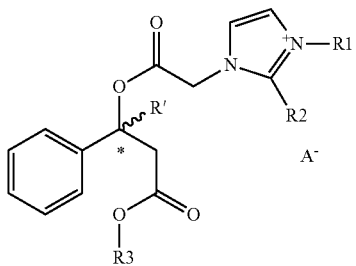

XII

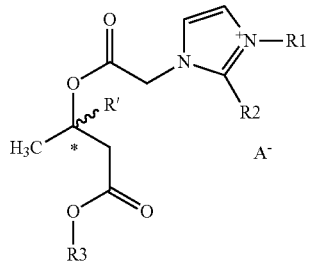

XIII wherein R$^1$ is a C$_1$-C$_4$ alkyl;

R$^2$ is a —H or a C$_1$-C$_4$ alkyl;

R' is —H, —OH, —CF$_3$, a cyclohexyl, an aryl, a heterocyclic, heteroaryl group, C$_1$-C$_6$ alkyl, a C$_1$-C$_6$ alkyl ether group, either of which may be branched or unbranched, and the alkyl ether group comprises at least one ether linkage in the alkyl chain;

wherein the cyclohexyl, aryl, heterocyclic or heteroaryl groups may be mono-, di-, tri or tetra-substituted with substituents independently selected from —H, hydroxy, C$_1$-C$_6$ alkyl, C$_1$-C$_6$ alkoxy, nitro, halo, acyl, phosphine (PR$_2$), diarylphosphine (PAr$_2$), phosphate, phosphite, sulfate, sulfite, phosphonamide, phosphinamide, sulfonamide, sulfonimide, sulfinamide, sulfinimide, carboxylic ester, carbonate, carbamate or wherein two adjacent substitutions which together form a C$_1$-C$_4$ alkylenedioxy ring, and wherein the heterocyclic or heteroaryl group comprising at least one heteroatom N, O or S;

R$^4$ and R$^5$ are independently —H, a C$_1$-C$_6$ alkyl, a C$_1$-C$_6$ alkoxy or together form a methylenedioxy ring;

R$^3$ is a C$_1$-C$_6$ alkyl, or a C$_1$-C$_6$ alkyl ether group, either of which may be branched or unbranched, and the alkyl ether group comprises at least one ether linkage in the alkyl chain, with the provision that R' is not simultaneously identical to a group attached to the asymmetric centre marked *; and A is OctOSO$_3$, NTf$_2$ or N(CN)$_2$.

Suitably, the C$_1$-C$_6$ alkyl ether group may be —CH$_2$CH$_2$OCH$_3$, —CH$_2$CH$_2$OCH$_2$CH$_3$, —CH—$_2$CH$_2$OCH$_2$CH$_2$CH$_3$ or —CH$_2$CH$_2$OCH$_2$CH$_2$OCH$_2$CH$_3$. Branched alkyl ester analogues also fall within the scope of the invention.

In a different preferred embodiment, the compounds of the invention comprise general formula XIV, XV or XVI

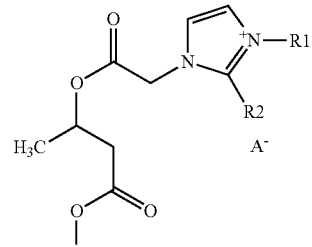

XIV

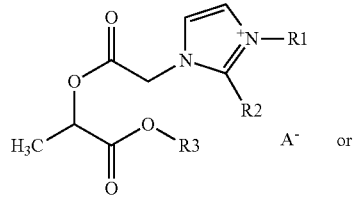

XV

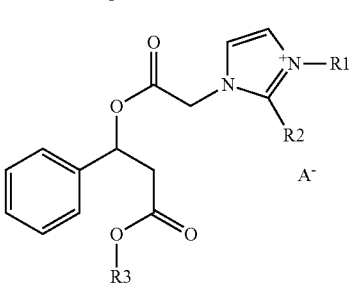

XVI wherein R$^1$ is a C$_1$-C$_4$ alkyl;

R$^2$ is a —H or a C$_1$-C$_4$ alkyl;

R$^3$ is a C$_1$-C$_6$ alkyl, or a C$_1$-C$_6$ alkyl ether group, either of which may be branched or unbranched, and the alkyl ether group comprises at least one ether linkage in the alkyl chain; and A is OctOSO$_3$ or NTf$_2$.

In a different preferred embodiment, the compounds of the invention comprise general formula XVII, XVIII or XIX

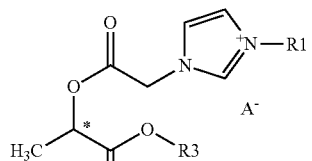

XVII

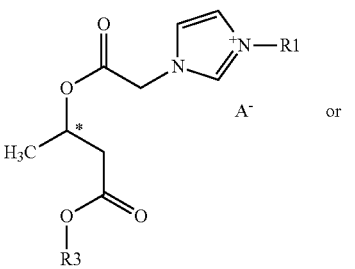

XVIII

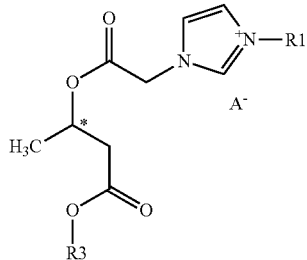

XIX

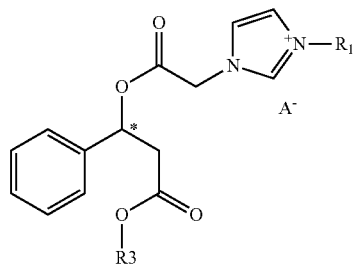

XIX wherein $R^1$ is a $C_1$-$C_4$ alkyl;

$R^3$ is a $C_1$-$C_6$ alkyl, or a $C_1$-$C_6$ alkyl ether group, either of which may be branched or unbranched and the alkyl ether group comprises at least one ether linkage in the alkyl chain; and A is $OctOSO_3$ or $NTf_2$.

Suitably, the $C_1$-$C_6$ alkyl ether group may be —$CH_2CH_2OCH_3$, —$CH_2CH_2OCH_2CH_3$, —$CH_2CH_2OCH_2CH_2CH_3$ or —$CH_2CH_2OCH_2CH_2OCH_2CH_3$. Branched alkyl ester analogues also fall within the scope of the invention.

In a different preferred embodiment, the compounds of the invention comprise general formula XVII, XVIII or XIX

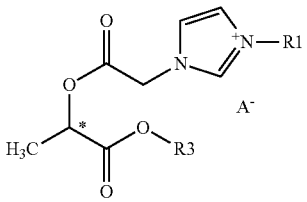

XVII

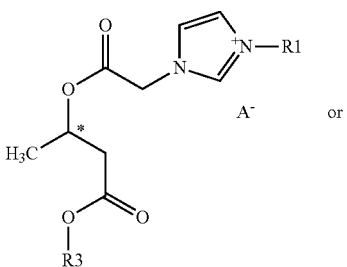

XVIII or

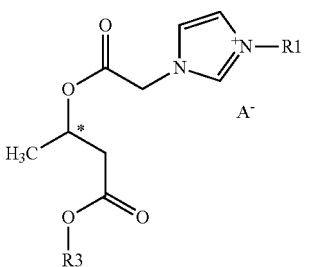

wherein $R^1$ is a $C_1$-$C_4$ alkyl;

$R^3$ is a $C_1$-$C_6$ alkyl; and

A is $OctOSO_3$ or $NTf_2$.

In the various embodiments of the invention described thus far, it is preferred that the chiral carboxylic acid functionality comprises an acid ester group which may be represented by —$COOR^3$, wherein $R^3$ is preferably a $C_1$-$C_6$ alkyl group or a $C_1$-$C_6$ alkyl ether group, either of which may be branched or unbranched, and the alkyl ether group comprises at least one ether linkage in the alkyl chain. Most preferred compounds of the invention comprise $C_1$-$C_6$ alkyl groups in $R_3$ position.

In the various embodiments described thus far, it is preferred that the alkyl substituent on the 1 position of the imidazolium ring is a methyl substituent or an ethyl substituent ($R^1$ is methyl or ethyl).

In the various embodiments described thus far, it is preferred that the alkyl substituent on the 2 position of the imidazolium ring is —H or a methyl substituent ($R^1$ is methyl).

In any of the embodiments described herein, the preferred compounds of the invention are those having a counter anion (A⁻) is $OctOSO_3$ or $NTf_2$. Particularly preferred compounds are those having anion A⁻ is $OctOSO_3$, since these compounds are all readily biodegradable, producing a score of at least 60% degradation over 28 days in the $CO_2$ Headspace Test. Compounds comprising $NTf_2$ are preferred, where CILs of lower viscosity are required.

Preferred CILs are from the following list:

| KG No. | Name |
| --- | --- |
| KG 86 | RS-3-methyl-1-[1-(methoxycarbonyl)-1-phenylmethoxycarbonylmethyl]imidazolium octyl sulphate |
| KG 87 | R-3-methyl-1-[1-(methoxycarbonyl)-1-phenylmethoxycarbonylmethyl]imidazolium octyl sulphate |
| KG 88 | S-3-methyl-1-[1-(methoxycarbonyl)-1-phenylmethoxycarbonylmethyl]imidazolium octyl sulphate |
| KG 89 | RS-3-methyl-1-[1-(methoxycarbonyl)-1-phenylmethoxycarbonylmethyl]imidazolium bromide |
| KG 90 | R-3-methyl-1-[1-(methoxycarbonyl)-1-phenylmethoxycarbonylmethyl]imidazolium bromide |
| KG 91 | S-3-methyl-1-[1-(methoxycarbonyl)-1-phenylmethoxycarbonylmethyl]imidazolium bromide |
| KG 92 | RS-3-methyl-1-[1-(methoxycarbonyl)-1-phenylmethoxycarbonylmethyl]imidazolium bis(trifluoromethanesulphonyl)imide |
| KG 93 | R-3-methyl-1-[1-(methoxycarbonyl)-1-phenylmethoxycarbonylmethyl]imidazolium bis(trifluoromethanesulphonyl)imide |
| KG 94 | S-3-methyl-1-[1-(methoxycarbonyl)-1-phenylmethoxycarbonylmethyl]imidazolium bis(trifluoromethanesulphonyl)imide |
| KG 150 | RS-3-methyl-1-[1-(methoxycarbonyl)-1-methylmethoxycarbonylmethyl]imidazolium bromide |
| KG 151 | R-3-methyl-1-[1-(methoxycarbonyl)-1-methylmethoxycarbonylmethyl]imidazolium bromide |
| KG 152 | RS-3-methyl-1-[1-(ethoxycarbonyl)-1-methylmethoxycarbonylmethyl]imidazolium bromide |
| KG 153 | R-3-methyl-1-[1-(ethoxycarbonyl)-1-methylmethoxycarbonylmethyl]imidazolium bromide |
| KG 154 | RS-3-methyl-1-[1-(propoxycarbonyl)-1-methylmethoxycarbonylmethyl]imidazolium bromide |
| KG 155 | R-3-methyl-1-[1-(propoxycarbonyl)-1-methylmethoxycarbonylmethyl]imidazolium bromide |

-continued

| KG No. | Name |
|---|---|
| KG 156 | RS-3-methyl-1-[1-(butoxycarbonyl)-1-methylmethoxycarbonylmethyl]imidazolium bromide |
| KG 157 | R-3-methyl-1-[1-(butoxycarbonyl)-1-methylmethoxycarbonylmethyl]imidazolium bromide |
| KG 158 | RS-3-methyl-1-[1-(pentoxycarbonyl)-1-methylmethoxycarbonylmethyl]imidazolium bromide |
| KG 159 | R-3-methyl-1-[1-(pentoxycarbonyl)-1-methylmethoxycarbonylmethyl]imidazolium bromide |
| KG 160 | RS-3-methyl-1-[1-(ethoxyethoxycarbonyl)-1-methylmethoxycarbonylmethyl]imidazolium bromide |
| KG 161 | R-3-methyl-1-[1-(ethoxyethoxycarbonyl)-1-methylmethoxycarbonylmethyl]imidazolium bromide |
| KG 162 | RS-3-methyl-1-[1-(methoxycarbonyl)-1-methylmethoxycarbonylmethyl]imidazolium octyl sulphate |
| KG 163 | R-3-methyl-1-[1-(methoxycarbonyl)-1-methylmethoxycarbonylmethyl]imidazolium octyl sulphate |
| KG 164 | RS-3-methyl-1-[1-(ethoxycarbonyl)-1-methylmethoxycarbonylmethyl]imidazolium octyl sulphate |
| KG 165 | R-3-methyl-1-[1-(ethoxycarbonyl)-1-methylmethoxycarbonylmethyl]imidazolium octyl sulphate |
| KG 166 | RS-3-methyl-1-[1-(propoxycarbonyl)-1-methylmethoxycarbonylmethyl]imidazolium octyl sulphate |
| KG 167 | R-3-methyl-1-[1-(propoxycarbonyl)-1-methylmethoxycarbonylmethyl]imidazolium octyl sulphate |
| KG 168 | RS-3-methyl-1-[1-(butoxycarbonyl)-1-methylmethoxycarbonylmethyl]imidazolium octyl sulphate |
| KG 169 | R-3-methyl-1-[1-(butoxycarbonyl)-1-methylmethoxycarbonylmethyl]imidazolium octyl sulphate |
| KG 170 | RS-3-methyl-1-[1-(pentoxycarbonyl)-1-methylmethoxycarbonylmethyl]imidazolium octyl sulphate |
| KG 171 | R-3-methyl-1-[1-(pentoxycarbonyl)-1-methylmethoxycarbonylmethyl]imidazolium octyl sulphate |
| KG 172 | RS-3-methyl-1-[1-(ethoxyethoxycarbonyl)-1-methylmethoxycarbonylmethyl]imidazolium octyl sulphate |
| KG 173 | R-3-methyl-1-[1-(ethoxyethoxycarbonyl)-1-methylmethoxycarbonylmethyl]imidazolium octyl sulphate |
| KG 300 | S-3-methyl-1-[1-(ethoxycarbonyl)-1-phenylmethoxycarbonylmethyl]imidazolium octyl sulphate |
| KG 301 | R-3-methyl-1-[1-(ethoxycarbonyl)-1-phenylmethoxycarbonylmethyl]imidazolium octyl sulphate |
| KG 302 | S-3-methyl-1-[1-(pentoxycarbonyl)-1-phenylmethoxycarbonylmethyl]imidazolium octyl sulphate |
| KG 303 | R-3-methyl-1-[1-(pentoxycarbonyl)-1-phenylmethoxycarbonylmethyl]imidazolium octyl sulphate |
| KG 304 | RS-3-methyl-1-[1-(pentoxycarbonyl)-1-phenylmethoxycarbonylmethyl]imidazolium octyl sulphate |
| KG 305 | S-3-methyl-1-[1-(ethoxyethoxycarbonyl)-1-phenylmethoxycarbonylmethyl]imidazolium octyl sulphate |
| KG 306 | S-3-methyl-1-[1-(butoxycarbonyl)-1-phenylmethoxycarbonylmethyl]imidazolium octyl sulphate |
| KG 307 | RS-3-methyl-1-[1-(ethoxycarbonyl)-1-phenylmethoxycarbonylmethyl]imidazolium octyl sulphate |
| KG 308 | RS-3-methy1-1-[1-(butoxycarbonyl)-1-phenylmethoxycarbonylmethyl]imidazolium octyl sulphate |
| KG 400 | RS-3-methyl-1-[1-(ethoxyethoxycarbonyl)-1-phenylmethoxycarbonylmethyl]imidazolium octyl sulphate |
| KG 401 | R-3-methyl-1-[1-(ethoxycarbonyl)-1-phenylmethoxycarbonylmethyl]imidazolium octyl sulphate |
| KG 800 | RS-3-methyl-1-[1-(methoxycarbonyl)-1-methylmethoxycarbonylmethyl]imidazolium bis(trifluoromethanesulphonyl)imide |
| KG 801 | RS-3-methyl-1-[1-(ethoxycarbonyl)-1-methylmethoxycarbonylmethyl]imidazolium bis(trifluoromethanesulphonyl)imide |
| KG 802 | RS-3-methyl-1-[1-(propoxycarbonyl)-1-methylmethoxycarbonylmethyl]imidazolium bis(trifluoromethanesulphonyl)imide |
| KG 803 | RS-3-methyl-1-[1-(butoxycarbonyl)-1-methylmethoxycarbonylmethyl]imidazolium bis(trifluoromethanesulphonyl)imide |
| KG 804 | RS-3-methyl-1-[1-(pentoxycarbonyl)-1-methylmethoxycarbonylmethyl]imidazolium bis(trifluoromethanesulphonyl)imide |
| KG 805 | RS-3-methyl-1-[1-(ethoxyethoxycarbonyl)-1-methylmethoxycarbonylmethyl]imidazolium bis(trifluoromethanesulphonyl)imide |
| KG 806 | R-3-methyl-1-[1-(methoxycarbonyl)-1-methylmethoxycarbonylmethyl]imidazolium bis(trifluoromethanesulphonyl)imide |
| KG 807 | R-3-methyl-1-[1-(ethoxycarbonyl)-1-methylmethoxycarbonylmethyl]imidazolium bis(trifluoromethanesulphonyl)imide |
| KG 808 | R-3-methyl-1-[1-(propoxycarbonyl)-1-methylmethoxycarbonylmethyl]imidazolium bis(trifluoromethanesulphonyl)imide |
| KG 809 | R-3-methyl-1-[1-(butoxycarbonyl)-1-methylmethoxycarbonylmethyl]imidazolium bis(trifluoromethanesulphonyl)imide |
| KG 810 | R-3-methyl-1-[1-(pentoxycarbonyl)-1-methylmethoxycarbonylmethyl]imidazolium bis(trifluoromethanesulphonyl)imide |
| KG 811 | R-3-methyl-1-[1-(ethoxyethoxycarbonyl)-1-methylmethoxycarbonylmethyl]imidazolium bis(trifluoromethanesulphonyl)imide |
| KG 812 | RS-3-methyl-1-[1-(ethoxycarbonyl)-1-phenylmethoxycarbonylmethyl]imidazolium bromide |
| KG 813 | RS-3-methyl-1-[1-(ethoxycarbonyl)-1-phenylmethoxycarbonylmethyl]imidazolium bis(trifluoromethanesulphonyl)imide |
| KG 814 | RS-3-methyl-1-[1-(butoxycarbonyl)-1-phenylmethoxycarbonylmethyl]imidazolium bromide |
| KG 815 | RS-3-methyl-1-[1-(butoxycarbonyl)-1-phenylmethoxycarbonylmethyl]imidazolium bis(trifluoromethanesulphonyl)imide |
| KG 816 | RS-3-methyl-1-[1-(pentoxycarbonyl)-1-phenylmethoxycarbonylmethyl]imidazolium bromide |
| KG 817 | RS-3-methyl-1-[1-(pentoxycarbonyl)-1-phenylmethoxycarbonylmethyl]imidazolium bis(trifluoromethanesulphonyl)imide |
| KG 818 | RS-3-methyl-1-[1-(ethoxyethoxycarbonyl)-1-phenylmethoxycarbonylmethyl]imidazolium bromide |
| KG 819 | RS-3-methyl-1-[1-(ethoxyethoxycarbonyl)-1-phenylmethoxycarbonylmethyl]imidazolium bis(trifluoromethanesulphonyl)imide |
| KG 820 | S-3-methyl-1-[1-(ethoxycarbonyl)-1-phenylmethoxycarbonylmethyl]imidazolium bromide |
| KG 821 | S-3-methyl-1-[1-(ethoxycarbonyl)-1-phenylmethoxycarbonylmethyl]imidazolium bis(trifluoromethanesulphonyl)imide |
| KG 822 | S-3-methyl-1-[1-(butoxycarbonyl)-1-phenylmethoxycarbonylmethyl]imidazolium bromide |
| KG 823 | S-3-methyl-1-[1-(butoxycarbonyl)-1-phenylmethoxycarbonylmethyl]imidazolium bis(trifluoromethanesulphonyl)imide |
| KG 824 | S-3-methyl-1-[1-(pentoxycarbonyl)-1-phenylmethoxycarbonylmethyl]imidazolium bromide |
| KG 825 | S-3-methyl-1-[1-(pentoxycarbonyl)-1-phenylmethoxycarbonylmethyl]imidazolium bis(trifluoromethanesulphonyl)imide |
| KG 826 | S-3-methyl-1-[1-(ethoxyethoxycarbonyl)-1-phenylmethoxycarbonylmethyl]imidazolium bromide |
| KG 827 | S-3-methyl-1-[1-(ethoxyethoxycarbonyl)-1-phenylmethoxycarbonylmethyl]imidazolium bis(trifluoromethanesulphonyl)imide |

-continued

| KG No. | Name |
|---|---|
| KG 828 | R-3-methyl-1-[1-(ethoxycarbonyl)-1-phenylmethoxycarbonylmethyl]imidazolium bromide |
| KG 829 | R-3-methyl-1-[1-(ethoxycarbonyl)-1-phenylmethoxycarbonylmethyl]imidazolium bis(trifluoromethanesulphonyl)imide |
| KG 830 | R-3-methyl-1-[1-(butoxycarbonyl)-1-phenylmethoxycarbonylmethyl]imidazolium bromide |
| KG 831 | R-3-methyl-1-[1-(butoxycarbonyl)-1-phenylmethoxycarbonylmethyl]imidazolium bis(trifluoromethanesulphonyl)imide |
| KG 832 | R-3-methyl-1-[1-(butoxycarbonyl)-1-phenylmethoxycarbonylmethyl]imidazolium octyl sulphate |
| KG 833 | R-3-methyl-1-[1-(pentoxycarbonyl)-1-phenylmethoxycarbonylmethyl]imidazolium bromide |
| KG 834 | R-3-methyl-1-[1-(pentoxycarbonyl)-1-phenylmethoxycarbonylmethyl]imidazolium bis(trifluoromethanesulphonyl)imide |
| KG 835 | R-3-methyl-1-[1-(ethoxyethoxycarbonyl)-1-phenylmethoxycarbonylmethyl]imidazolium bromide |
| KG 836 | R-3-methyl-1-[1-(ethoxyethoxycarbonyl)-1-phenylmethoxycarbonylmethyl]imidazolium bis(trifluoromethanesulphonyl)imide |
| KG 1020 | RS-2-(3,4-methylendioxyphenyl)-2-(3-methylimidazolium) butyl acetate bromide salt |
| KG 1022 | RS-3-methyl-1-[1-(butoxycarbonyl)-1-(3,4-methylenedioxyphenyl)methoxycarbonylmethyl]imidazolium bromide |
| KG 1025 | RS-2-(3,4-dihydroxyphenyl)-2-(3-methylimidazolium) methyl acetate chloride salt |
| KG 1026 | RS-3-methyl-1-[1-(butoxycarbonyl)-1-(3,4-methylenedioxyphenyl)methoxycarbonylmethyl]imidazolium octyl sulphate |
| KG 1027 | RS-3-butyl-1-[1-(butoxycarbonyl)-1-(3,4-methylenedioxyphenyl)methoxycarbonylmethyl]imidazolium bromide |
| KG 1029 | RS-3-methyl-1-[1-(butoxycarbonyl)-1-(3,4-methylenedioxyphenyl)methoxycarbonylmethyl]imidazolium bis(trifluoromethanesulphonyl)imide |
| KG 1034 | RS-3-methyl-1-[1-(methoxycarbonyl)-1-(4-bromophenyl)methoxycarbonylmethyl]imidazolium bromide |
| KG 1035 | RS-3-methyl-1-[1-(methoxycarbonyl)-1-(4-trifluoromethylphenyl)methoxycarbonylmethyl]imidazolium bromide |
| KG 1036 | RS-3-methyl-1-[1-(methoxycarbonyl)-1-(4-methoxyphenyl)methoxycarbonylmethyl]imidazolium bromide |
| KG 1037 | RS-3-butyl-1-[1-(butoxycarbonyl)-1-(3,4-methylenedioxyphenyl)methoxycarbonylmethyl]imidazolium bis(trifluoromethanesulphonyl)imide |
| KG 1038 | RS-3-butyl-1-[1-(butoxycarbonyl)-1-(3,4-methylenedioxyphenyl)methoxycarbonylmethyl]imidazolium octyl sulphate |
| KG 1039 | RS-3-methyl-1-[1-(methoxycarbonyl)-1-(4-methoxyphenyl)methoxycarbonylmethyl]imidazolium bis(trifluoromethanesulphonyl)imide |
| KG 1040 | RS-3-methyl-1-[1-(methoxycarbonyl)-1-(4-trifluoromethylphenyl)methoxycarbonylmethyl]imidazolium bis(trifluoromethanesulphonyl)imide |
| KG 1041 | RS-2-(3,4-dihydroxyphenyl)-2-(3-methylimidazolium) methyl acetate bromide salt |
| KG 1042 | RS-2-(3,4-dihydroxyphenyl)-2-(3-methylimidazolium) methyl acetate octyl sulphate salt |
| KG 1043 | RS-[1-(butoxycarbonyl)-1-(3,4-methylenedioxyphenyl)methoxycarbonylmethyl]pyridinium bromide |
| KG 1044 | RS-3-methyl-1-[1-(methoxycarbonyl)-1-(4-methoxyphenyl)methoxycarbonylmethyl]imidazolium octyl sulphate |
| KG 1045 | RS-[1-(butoxycarbonyl)-1-(3,4-methylenedioxyphenyl)methoxycarbonylmethyl]pyridinium octyl sulphate |
| KG 1046 | RS-[1-(butoxycarbonyl)-1-(3,4-methylenedioxyphenyl)methoxycarbonylmethyl]pyridinium bis(trifluoromethanesulphonyl)imide |
| KG 1047 | RS-3-methyl-1-[1-(methoxycarbonyl)-1-(4-trifluoromethylphenyl)methoxycarbonylmethyl]imidazolium octyl sulphate |
| KG 2000 | RS-2-(3,4-dimethoxyphenyl)-2-(3-methylimidazolium) methyl acetate, chloride salt |
| KG 2001 | RS-2-(3,4-dimethoxyphenyl)-2-(3-methylimidazolium) methyl acetate, octylsulphate salt |
| KG 2002 | RS-2-(3,4-dimethoxyphenyl)-2-(3-methylimidazolium) methyl acetate, bis(trifluoromethanesulphonyl)imide salt |
| KG 2003 | RS-2-(3,4-dimethoxyphenyl)-2-(3-methylimidazolium) butyl acetate, chloride salt |
| KG2004 | RS-2-(3,4-dimethoxyphenyl)-2-(3-methylimidazolium) butyl acetate, octylsulphate salt |
| KG2005 | RS-2-(3,4-dimethoxyphenyl)-2-(3-methylimidazolium) butyl acetate, bis(trifluoromethanesulphonyl)imide salt |
| KG2006 | RS-2-(3,4-methylendioxyphenyl)-2-(3-methylimidazolium) methyl acetate, chloride salt |
| KG2007 | RS-2-(3,4-methylendioxyphenyl)-2-(3-methylimidazolium) methyl acetate, octylsulphate salt |
| KG2008 | RS-2-(3,4-methylendioxyphenyl)-2-(3-methylimidazolium) methyl acetate, bis(trifluoromethanesulphonyl)imide salt |
| KG 2011 | RS-3-methyl-1-[1-(methoxycarbonyl)-1-(3,4-methylenedioxyphenyl)methoxycarbonylmethyl]imidazolium chloride |
| KG2012 | RS-2-(3,4-dihydroxyphenyl)-2-(3-methylimidazolium) methyl acetate, chloride salt |
| KG2013 | RS-2-(3,4-dimethoxyphenyl)-2-(pyridinium) methyl acetate, chloride salt |
| KG2014 | RS-2-(3,4-dimethoxyphenyl)-2-(pyridinium) methyl acetate, octylsulphate salt |
| KG2015 | RS-2-(3,4-methylendioxyphenyl)-2-(pyridinium) methyl acetate, bromide salt |
| KG2016 | RS-[1-(methoxycarbonyl)-1-(3,4-methylenedioxyphenyl)methoxycarbonylmethyl]pyridinium bromide |
| KG 2017 | S-3-methyl-1-[1-(methoxycarbonyl)-1-methylmethoxycarbonylmethyl]imidazolium bromide |
| KG 2018 | S-3-methyl-1-[1-(methoxycarbonyl)-1-methylmethoxycarbonylmethyl]imidazolium bis(trifluoromethanesulphonyl)imide |

Particularly preferred lactate based CILs having the counter anion OctOSO$_3^-$ are those selected from the group comprising:

KG162, (RS) 3-Methyl-1-(1-methyl-1-methoxycarbonyl)methylimidazolium octylsulfate.

KG163, (R) 3-Methyl-1-(1-methyl-1-methoxycarbonyl)methylimidazolium octylsulfate, KG166, (RS) 3-Methyl-1-(1-methyl-1-propoxycarbonyl)methylimidazolium octylsulfate, KG167, (R) 3-Methyl-1-(1-methyl-1-propoxycarbonyl)methylimidazolium octylsulfate, KG170, (RS) 3-Methyl-1-(1-methyl-1-pentoxycarbonyl)methylimidazolium octylsulfate, KG171, (R) 3-Methyl-1-(1-methyl-1-pentoxycarbonyl)methylimidazolium octylsulfate, KG172, (RS) 3-Methyl-1-(1-methyl-1-(2-ethoxyethoxy)carbonyl)methylimidazolium octylsulfate and KG173 (R) 3-Methyl-1-(1-methyl-1-(2-ethoxyethoxy)carbonyl)methylimidazolium octylsulfate.

Particularly preferred mandelate based CILs having the counter anion OctOSO$_3^-$ are those selected from the group consisting of:

KG301, (R) 3-Methyl-1-(1-phenyl-1-(2-ethoxyethoxy)carbonyl)methylimidazolium octylsulfate, KG302, (S) 3-Methyl-1-(1-phenyl-1-pentoxycarbonyl)methylimidazolium octylsulfate, KG303, (R) 3-Methyl-1-(1-phenyl-1-pentoxycarbonyl)methylimidazolium octylsulfate, KG304, (RS) 3-Methyl-1-(1-phenyl-1-pentoxycarbonyl)methylimidazolium octylsulfate, KG305, (S) 3-Methyl-1-(1-phenyl-1-(2-ethoxyethoxy)carbonyl)methylimidazolium octylsulfate, KG306, (S) 3-Methyl-1-(1-phenyl-1-butoxycarbonyl)methylimidazolium octylsulfate and KG308, (RS) 3-Methyl-1-(1-phenyl-1-butoxycarbonyl)methylimidazolium octylsulfate.

In a related aspect of the present invention a compound of the invention may be used as an ionic liquid. In one embodiment, there is provided an ionic liquid composition comprising at least one of the compounds of the invention described herein. In a preferred embodiment, the compounds of the invention as described herein may be used as an ionic liquid solvent.

Particularly preferred is use in a process selected from the group consisting of a chemical reaction, a biomass dissolution and a biofuel preparation. Where use is in biomass dissolution, then it is preferred that the biomass dissolution is a cellulose dilution.

In a preferred embodiment, the compounds of the invention may be used as a solvent or a co-solvent, a catalyst or a co-catalyst, or electrolyte in a solar cell for the purpose of solar energy conversion.

In a preferred embodiment, the CIL compounds may be mixed with at least one achiral ILs in any ratio desired and may award favourable properties on the mixture when used as a solvent with regards to reaction stereoinduction, selectivity and/or conversion.

In a preferred embodiment still, the chiral ionic liquids compounds of the invention may be used as a solvent or a co-solvent, a catalyst or a co-catalyst for a chemical reaction, the reaction being selected from the group consisting of enzymatic and biocatalytic reactions, organocatalytic reactions, neutralizations, acidifications, basifications, oxidations, reductions, hydrogenation reactions, radical reactions, electrophilic additions, electrophilic substitutions, nucleophilic additions, nucleophilic substitutions, rearrangements, pericyclic reactions, metathesis reactions and reduction of an aromatic system. Particularly preferred are hydrogenation reactions, such as olefin hydrogenation reactions and reactions involving the reduction of an aromatic system.

Pericyclic reactions include Diels-Alder and Ene reactions. Organocatalytic reactions include Mannich, aza-Mannich and aldol reactions.

Thus the compounds of the invention are advantageous since they are alternative green solvents which may be used in organic reactions, such as hydrogenation reactions. Of particular interest are CILs of the invention, which may be used in hydrogenation of compounds such as trans-cinnamaldehyde or benzyl cinnamate using the commercially available Pd/C catalyst and which will allow superior control of the reactant conversion and product selectivity.

In an embodiment involving hydrogenation reactions, the hydrogenation reaction may be carried out homogenously or heterogeneously.

In an embodiment where the hydrogenation reaction is carried out heterogeneously, the heterogenous hydrogenation may carried out in the presence of hydrogen gas and palladium supported on carbon or in the presence of hydrogen gas and platinum supported on carbon.

On the other hand where the hydrogenation reaction is carried out homogeneously, the hydrogenation reaction may be carried out in the presence of Wilkinson's catalyst, (NB Adams' catalyst is heterogeneous) a Taniaphos SL-T001-1/bis(norbornadiene)rhodium(I) tetrafluoroborate system or Rh DiPAMP-based chiral catalysts. In an alternative preferred embodiment, the hydrogenation reaction is the selective reduction of any of Z-methyl-α-(N-acetamido) cinnamate, dimethyl itaconate, tiglic acid, α-acetamido cinnamic acid, α-methyl-trans-cinnamaldehyde or α-acetamido acrylate substrates.

In a preferred hydrogenation reaction, the compounds of the invention are used as CILs in the selective reduction of the alkene bond of α-acetamido acrylate substrates using Rh DiPAMP-based chiral catalysts. In a preferred hydrogenation reaction, the compounds of the invention are used as CILs in the selective reduction of the alkene bond conjugated to the carbonyl group of benzyl cinnamate using hydrogen gas and palladium supported on carbon.

In a particularly preferred embodiment, the CIL used is a mandelate based IL, used as an additive with an achiral IL in the homogenous hydrogenation of an olefin substrate. In this type of reaction the preferred substrate is dimethyl itaconate.

In an embodiment involving reduction of an aromatic system, it is preferred that the reaction is carried out under 1 atmosphere of hydrogen using a Taniaphos catalyst system or a Rh DiPAMP-based catalyst system. In this embodiment, it is preferred that the aromatic system to be reduced is that of a substrate such as Z-methyl-α-(N-acetamido) cinnamate. In this system, advantageously, asymmetry is induced in the products.

Alternative preferred reactions, in which the compounds of the invention may be suitably used as CILs, include metathesis reactions and pericyclic reactions.

In a related aspect of the invention, the compounds described herein may be used as a chiral reagent in asymmetric synthesis. In particular, it is preferred that such chiral reagents are used in reactions involving the substrate Z-methyl-α-(N-acetamido) cinnamate.

In a further related aspect, the compounds may be used as a chromatographic separation reagent. Preferably, with regard to this aspect, in a preferred embodiment, the chromatographic separation reagent may be used as a stationary phase. Such stationary phase may be suitably used in an SPE column, a HPLC column, a GC column, a TLC plate or on a HPTLC plate.

Alternatively, the compounds may be added to mobile phase for use with chromatographic stationary phases.

Examples of CILs either as racemic mixtures, or single enantiomers have been prepared. CILs incorporating mandelic acid have been prepared as racemic mixtures, or the R or S enantiomer. A synthetic route that does not led to epimerisation of the chiral centre can be used for the stereoselective synthesis of a CIL, if demonstrated to be successful for the preparation of the racemate. Starting from the optically pure alpha-hydroxycarboxylic acid, either enantiomer of the CIL can be prepared.

For synthetic routes where epimerisation may occur (e.g. nucleophilic substitution alpha to aryl and carboxylic groups), chiral resolution of the racemic mixture will be required to obtain the optically pure chiral ionic liquid. Chiral resolution via crystallization of diastereomeric salts, or via enzymatic methods, or via chiral HPLC methods are preferred.

BRIEF DESCRIPTION OF THE DRAWINGS

FIG. 9: Synthetic route to KG 2000-2002;
FIG. 10: Synthetic route to KG 2003-2005;
FIG. 11: Synthetic Route to KG 2006-2008
and
FIG. 12: Synthesis of 3,4-dimethoxy methyl mandelate based ionic liquid KG 2013-2014.

DETAILED DESCRIPTION OF THE INVENTION

Ionic liquids based on chiral alpha hydroxy carboxylic (mandelic 1 and lactic 2) acids were prepared by acylating the free hydroxyl group of an ester of the chiral carboxylic acid with bromoacetyl bromide and then in the next step reacting the bromoalkyl linker with 3-N-methylimidazole or pyridine to give a chiral bromide salt. The bromide may then be exchanged with various counter ions such as ditriflimide, octylsulfate and dicyanoamide to give ionic liquids. The octyl sulphate imidazolium chiral ionic liquids tested to date are biodegradable and have low antimicrobial and antifungal toxicity. The octyl sulphate pyridinium chiral ionic liquids tested to date have low antimicrobial and antifungal toxicity and are expected to have good biodegradability. $NTf_2$ chiral ionic liquids have lower viscosity.

Figure 4:
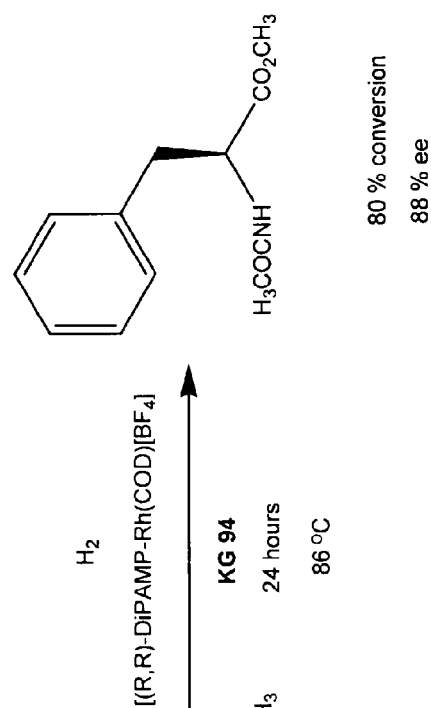
FIG. 4: Hydrogenation of Methyl α-acetoamidocinnamate in CIL derived from (S)-methyl mandelate as $NTf_2$ salt [KG 94]
Figure 4:
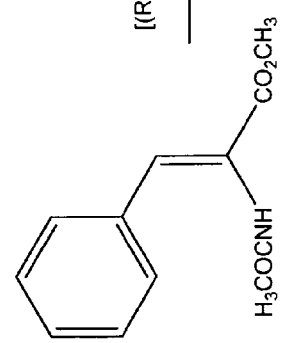

Novel chiral ILs based on chiral carboxylic acids, such as, mandelic 1 and lactic acids 2 have been investigated as solvents for organic transformations, such as, for the hydrogenation of olefins (a green process of major importance to the pharmaceutical industry, especially in asymmetric processes) including prochiral examples, such as (Z) methyl-α-(N-acetamido) cinnamate (FIG. 4). Diels-Alder, Ene reactions, and other pericyclic processes are also potential applications for the CILs described, as are organocatalytic reactions, such as Mannich, aza-Mannich, and aldol reactions, such that they are compatible with the ester linkages in the CILs. A variety of side-chains have been incorporated into the ILs (including both glycol ethers and alkyl groups) and both racemic and enantiopure mandelic and lactic acid were used as precursors for the Ils (FIG. 1). 2-Phase systems were demonstrated between the ILs and solvents such as toluene and ether, but interestingly a triphasic system was found to form between methylimidazolium mandelic acid derived IL 1 (racemic CIL, butyl ester/ditriflimide anion), water and toluene, which can provide advantages in reactions and also in separation science if products can be partitioned between the 3 phases preferentially (providing an alternative to 3-phases systems based on fluorous solvents such as the environmentally hazardous benzotrifluoride (trifluorotoluene) (D. P. Curran).

The synthesis of a new library of functionalised mandelate CILs (see table M, KG 837-884, for a specific example, see data provided for KG 852) with the potential to interact with metals or catalysts via oxygen substituents on the aromatic ring (FIG. 2) was undertaken. By varying R (methyl, butyl, hydrogen, phosphine), $R^1$ (methyl, butyl), $R^2$ (methyl, butyl) and X ($OctOSO_3$, $NTf_2$, $N(CN)_2$), a large library of new chiral ionic liquids with different properties is now available. The compounds 3,4-dihydroxymandelic acid and butyl 3,4-dimethoxymandelate 3 were synthesized by the inventors and together with commercially-available 3,4-methylenedioxymandelic 4 acid (FIG. 3) and derivates of same mean that these synthetic derivatives are suitable intermediates to expand the CIL library.

Detailed Experimental Methods

Preparation of ILs

Figure 6:
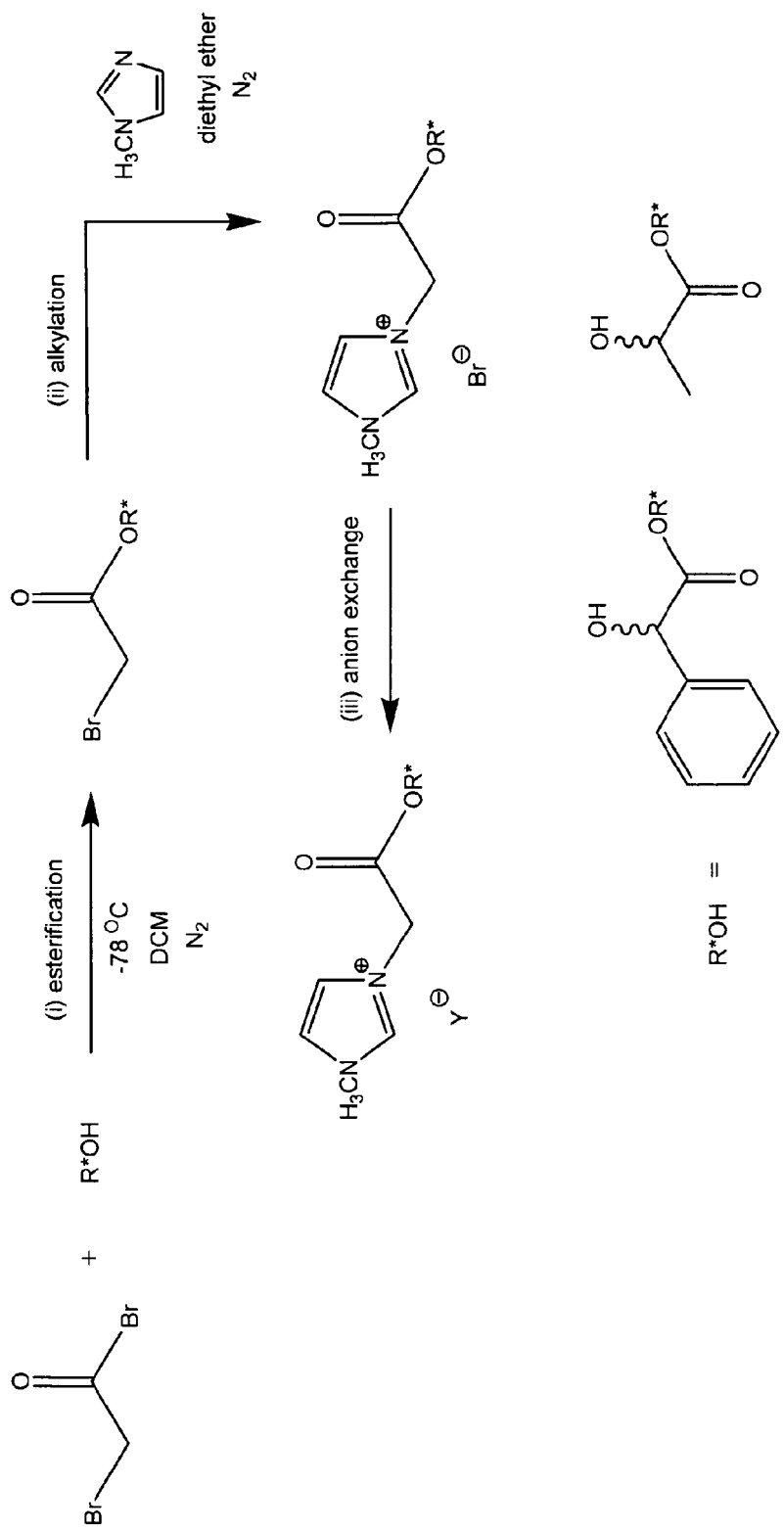
FIG. 6: Synthetic Route to CILs.
Figure 7:
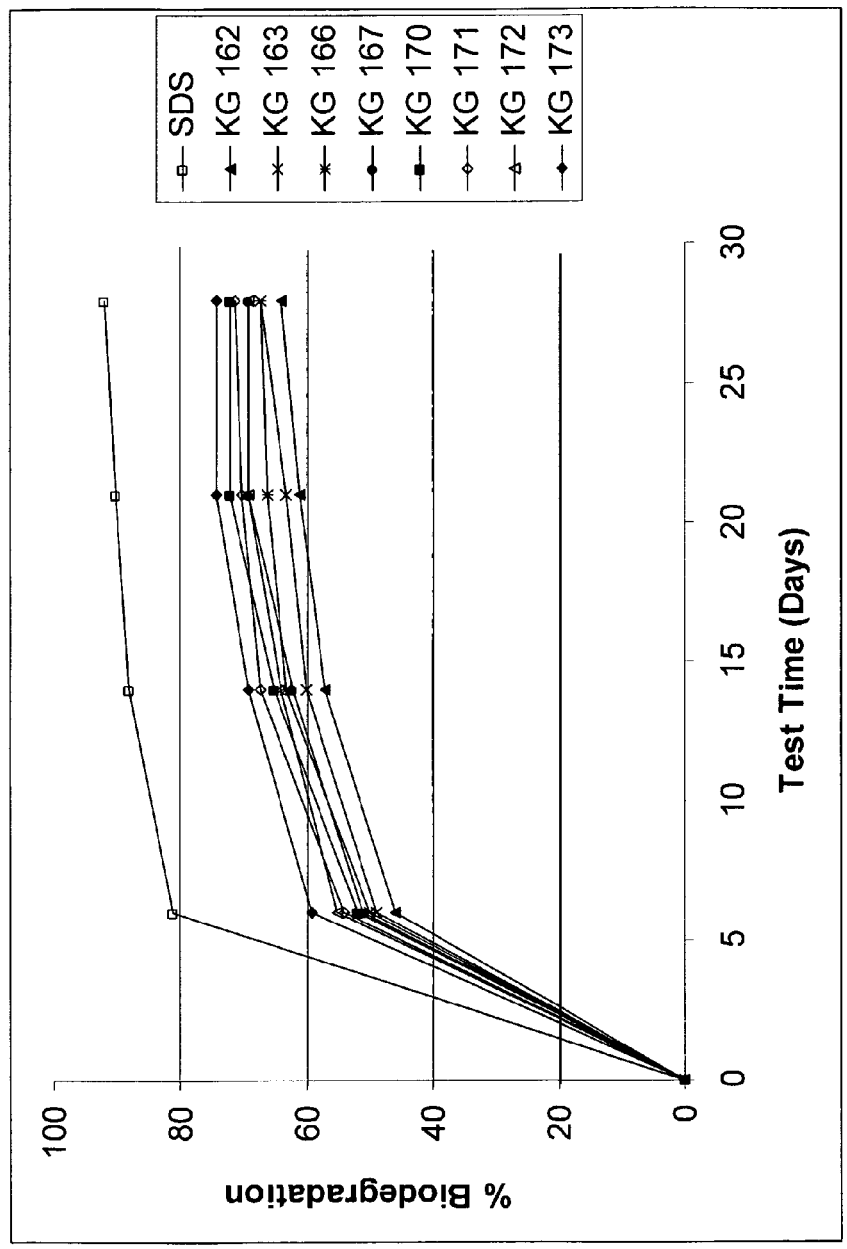
FIG. 7: Graphical Representation of Biodegradation of Chiral Lactate-derived Octylsulfates ($CO_2$ Headspace Test) over the Course of 28 days (Sodium dodecylsulfate [SDS] is taken as a reference compound)
Figure 8:
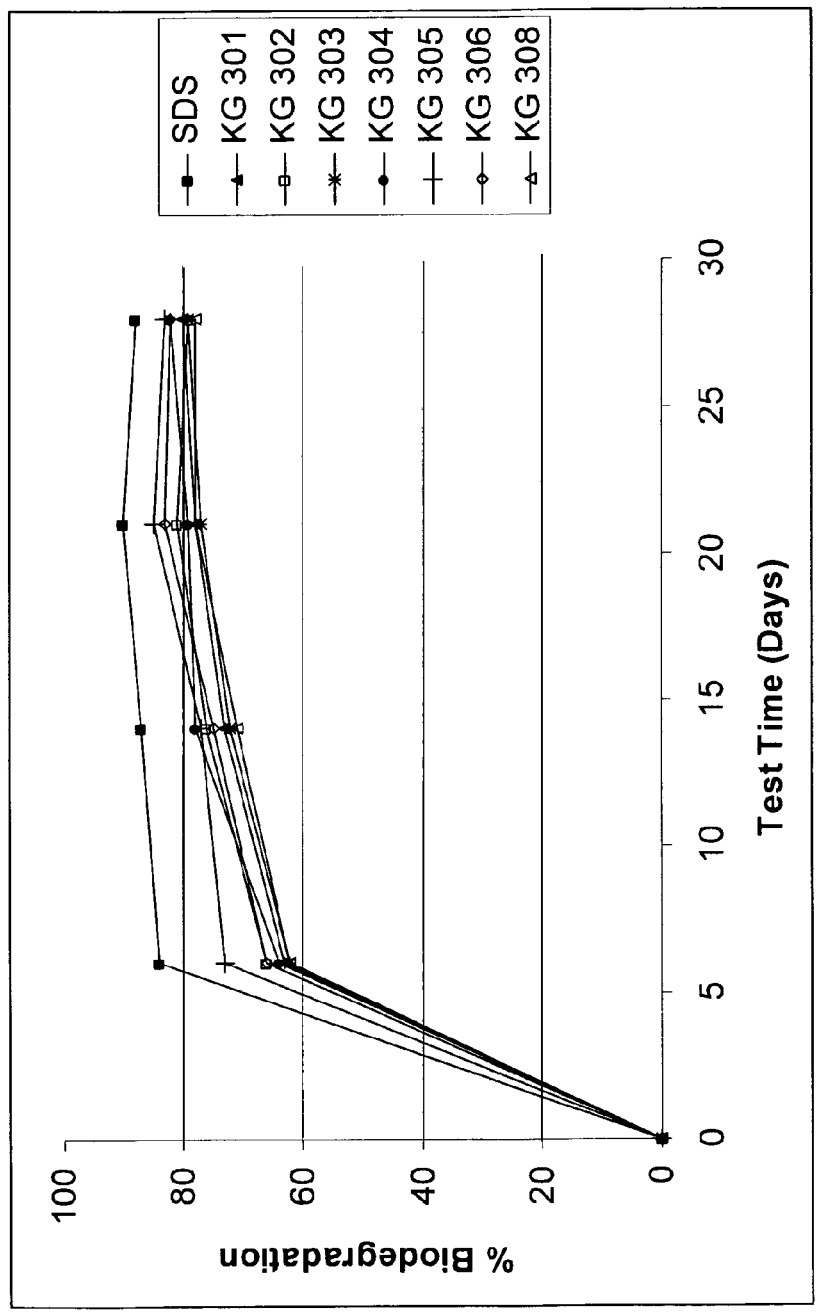
FIG. 8: Graphical Representation of Biodegradation of Chiral Mandelate-derived Octylsulfates ($CO_2$ Headspace Test) over the Course of 28 days (Sodium dodecylsulfate [SDS] is taken as a reference compound)

A simple method to synthesize the family of ionic liquids has been developed which produced the ILs in good yield for each step. A typical reaction scheme for synthesis of the chiral ILs is shown in FIG. 6. Referring to FIG. 6, in cases where the chiral centre in the IL is prone to racemisation under basic conditions, the alumina-catalysed esterification of Yadav, at room temperature, is preferred for the first step (esterification), rather than the use of triethylamine in DCM at −78° C. In brief, a bromoester alkylating agent is made from the chiral alcohol of interest (ILs with amide side chains or ILs with thioester side chains can be typically prepared by use of a haloamide or halothioester alkylating agent respectively). The bromoester is then reacted with the imidazole or pyridine of interest to form the imidazolium bromide salt or pyridinium bromide salt respectively. Preparation of alkylating reagents where the alcohol group of the alpha-hydroxyester has been converted to a chloride, was accomplished via treatment with thionyl chloride. Nucleophilic substitution by the imidazole or pyridine of interest leads to imidazolium chloride salt or pyridinium chloride salt respectively. An alternative one-pot method has been developed where the alcohol group of the mandelic acid ester is converted to the halide, via thionyl bromide or thionyl chloride, in the presence of the Nitrogen heterocycle (methylimidazole). The imidazolium halide salts were isolated in good yield by this one pot method. A large range of these types of ILs, possessing different properties have been made through the final synthetic anion exchange step from halide to different salts by reaction with $LiNTf_2$, or $NaOctOSO_3$.

Step I: Preparation of Alkylating Agent

Typically, the first step (i) is the preparation of the alkylating agent obtained by reaction between the bromoacetyl bromide and different alcohols, amines or thiols. The reaction involving bromoacetyl bromide and alcohols was performed under a nitrogen atmosphere at −78° C. for 3 hours. After purification by distillation the corresponding bromoester in a yield ranging from 62-88% was obtained. This reaction has been performed successfully on a broad range of scales from 10 mmol to 0.5 mol. The bromo ester derivatives were typically prepared in pure form on a large scale without the need for purification by column chromatography.

Step I: Alternative Preparation of Alkylating Agent

Typically, the first step (i) is the preparation of the alkylating agent obtained by reaction between the bromoacetyl bromide and different alcohols, amines or thiols. The reaction involving bromoacetyl bromide and alcohols was performed in the absence of solvent and promoted by neutral alumina. The reaction required typically 1 hour to reach completion, cooling with an ice bath during addition, then warming to RT without any requirement of an inert atmosphere, according to the procedure of Yadav. After purification by absorption of the crude reaction mixture onto excess solid $NaHCO_3$ and standing overnight, the solid was washed with toluene, filtered and the filtrate evaporated to give the corresponding bromoester in a yield typically around 88%. This reaction has been performed successfully on a broad range of scales using at least 2 equivalents of bromoacetyl bromide with the different alcohols.

The bromides prepared by this method are pure enough to carry through to the subsequent imidazole alkylation without the need for purification by column chromatography.

Preparation of (R)-methyl 2-bromoacetoxy-2-phenylacetate

To a stirred solution of DCM, (R)-methyl mandelate (1.48 g, 8.92 mmol), and triethylamine (2.02 g, 20.0 mmol), in DCM (30 ml) under a nitrogen atmosphere at −78° C. was added dropwise bromoacetyl bromide (3.03 g, 15.0 mmol). After stirring at −78° C. for 5 h, the reaction mixture was allowed warm up to −20° C. and quenched by addition of water (20 mL). The organic phase was washed with distilled water (3×20 mL), saturated ammonium chloride (3×20 mL), saturated sodium bicarbonate (3×20 mL) and brine (2×20 mL). The organic phase was then dried over magnesium sulfate, filtered and solvents removed via rotary evaporation to yield a crude product in 84% yield (2.13 g, 7.42 mmol). Column chromatography was performed on the crude product (mobile phase: DCM:Hexane, 50:50) to give a pale yellow liquid at RT in 73% yield (1.85 g, 6.45 mmol).

Alternative Preparation of (R)-methyl 2-bromoacetoxy-2-phenylacetate

To methyl (R)-mandelate (8.3 g, 150 mmol), and neutral alumina [e.g. Aldrich type WN-3] (17 g, 167 mmol) cooled with an ice-bath was added bromoacetyl bromide (44 mL, 500 mmol). The ice bath was removed and after 1 h standing at RT, the reaction mixture was poured onto solid $NaHCO_3$ (117 g) in a glass filter funnel, with a cotton wool plug (effervescence). After standing overnight, the solid was washed with toluene until 200 ml of filtrate had been collected. The volatiles were removed via rotary evaporation to yield a crude product in 88% yield. This crude product was sufficiently pure to carry through to the next step.

$^1$H NMR (400 MHz, $CDCl_3$) δ ppm 7.41-7.34 (m, 5H), 5.91 (s, 1H), 3.91 (d, J=1.6 Hz, 2H), 3.66 (s, 3H)

$^{13}$C NMR (100 MHz, $CDCl_3$) δ ppm 168.60 (CO), 166.61 (CO), 133.00 (ArC), 129.60 (ArC), 128.94 (ArC), 127.68 (ArC), 75.68 (COO), 52.86 (OCH3), 25.32 (CH2)

Preparation of alkyl-2-chloro-(3,4-dimethoxyphenyl)acetates

The mandelic acid derivative is converted to the mandelic acid ester then the alcohol group transformed to a chloride by treatment with thionyl chloride.

Synthesis of butyl 3,4-dimethoxy mandelate

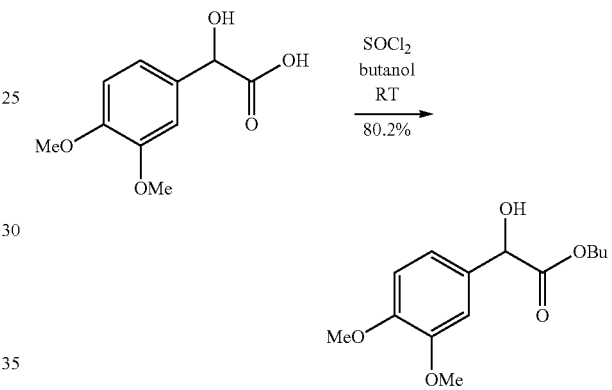

Synthesis:

A solution of 3,4-dimethoxy mandelic acid (7.501 g, 35.3 mmol) in butanol (15 mL) was stirred at room temperature. Thionyl chloride (3.6 mL, 49.3 mmol) was added drop wise. Reaction was monitored by TLC and stirred for 2 h. Reaction was quenched by addition of water (50 mL) and product was extracted with DCM (8×25 mL). Organic phase was dried over anhydrous magnesium sulphate and coevaporated ten times with hexane to remove remaining butanol. Pure product as yellow oil in 80.2% yield (7.601 g, 28.4 mmol) was obtained.

Product Characterization:
Molecular formula: $C_{14}H_{20}O_3$
Molecular weight: 268.3 g/mol
$^1$H NMR (400 Hz, $CDCl_3$) δ ppm 7.04-6.92 (m, 2H), 6.83 (d, 1H, J=8.0 Hz), 5.09 (s, 1H), 4.21-4.10 (m, 2H), 3.87 (s, 3H), 3.86 (s, 3H), 1.62-1.52 (m, 2H), 1.32-1.21 (m, 2H), 0.85 (t, 3H, J=8.0 Hz)

Synthesis of butyl-2-chloro-(3,4-dimethoxyphenyl)acetate

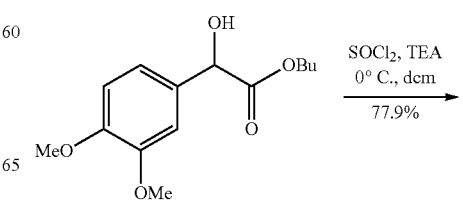

-continued

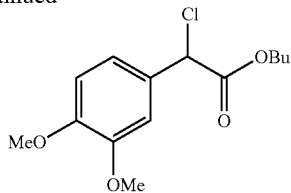

Synthesis:
A solution of 3,4-dimethoxy butyl mandelate (3.018 g, 11.26 mmol) in DCM (50 mL) was stirred at 0° C. Thionyl chloride (0.82 mL, 11.26 mmol) was added drop wise followed by addition of triethylamine (1.56 mL, 11.26 mmol). Reaction was monitored by TLC and stirred for 4 h. The product was then washed with distilled water (3×20 mL). The organic phase was dried over anhydrous magnesium sulphate, filtrated and solvent removed on the rotary evaporator. Flash column chromatography was performed on the crude product (mobile phase, DCM) to yield a colorless oil in 77.9% yield (2.513 g, 8.77 mmol).

Product Characterization:
Molecular formula: $C_{14}H_{19}ClO_4$
Molecular weight: 286.8 g/mol
$^1$H NMR (400 Hz, CDCl$_3$) δ ppm 7.04 (d, 1H, J=2.2 Hz), 7.01 (dd, 1H, J=8.3, 2.2 Hz), 6.82 (d, 1H, J=8.3 Hz), 5.30 (s, 1H), 4.22-4.11 (m, 2H), 3.89 (s, 3H), 3.88 (s, 3H), 1.60 (m, 2H), 1.31 (tq, 2H, J=7.5, 7.5 Hz), 0.88 (t, 3H, J=7.4 Hz)
$^{13}$C δ ppm (100 Hz, CDCl$_3$) 168.59 (CO), 149.81 (ArC), 149.16 (ArC), 128.15 (ArC), 120.77 (ArC), 110.77 (ArC), 110.60 (ArC), 66.24 (OCH$_2$), 59.25 (CH), 55.90 (OCH$_3$), 55.90 (OCH$_3$), 30.38 (CH$_2$), 18.92 (CH$_2$), 13.60 (OCH$_3$).

Experimental Methods for Preparation of Bromide, Chloride, NTf$_2$ and OctOSO$_4$ Ionic Liquids Representative Procedure for the Preparation of Chiral Bromide Salts (RS-3-methyl-1-(methylmandelylcarbonylmethyl)imidazolium bromide) (KG89)

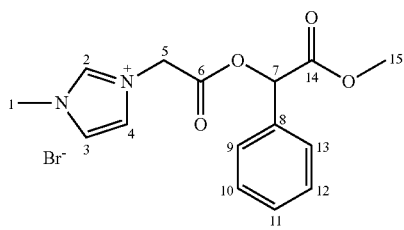

Synthesis:
To a stirred solution of 1-methylimidazole (18.0 mmol, 1.48 g) in diethyl ether (100 mL) at −15° C. under a nitrogen atmosphere was added drop wise RS-methyl mandelyl bromoacetate (20.0 mmol, 5.74 g). The reaction mixture was stirred vigorously at −15° C. for 4 h, then at RT overnight. The ether top phase was decanted and the product washed with ether (3×10 mL), the solvent removed on the rotary evaporator and dried under high vacuum for 8 h to give an off-white powder at RT in 94% yield (6.90 g, 18.7 mmol).

Product Characterization:
Molecular formula $C_{15}H_{17}BrN_2O_4$
Molecular weight 369 g/mol $^1$H NMR (400 MHz, CDCl$_3$) δ ppm 10.25 (s, 1H, H2), 7.61 (s, 1H, H3), 7.47 (s, 1H, H4), 7.45-7.50 (m, 5H, H's 9-13), 6.02 (s, 1H, H7), 5.81 (d, J=17.6 Hz, 1H, H5), 5.56 (d, J=17.6 Hz, 1H, H5), 4.05 (s, 3H, H1), 3.72 (s, 3H, H15)
$^{13}$C NMR (100 MHz, CDCl$_3$) δ ppm 168.46 (CO), 165.76 (CO), 138.56 (NCH$_2$N), 132.29 (ArC), 129.88 (ArC), 129.06 (ArC), 127.86 (ArC), 123.72 (NCH$_2$), 123.05 (NCH$_2$), 76.23 (OCH), 53.09 (NCH$_2$), 50.22 (OCH$_3$), 36.95 (NCH$_3$)
MP (° C.) 140-142
IR (KBr disc) (cm$^{-1}$) 3482, 3393, 3088, 1762, 1744, 1576, 1565, 1453, 1436, 1380, 1285, 1231, 1213, 1174, 1019
MS m/z, Found 289.1185 [M-Br—]$^+$. Calcd. $C_{18}H_{23}N_2O_4$ 289.1188.
MS m/z, 289.1 [M-Br$^-$]$^+$; MS: m/z, 78.9 [Br$^-$]

R-3-Methyl-1-(methylmandelylcarbonylmethyl)imidazolium bromide (KG90)

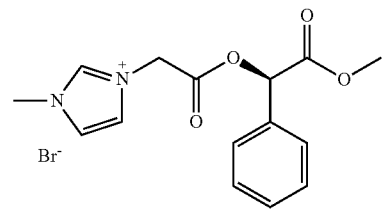

Synthesis:
The title compound (a beige solid) was prepared from R-mandelate bromoacetate (11.48 g, 40.0 mmol) and 1-methylimidazole (3.12 g, 38.0 mmol) according to the general procedure in 93% yield (12.97 g, 35.2 mmol).

Product Characterization:
Molecular formula $C_{15}H_{17}BrN_2O_4$
Molecular weight 369 g/mol
$^1$H NMR (400 MHz, CDCl$_3$) δ ppm 10.03 (s, 1H), 7.59 (s, 1H), 7.48 (s, 1H), 7.37-7.31 (m, 5H), 5.93 (s, 1H), 5.70 (d, J=17.6 Hz, 1H), 5.50 (d, J=17.6 Hz, 1H), 3.96 (s, 3H), 3.63 (s, 3H)
$^{13}$C NMR (100 MHz, CDCl$_3$) δ ppm 168.50, 165.88, 138.22, 132.35, 129.84, 129.05, 127.85, 123.76, 123.28, 76.17, 53.09, 50.18, 36.94
MP (° C.) 99-101
IR (KBr disc) (cm$^{-1}$) 3477, 3393, 3090, 1761, 1746, 1577, 1564, 1452, 1432, 1380, 1285 1233, 1218, 1176, 1022
MS m/z, Found 289.1180 [M-Br—]$^+$. Calcd. $C_{18}H_{23}N_2O_4$ 289.1188.
MS m/z, 289.1 [M-Br$^-$]$^+$; MS: m/z, 78.9 [Br$^-$]
$[\alpha]_D^{20}$ -62.7 g (0.57 c, CHCl$_3$)

S-3-Methyl-1-(methylmandelylcarbonylmethyl)imidazolium bromide (KG91)

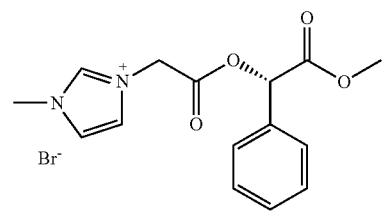

Off-white solid

Synthesis:

The title compound was prepared from S-mandelate bromoacetate (10.05 g, 35.0 mmol) and 1-methylimidazole (2.62 g, 32.0 mmol) according to the general procedure in 78% yield (10.10 g, 27.4 mmol)

Product Characterization:

Molecular formula $C_{15}H_{17}BrN_2O_4$

Molecular weight 369 g/mol $^1$H NMR (400 MHz, CDCl$_3$) δ ppm 10.16 (s, 1H), 7.53 (t, J=1.8 Hz, 1H), 7.39 (t, J=1.8 Hz, 1H), 7.38-7.32 (m, 5H), 5.94 (s, 1H), 5.73 (d, J=18.0 Hz, 1H), 5.49 (d, J=18.0 Hz, 1H), 3.98 (s, 3H), 3.66 (s, 3H)

$^{13}$C NMR (100 MHz, CDCl$_3$) δ ppm 168.48, 165.85, 138.34, 132.23, 129.85, 129.05, 127.85, 123.76, 123.21, 76.19, 53.08, 50.20, 15.29

MP (° C.) 97-99

IR (KBr disc) (cm$^{-1}$) 3481, 3393, 3086, 2949, 1763, 1744, 1577, 1566, 1452, 1434, 1380, 1285, 1231, 1213, 1174 1018

MS m/z, Found 289.1181 [M-Br—]$^+$. Calcd. $C_{13}H_{23}N_2O_4$ 289.1188.

MS m/z, 289.1 [M-Br$^-$]$^+$; MS: m/z, 78.9 [Br$^-$]

[α]$_D^{20}$ +63.8° (0.59 c, CHCl$_3$)

Representative Procedure for the Preparation of Chiral NTf$_2$ Salts (RS-3-Methyl-1-(methylmandelylcarbonylmethyl)imidazolium NTf$_2$) (KG92)

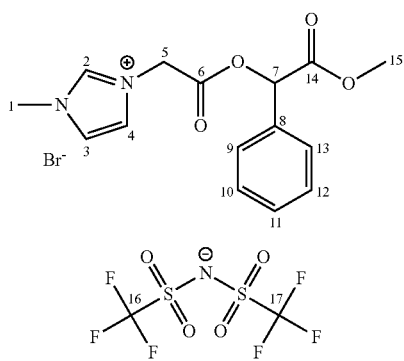

Synthesis:

A flask was charged with RS-3-methyl-1-(methyl mandelyl carbonylmethyl) imidazolium bromide (0.67 g, 1.81 mmol) and distilled water (10 mL). LiNTf$_2$ (0.86 g, 3.00 mmol) was added in one portion and the suspension was stirred vigorously for overnight at RT. The top aqueous layer was removed and the IL was washed with distilled water (3×5 mL). The solvent was then removed on the rotary evaporator and under high vacuum for 5 h to give an orange crystalline material at RT in 92% yield (0.95 g, 1.67 mmol)

Product Characterization:

Molecular formula $C_{17}H_{17}F_6N_3O_8S_2$

Molecular weight 569 g/mol $^1$H NMR (400 MHz, CDCl$_3$) δ ppm 8.73 (s, 1H, H1), 7.32 (broad s, 5H, H's 9-13), 7.31 (s, 1H, H3), 7.22 (s, 1H, H4), 5.93 (s, 1H, H7), 5.08 (s, 2H, H5), 3.84 (s, 3H, H1), 3.62 (s, 3H, H15)

$^{13}$C NMR (100 MHz, CDCl$_3$) δ ppm 168.42 (COO), 165.33 (COO), 137.68 (NCHN), 132.25 (ArC), 129.91 (NCH$_2$), 129.05 (NCH$_2$), 127.79 (ArC), 123.77 (q, J=319 Hz, 2CF$_3$), 76.36 (OCH), 53.02 (NCH$_2$), 49.80 (OCH$_3$), 36.56 (NCH$_3$)

MP (°) 73-75

IR (KBr disc) (cm$^{-1}$) 3470, 3379, 2099, 1750, 1571, 1566, 1459, 1453, 1451, 1390, 1197, 1127

MS m/z, 289.1 [M-NTf$_2^-$]$^+$; MS: m/z, 280.0 [NTf$_2^-$]

RS-3-Methyl-1-(ethylmandelylcarbonylmethyl)imidazolium NTf$_2$ (KG 813)

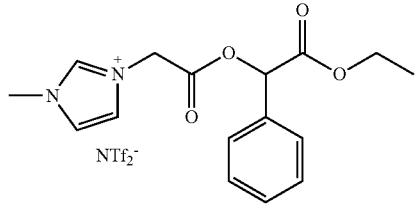

Pale brown viscous liquid

Synthesis:

The title compound was prepared from RS-3-methyl-1-(ethyl mandelyl carbonyl methyl) imidazolium bromide (0.96 g, 2.60 mmol) and LiNTf$_2$ (1.00 g, 3.50 mmol) according to the general procedure in 95% yield (1.43 g, 2.45 mmol)

Product Characterization:

Molecular formula $C_{13}H_{20}F_6N_3O_8S_2$

Molecular weight 583 g/mol $^1$H NMR (400 MHz, CDCl$_3$) δ ppm 8.79 (s, 1H), 7.37-7.35 (m, 5H), 7.31 (t, J=1.8 Hz, 1H), 7.22 (t, J=1.8 Hz, 1H), 5.91 (s, 1H), 5.10 (d, J=18 Hz, 2H), 4.20-4.03 (m, 2H), 3.87 (s, 3H), 1.13 (t, J=7.2 Hz, 3H)

$^{13}$C NMR (100 MHz, CDCl$_3$) δ ppm 167.89, 165.27, 137.84, 132.29, 129.86, 129.02, 127.78, 123.71, 123.25, 121.27 (q, J=320 Hz, 2C), 76.52, 62.33, 49.88, 36.64, 13.91

IR (thin film on salt plate) (cm$^{-1}$) 3167, 3120, 2960, 2927, 2860, 1751, 1566, 1559, 1540, 1495, 1457, 1354, 1198, 1136

MS m/z, 303.1 [M-NTf$_2^-$]$^+$; MS: m/z, 280.0 [NTf$_2$]

R-3-Methyl-1-(ethylmandelylcarbonylmethyl)imidazolium NTf$_2$ (KG 829)

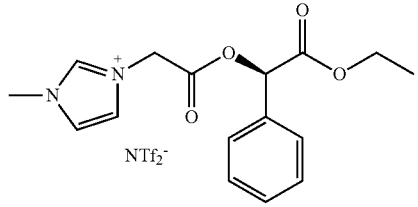

Orange solid

Synthesis:

The title compound was prepared from R-3-methyl-1-(ethyl mandelyl carbonyl methyl) imidazolium bromide (1.03 g, 2.70 mmol) and LiNTf$_2$ (0.86 g, 3.00 mmol) according to the general procedure in 89% yield (1.41 g, 2.41 mmol)

Product Characterization:

Molecular formula $C_{13}H_{20}F_6N_3O_8S_2$

Molecular weight 583 g/mol $^1$H NMR (400 MHz, CDCl$_3$) δ ppm 8.67 (s, 1H), 7.36-7.29 (m, 6H), 7.24 (t, J=1.6 Hz, 1H), 5.88 (s, 1H), 5.05 (s, 2H), 4.16-4.11 (m, 2H), 3.81 (s, 3H), 1.10 (t, J=7.2 Hz, 3H)

$^{13}$C NMR (100 MHz, CDCl$_3$) δ ppm 167.92, 165.38, 137.49, 132.40, 129.81, 128.99, 127.74, 123.74, 123.46, 121.27 (q, J=320 Hz, 2C), 76.46, 62.29, 49.72, 36.47, 13.84

MP (° C.) 44-46
IR (KBr disc) (cm$^{-1}$) 3156, 3099, 3007, 1761, 1735, 1579, 1568, 1500, 1456, 1430, 1371, 1356, 1279, 1187, 1132, 1051
MS m/z, 303.1 [M-NTf$_2$]$^+$; MS: m/z, 280.0 [NTf$_2^-$]
[α]$_D^{20}$ −53.7° (0.5 c, CHCl$_3$)

S-3-Methyl-1-(ethylmandelylcarbonylmethyl)imidazolium NTf$_2$ (KG 821)

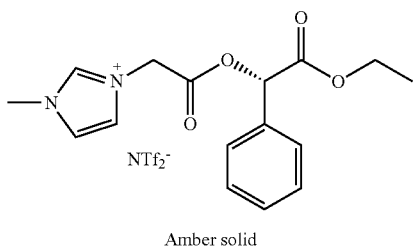

Amber solid

Synthesis:
The title compound was prepared from S-3-methyl-1-(ethyl mandelyl carbonyl methyl) imidazolium bromide (0.96 g, 2.50 mmol) and LiNTf$_2$ (0.86 g, 3.00 mmol) according to the general procedure in 98% yield (1.42 g, 2.44 mmol)
Product Characterization:
Molecular formula C$_{13}$H$_{20}$F$_6$N$_3$O$_8$S$_2$
Molecular weight 583 g/mol
$^1$H NMR (400 MHz, CDCl$_3$) δ ppm 8.72 (s, 1H), 7.36-7.32 (m, 5H), 7.30 (t, J=1.8 Hz, 1H), 7.23 (t, J=1.8 Hz, 1H), 5.89 (s, 1H), 5.07 (s, 2H), 4.18-4.02 (m, 2H), 3.85 (s, 3H), 1.12 (t, J=7.0 Hz, 3H)
$^{13}$C NMR (100 MHz, CDCl$_3$) δ ppm 167.92, 165.34, 137.64, 132.36, 129.83, 129.01, 127.76, 123.74, 123.38, 121.27 (q, J=320 Hz, 2C), 76.49, 62.31, 49.80, 36.55, 13.88
MP (° C.) 44-46
IR (KBr disc) (cm$^{-1}$) 3165, 3099, 2998, 2963, 1759, 1735, 1579, 1564, 1496, 1452, 1434, 1356, 1279, 1198, 1134, 1044
MS m/z, 303.1 [M-NTf$_2^-$]$^+$; MS: m/z, 280.0 [NTf$_2$]
[α]$_D^{20}$ +54.7 g (0.7 c, CHCl$_3$)

Representative Procedure for the Preparation of Chiral OctOSO$_3$ Salts (RS-3-Methyl-1-(methylmandelylcarbonylmethyl)imidazolium OctOSO$_3$) (KG 86)

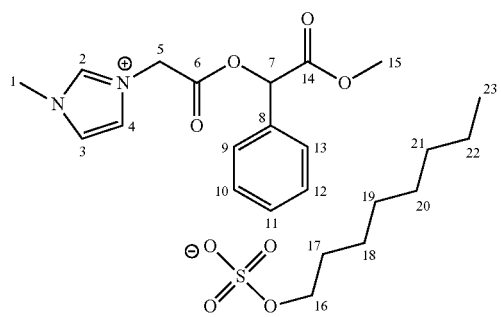

Synthesis:
To a stirred solution of RS-3-methyl-1-(methyl mandelyl carbonyl methyl) imidazolium bromide (2.50 mmol, 0.92 g) in distilled water (20 mL) was added in one portion sodium octyl sulfate (2.60 mmol, 0.60 g). The mixture was left stirring overnight, then the water was evaporated on the rotary evaporator. The remaining product was dissolved in DCM (10 mL) and washed with water (2×2 mL). The product was then dried on the rotary evaporator and under high vacuum for 8 h to give a pale brown solid at RT in 71% yield (0.89 g, 1.78 mmol)
Product Characterization:
Molecular formula C$_{23}$H$_{34}$N$_2$O$_8$S$_2$
Molecular weight 498 g/mol
$^1$H NMR (400 MHz, CDCl$_3$) δ ppm 9.24 (s, 1H, H2), 7.48 (t, J=1.6 Hz, 1H, H3), 7.42 (t, J=1.6 Hz, 1H, H4), 7.36-7.30 (m, 5H, H's 9-13), 5.91 (s, 1H, H7), 5.32 (d, J=17.8 Hz, 1H, H5), 5.24 (d, J=17.8 Hz, 1H, H5), 3.88-3.83 (m, 5H, H's 15 and 16), 3.61 (s 3H, H1), 1.52 (tt, J=7.2 Hz, 7.2 Hz, 2H, H17), 1.22-1.12 (m, 10H, H's 18-22), 0.81 (t, J=7.2 Hz, 3H, H23)
$^{13}$C NMR (100 MHz, CDCl$_3$) δ ppm 167.50 (COO), 165.11 (COO), 137.55 (NCHN), 131.54 (ArC), 128.68 (ArC), 127.93 (ArC), 126.75 (ArC), 122.81 (NCH$_2$), 122.45 (NCH$_2$), 75.08 (CH), 66.75 (OCH$_3$), 51.89 (OCH$_2$), 48.65 (NCH$_2$), 35.40 (CH$_2$), 30.78 (NCH$_3$), 28.44 (CH$_2$), 28.31 (CH$_2$), 28.22 (CH$_2$), 24.81 (CH$_2$), 21.62 (CH$_2$), 13.10 (CH$_3$)
MP (° C.) 61-62
IR (KBr disc) (cm$^{-1}$) 3159, 3125, 2963, 2932, 2850, 1740, 1552, 1531, 1495, 1454, 1399, 1210, 1177
MS m/z, 289.1188 [M-OctOSO$_3^-$]$^+$; MS: m/z, 209.1 [OctOSO$_3^-$]

RS-3-Methyl-1-(ethylmandelylcarbonylmethyl)imidazolium OctOSO$_3$ (KG 307)

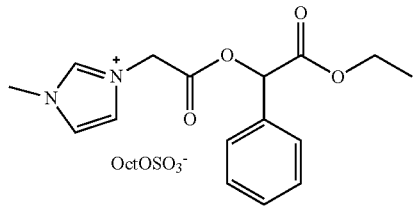

Yellow grease

Synthesis:
The title compound was prepared from RS-3-methyl-1-(ethyl mandelyl carbonyl methyl) imidazolium bromide (2.50 mmol, 0.94 g) and sodium octyl sulfate (2.60 mmol, 0.60 g) according to the general procedure in 92% yield (1.18 g, 2.30 mmol)
Product Characterization:
Molecular formula C$_{24}$H$_{36}$N$_2$O$_8$S$_2$
Molecular weight 512 g/mol
$^1$H NMR (400 MHz, CDCl$_3$) δ ppm 9.46 (s, 1H), 7.48 (t, J=1.6 Hz, 1H), 7.44-7.33 (m, 5H), 7.36 (t, J=1.6 Hz, 1H), 5.99 (s, 1H), 5.48 (d, J=18 Hz, 1H), 5.33 (d, J=18 Hz, 1H), 4.19-4.09 (m, 2H), 3.98 (s, 3H), 1.63 (m, 2H), 1.31-1.19 (m, 12H), 1.22 (t, J=7.0 Hz, 3H), 0.88 (t, J=7.0 Hz, 3H)
$^{13}$C NMR (100 MHz, CDCl$_3$) δ ppm 168.02, 165.93, 138.85, 132.50, 129.72, 128.58, 127.79, 123.62, 123.11, 76.29, 68.24, 62.22, 49.90, 36.67, 31.82, 29.39, 29.32, 29.25, 25.80, 22.66, 14.13, 13.97
IR (thin film on salt plate) (cm$^{-1}$) 2958, 2927, 2857, 1748, 1559, 1539, 1495, 1452, 1401, 1202, 1176
MS m/z, 303.1 [M-OctOSO$_3^-$]$^+$; MS: m/z, 209.1 [OctOSO$_3^{31}$]

R-3-Methyl-1-(ethylmandelylcarbonylmethyl)imidazolium OctOSO₃ (KG 401)

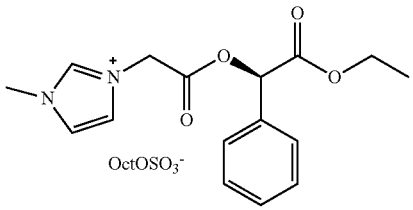

Pale brown solid

Synthesis:

The title compound was prepared from R-3-methyl-1-(ethyl mandelyl carbonyl methyl)imidazolium bromide (2.50 mmol, 0.95 g) and sodium octyl sulfate (2.60 mmol, 0.60 g) according to the general procedure in 95% yield (1.22 g, 2.39 mmol)

Product Characterization:
Molecular formula $C_{24}H_{36}N_2O_8S_2$
Molecular weight 512 g/mol
$^1$H NMR (400 MHz, CDCl$_3$) δ ppm 9.46 (s, 1H), 7.39 (t, J=1.6 Hz, 1H), 7.34-7.24 (m, 5H), 7.28 (t, J=1.6 Hz, 1H), 5.90 (s, 1H), 5.41 (d, J=18 Hz, 1H), 5.25 (d, J=18 Hz, 1H), 4.13-3.98 (m, 2H), 3.90 (s, 3H), 1.54 (tt, J=7.2, 7.4 Hz, 2H), 1.21-1.13 (m, 12H), 1.13 (t, J=7.4 Hz, 3H), 0.80 (t, J=7.4 Hz, 3H)
$^{13}$C NMR (100 MHz, CDCl$_3$) δ ppm 168.03, 165.94, 138.95, 132.48, 129.73, 128.58, 126.55, 123.60, 123.07, 76.29, 68.08, 62.23, 49.88, 36.65, 31.83, 29.42, 29.33, 29.25, 25.81, 22.67, 14.14, 13.98
MP (° C.) 40-43
IR (KBr disc) (cm$^{-1}$) 3160, 3120, 2956, 2927, 2856, 1751, 1565, 1559, 1539, 1495, 1456, 1403, 1205, 1177
MS m/z, 303.1 [M-OctOSO$_3^-$]$^+$; MS: m/z, 209.1 [OctOSO$_3^-$]
$[α]_D^{20}$ −44.5° (0.8 c, Acetone)

S-3-Methyl-1-(ethylmandelylcarbonylmethyl)imidazolium OctOSO₃ (KG 300)

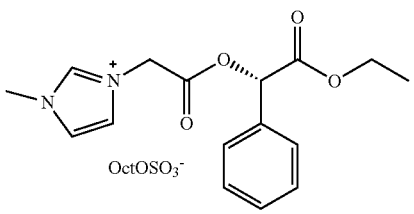

Pale brown solid

Synthesis:

The title compound was prepared from S-3-methyl-1-(ethyl mandelyl carbonyl methyl)imidazolium bromide (2.60 mmol, 1.00 g) and sodium octyl sulfate (2.70 mmol, 0.63 g) according to the general procedure in 91% yield (1.21 g, 2.36 mmol)

Product Characterization:
Molecular formula $C_{24}H_{36}N_2O_8S_2$
Molecular weight 512 g/mol
$^1$H NMR (400 MHz, CDCl$_3$) δ ppm 9.40 (s, 1H), 7.35-7.28 (m, 6H), 7.26 (s, 1H), 5.90 (s, 1H), 5.38 (d, J=18 Hz, 1H), 5.22 (d, J=18 Hz, 1H), 4.10-4.02 (m, 2H), 3.90 (s, 3H), 1.54-1.49 (m, 2H), 1.17-1.12 (m, 15H), 0.80 (t, J=7.0 Hz, 3H)
$^{13}$C NMR (100 MHz, CDCl$_3$) δ ppm 167.99, 165.90, 139.09, 132.48, 129.72, 128.97, 127.80, 123.56, 123.03, 76.31, 68.15, 62.21, 49.87, 36.63, 31.82, 29.41, 29.33, 29.25, 25.81, 22.66, 14.13, 13.97
MP (° C.) 38-40
IR (KBr disc) (cm$^{-1}$) 3163, 3116, 2956, 2927, 2856, 1748, 1566, 1559, 1494, 1457, 1399, 1213, 1177
MS m/z, 303.1 [M-OctOSO$_3^-$]$^+$; MS: m/z, 209.1 [OctOSO$_3^-$]
$[α]_D^{20}$ +43.8° (0.7 c, Acetone)

Preparation of 2-(3,4-dimethoxyphenyl)-2-(3-methylimidazolium) butyl acetate, chloride salt (KG 2003)

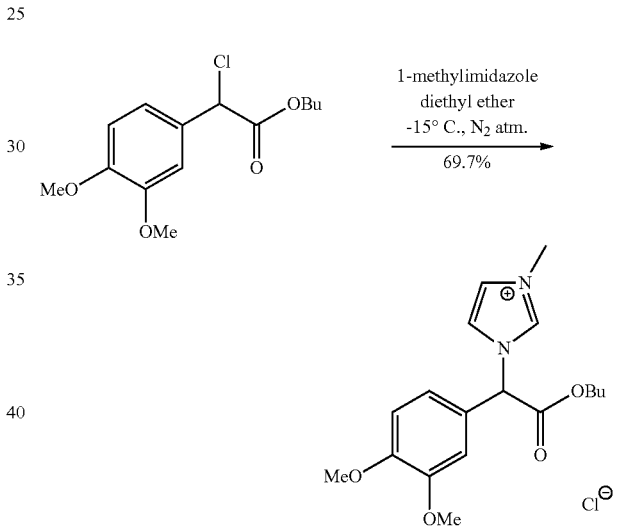

Synthesis:

To a stirred solution of butyl 2-chloro-2-(3,4-dimethoxyphenyl)acetate (2.004 g, 7.00 mmol) in diethyl ether (50 mL) at −15° C. under a nitrogen atmosphere 1-methylimidazole (0.48 mL, 6.09 mmol) was added drop wise. The reaction mixture was stirred at room temperature for 48 h. White precipitate and organic layer were collected and solvent was removed on the rotary evaporator. Product was washed with diethyl ether yielding white crystalline powder in 69.7% yield (1.565 g, 4.24 mmol).

Product Characterization:
Molecular formula: $C_{13}H_{25}ClN_2O_4$
Molecular weight: 368.9 g/mol
$^1$H NMR (400 Hz, CDCl$_3$) δ ppm 10.89 (s, 1H), 7.39 (s, 1H), 7.34 (d, 1H, J=2.0 Hz), 7.20 (s, 1H), 7.11 (s, 1H), 7.02 (dd, 1H, J=8.4, 1.6 Hz,), 6.87 (d, 1H, J=8.4 Hz), 4.30-4.18 (m, 2H), 4.03 (s, 3H), 3.92 (s, 3H), 3.88 (s, 3H), 1.63-1.57 (m, 2H), 1.28 (tq, 2H, J=7.4, 7.4 Hz), 0.87 (t, 3H, J=7.4 Hz)
$^{13}$C δ ppm (100 Hz, CDCl$_3$) 167.95 (CO), 150.42 (ArC), 149.74 (ArC), 137.84 (ArC), 124.77 (ArC), 123.12 (ArC), 121.73 (ArC), 120.78 (ArC), 112.29 (ArC), 111.50 (ArC), 66.88 (OCH$_2$), 63.96 (NCH), 56.41 (OCH$_3$), 56.03 (OCH$_3$), 36.81 (NCH$_3$), 30.25 (CH$_2$), 18.88 (CH$_2$), 13.58 (CH$_3$)

MS m/z, 333.10 [M-Cl$^-$]$^+$

Synthesis of 2-(3,4-dimethoxyphenyl)-2-(3-methylimidazolium) butyl acetate, octylsulphate salt (KG 2004)

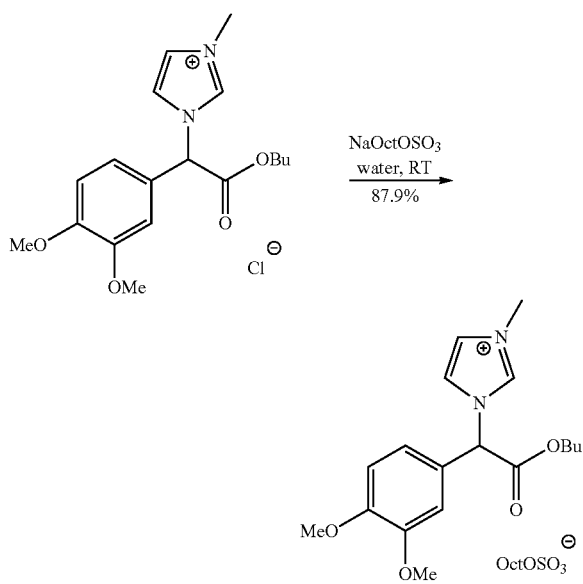

Synthesis:

To a stirred solution of 2-(3,4-dimethoxyphenyl)-2-(3-methylimidazolium) butyl acetate, chloride salt (0.672 g, 1.82 mmol), in distilled water (10 mL) was added in one portion sodium octyl sulfate (0.440 g, 1.90 mmol). The mixture was left stirring overnight, then the water was evaporated on the rotary evaporator. The remaining product was dissolved in DCM (12 mL) and washed with water (2×2 mL). The product was then dried on the rotary evaporator and under high vacuum to give white crystals in 87.9% yield (0.866 g, 1.60 mmol).

Product Characterization:

Molecular formula: C$_{26}$H$_{42}$N$_2$O$_8$S

Molecular weight: 542.7 g/mol $^1$H NMR (400 Hz, CDCl$_3$) δ ppm 9.55 (s, 1H), 7.39 (dd, 1H, J=1.6, 1.2 Hz), 7.32 (dd, 1H, J=2.0, 1.6 Hz) 7.12 (d, 1H, J=2.0 Hz), 6.95 (dd, 1H, J=8.4, 2.0 Hz), 6.83 (d, 1H, J=8.4 Hz), 6.62 (s, 1H), 4.24-4.10 (m, 2H), 3.97 (t, 2H, J=7.0 Hz) 3.92 (s, 3H), 3.84 (s, 3H), 3.82 (s, 3H), 1.62-1.48 (m, 4H), 1.29-1.25 (m, 2H), 1.23-1.13 (m, 10H), 0.804 (t, 3H, J=7.6 Hz), 0.795 (t, 3H, J=7.2 Hz)

$^{13}$C δ ppm (100 Hz, CDCl$_3$) 168.05 (CO), 150.62 (ArC), 150.00 (ArC), 137.99 (ArC), 124.59 (ArC), 123.31 (ArC), 121.83 (ArC), 120.80 (ArC), 112.47 (ArC), 111.60 (ArC), 67.98 (OCH$_2$), 67.03 (OCH$_2$), 64.42 (NCH), 56.49 (OCH$_3$), 56.15 (OCH$_3$), 36.72 (NCH$_3$), 31.99 (CH$_2$), 30.42 (CH$_2$), 29.71 (CH$_2$), 29.53 (CH$_2$), 29.43 (CH$_2$), 26.07 (CH$_2$), 22.82 (CH$_2$), 19.03 (CH$_2$), 14.29 (CH$_3$), 13.73 (CH$_3$)

MS m/z, 333.10 [M-OctOSO$_3^-$]$^+$

Synthesis of 2-(3,4-dimethoxyphenyl)-2-(3-methylimidazolium) butyl acetate, NTf$_2$ salt (KG 2005)

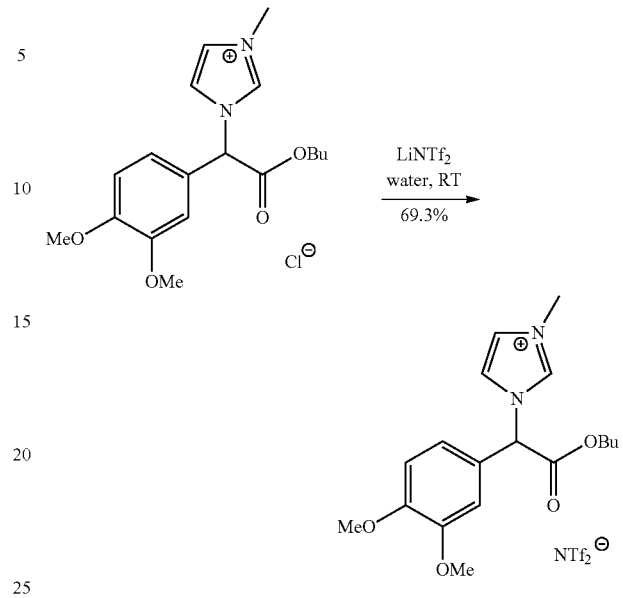

Synthesis:

A flask was charged with 2-(3,4-dimethoxyphenyl)-2-(3-methylimidazolium) butyl acetate, chloride salt (0.235 g, 064 mmol) and distilled water (8 mL). LiNTf$_2$ (0.201 g, 0.70 mmol) was added in one portion and the suspension was stirred vigorously for overnight at RT. The IL was washed with distilled water (2×3 mL). The solvent was then removed on the rotary evaporator and under high vacuum to give colorless oil at RT in 69.3% yield (0.272 g, 0.44 mmol).

Product Characterization:

Molecular formula: C$_{20}$H$_{25}$F$_6$N$_3$O$_8$S$_2$

Molecular weight: 613.6 g/mol $^1$H NMR (400 Hz, CDCl$_3$) δ ppm 8.93 (s, 1H), 7.24 (s, 1H), 7.17 (s, 1H), 6.99 (d, 1H, J=2.0 Hz), 6.96 (dd, 1H, J=8.4, 2.0 Hz), 6.92 (d, 1H, J=8.0 Hz), 6.35 (s, 1H), 4.28-4.24 (m, 2H), 3.99 (s, 3H), 3.91 (s, 3H), 3.88 (s, 3H), 1.66-1.58 (m, 2H), 1.29 (tq, 2H, J=7.5, 7.5 Hz), 0.88 (t, 3H, J=7.4 Hz)

$^{13}$C δ ppm (100 Hz, CDCl$_3$) 167.68 (CO), 151.01 (ArC), 150.19 (ArC), 136.54 (ArC), 123.47 (ArC), 122.44 (ArC), 121.20 (ArC), 120.02 (q, 2CF$_3$, J=319 Hz), 118.42 (ArC), 111.98 (ArC), 111.94 (ArC), 67.35 (OCH$_2$), 64.98 (NCH), 56.28 (OCH$_3$), 56.23 (OCH$_3$), 36.78 (NCH$_3$), 30.39 (CH$_2$), 19.02 (CH$_2$), 13.70 (CH$_3$).

MS m/z, 333.10 [M-NTf$_2^-$]$^+$

Preparation of 1-(1-methoxycarbonyl)-1-(3,4-methylendioxyphenyl)methoxycarbonyl methyl)-pyridinium bromide (KG 2016)

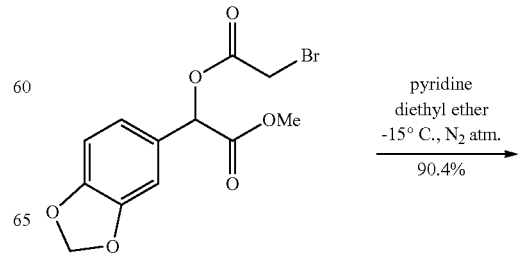

-continued

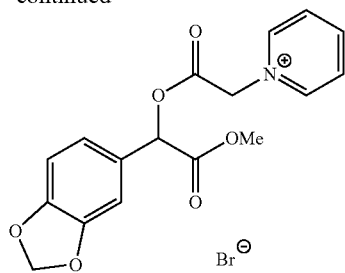

Synthesis:

To a stirred solution of (3,4-methylendioxyphenyl)methyl mandelate bromoacetate (1.502 g, 4.54 mmol) in diethyl ether (10 mL) at −15° C. under a nitrogen atmosphere, pyridine (0.37 mL, 4.54 mmol) was added drop wise. The reaction mixture was stirred at room temperature over the weekend. White precipitate appeared, but starting material was still present, so reaction mixture was refluxed for 4 h and stirred at RT overnight.

Product was washed with diethyl ether; the solvent was then removed on the rotary evaporator and under high vacuum to give a pure product as a white powder in 90.4% yield (1.682 g, 4.10 mmol).

Product Characterization:
Molecular formula: $C_{17}H_{16}BrNO_6$
Molecular weight: 410.2 g/mol
$^1$H NMR (400 Hz, CDCl$_3$) δ ppm 9.41-9.40 (m, 2H), 8.53-8.49 (m, 1H), 8.10-8.06 (m, 2H), 6.91 (dd, 1H, J=8.0, 1.8 Hz), 6.86 (d, 1H, J=1.8 Hz), 6.82 (d, 1H, J=8.0 Hz), 6.68 (d, 1H, J=17.4 Hz), 6.09 (d, 1H, J=17.4 Hz), 6.01 (d, 1H, J=1.4 Hz), 6.00 (d, 1H, J=1.4 Hz), 5.92 (s, 1H), 3.89 (s, 3H)

Preparation of
2-(3,4-dimethoxyphenyl)-2-(pyridinium) methyl acetate, chloride salt (KG 2013)

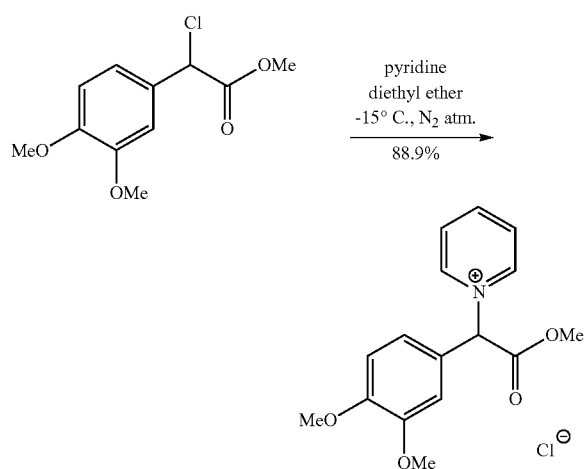

Synthesis:

To a stirred solution of methyl-2-chloro-2-(3,4-dimethoxyphenyl)acetate (0.895 g, 3.66 mmol) in diethyl ether (10 mL) at −15° C. under a nitrogen atmosphere, pyridine (0.35 mL, 4.37 mmol) was added drop wise. The reaction mixture was stirred at room temperature overnight, then was refluxed for 8 h and further pyridine was added (0.35 mL, 4.37 mmol). Yellow precipitate was collected and organic layer was evaporated and heated neat at 50° C. with pyridine (0.21 mL, 2.60 mmol). Product was washed with diethyl ether; the solvent was then removed on the rotary evaporator and under high vacuum to give a yellow powder in 88.9% yield (1.054 g, 3.26 mmol).

Product Characterization:
Molecular formula: $C_{16}H_{13}ClNO_4$
Molecular weight: 323.8 g/mol
$^1$H NMR (600 Hz, CDCl$_3$) δ ppm 9.44-9.43 (m, 2H), 8.51-8.48 (m, 1H), 8.07 (s, 1H), 8.06-8.03 (m, 2H) 7.43 (d, 1H, J=2.0 Hz), 7.04 (dd, 1H, J=8.4, 2.1 Hz), 6.82 (d, 1H, J=8.4 Hz), 3.762 (s, 3H), 3.760 (s, 3H), 3.72 (s, 3H)
$^{13}$C δ ppm (150 Hz, CDCl$_3$) 167.95 (CO), 150.98 (ArC), 149.99 (ArC), 146.57 (ArC), 144.99 (ArC), 128.02 (ArC), 123.35 (ArC), 121.80 (ArC), 113.43 (ArC), 111.59 (ArC), 73.44 (NCH), 56.48 (OCH$_3$), 56.00 (OCH$_3$), 54.01 (OCH$_3$).
MS m/z, 288.10 [M-Cl$^-$]$^+$
mp: 118-119° C.

Preparation of
2-(3,4-dimethoxyphenyl)-2-(pyridinium) methyl acetate, octylsulphate salt (KG2014)

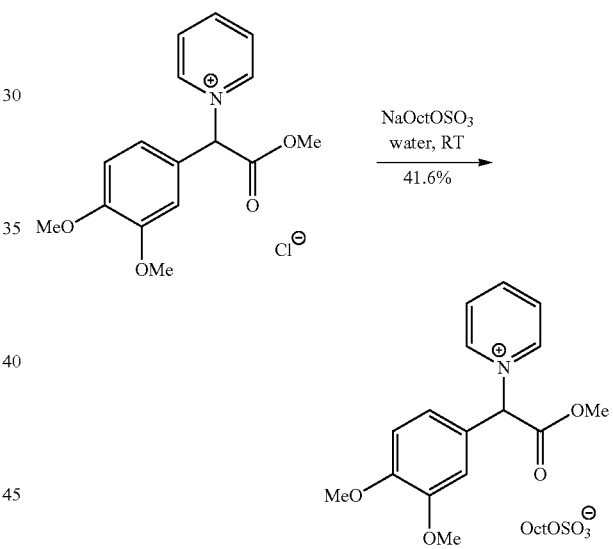

Synthesis:

To a stirred solution of 2-(3,4-dimethoxyphenyl)-2-(pyridinium) methyl acetate, chloride salt (0.278 g, 0.86 mmol), in distilled water (8 mL) was added in one portion sodium octyl sulphate (0.207 g, 0.89 mmol). The mixture was left stirring overnight, then the water was evaporated on the rotary evaporator. The remaining product was dissolved in DCM and washed with water. The product was then dried on the rotary evaporator and under high vacuum to give colorless oil at RT in 41.6% (0.178 g, 0.36 mmol)

Product Characterization:
Molecular formula: $C_{24}H_{35}NO_8S$
Molecular weight: 497.6 g/mol
$^1$H NMR (600 Hz, CDCl$_3$) δ ppm 9.08-9.07 (m, 2H), 8.48-8.45 (m, 1H), 8.02-8.00 (m, 2H), 7.26 (s, 1H), 7.24 (d, 1H, J=1.9 Hz), 7.02 (dd, 1H, J=8.4, 2.0 Hz), 6.85 (d, 1H, J=8.4 Hz), 3.92 (t, 2H, J=6.9 Hz), 3.779 (s, 3H), 3.775 (s, 3H), 3.74 (s, 3H), 1.51 (tt, 2H, J=7.2, 7.2 Hz), 1.23-1.18 (m, 2H), 1.16-1.11 (m, 8H), 0.75 (t, 3H, J=7.1 Hz)

$^{13}$C δ ppm (150 Hz, CDCl$_3$) 167.82 (CO), 151.20 (ArC), 150.28 (ArC), 146.96 (ArC), 145.02 (ArC), 128.36 (ArC), 123.18 (ArC), 122.09 (ArC), 113.52 (ArC), 111.87 (ArC), 74.51 (NCH), 67.76 (CH$_2$), 56.52 (OCH$_3$), 56.10 (OCH$_3$), 54.08 (OCH$_3$), 31.82 (CH$_2$), 29.61 (CH$_2$), 29.36 (CH$_2$), 29.25 (CH$_2$), 25.95 (CH$_2$), 22.65 (CH$_2$), 14.11 (CH$_3$).

MS m/z, 288.10 [M-OctOSO$_3{}^-$]$^+$

One Pot Method for Preparation of 2-(3,4-dihydroxyphenyl)-2-(3-methylimidazolium) butyl acetate bromide salt (KG 1041)

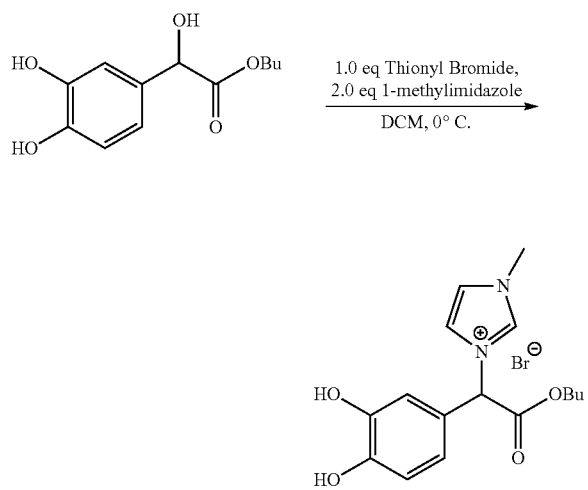

Preparation of 2-(3,4-dihydroxyphenyl)-2-(3-methylimidazolium) butyl acetate, octylsulphate salt (KG 1042)

Synthesis:

A solution of butyl 3,4-dihydroxy mandelate (10.04 g, 41.78 mmol), 1-methylimidazole (6.63 mL, 6.83 g, 83.25 mmol) in DCM (200 mL) was stirred at 0° C. Thionyl bromide (3.22 mL, 8.65 g, 41.62 mmol) was added drop wise to the solution. Reaction mixture was allowed to warm to RT and stirred for 24 h. Completion of reaction was confirmed by TLC. The volatiles were removed via rotary evaporation and the crude product was purified by column chromatography. (SiO$_2$, 20% Methanol: 80% DCM) to yield a brown oil in 62% yield (9.97 g, 25.88 mmol).

Product Characterization:

Molecular formula: C$_{16}$H$_{21}$BrN$_2$O$_4$.

Molecular weight: 385.25 g/mol $^1$H NMR (400 Hz, d$_6$-DMSO) δ ppm: 9.49 (s, 1H), 9.31 (s, 1H), 9.11 (s, 1H), 7.77 (t, 1H, J=2.0 Hz), 7.74 (t, 1H J=2.0 Hz), 6.85 (d, 1H, J=2.4 Hz), 6.83 (d, 1H, J=8.4 Hz), 6.75 (dd, 1H, J=2.4, 8.4 Hz), 6.60 (s, 1H), 4.26-4.14 (m, 2H), 3.86 (s, 3H), 1.59-1.51 (m, 2H), 1.23 (tq, 2H, J=7.2, 7.6 Hz), 0.83 (t, 3H, J=7.6 Hz)

$^{13}$C δ ppm (100 Hz, d$_6$-DMSO): 167.89 (C=O), 147.01 (ArC), 145.95 (ArC), 136.61 (ArC), 123.42 (ArC), 122.86 (ArC), 122.31 (ArC), 119.64 (ArC), 116.31 (ArC), 116.03 (ArC), 65.89 (CH), 63.52 (NCH$_3$), 35.95 (CH$_2$), 29.77 (CH$_2$), 18.33 (CH$_2$), 13.30 (CH$_3$)

MS m/z, 305.15 [M-Br$^-$]$^+$

Synthesis:

To a stirred solution of 2-(3,4-dihydroxyphenyl)-2-(3-methylimidazolium) butyl acetate bromide salt (2.0 g, 5.19 mmol), in distilled water (10 mL) was added in one portion sodium octyl sulphate (1.21 g, 5.19 mmol). The mixture was left stirring overnight, then the water was evaporated on the rotary evaporator. The crude product was dissolved in DCM and washed with water. The product was then dried on the rotary evaporator and under high vacuum to give brown oil in 41% yield (1.10 g, 2.13 mmol)

Product Characterization:

Molecular formula: C$_{24}$H$_{38}$N$_2$O$_7$S

Molecular weight: 514.63 g/mol $^1$H NMR (400 Hz, d$_6$-DMSO) δ ppm: 9.49 (s, 1H), 9.31 (s, 1H), 9.07 (s, 1H), 7.74 (t, 1H, J=2 Hz), 7.72 (d, 1H, J=2 Hz), 6.83 (d, 1H, J=2.0 Hz), 6.82 (d, 1H, J=8.0 Hz), 6.74 (dd, 1H, J=2.0, 8.0 Hz), 6.53 (s, 1H), 4.26-4.14 (m, 2H), 3.86 (s, 3H), 3.68 (t, 2H, J=6.8 Hz), 1.58-1.45 (m, 4H), 1.28-1.19 (m, 12H), 0.86 (t, 3H, J=7.2 Hz), 0.84 (t, 3H, J=7.6 Hz).

$^{13}$C δ ppm (100 Hz, d$_6$-DMSO: 167.84 (C=O), 146.98 (ArC), 145.93 (ArC), 136.58 (ArC), 123.47 (ArC), 122.77 (ArC), 122.37 (ArC), 119.77 (ArC), 116.11 (ArC), 115.77 (ArC), 65.91 (CH), 65.45 (CH$_2$), 63.61 (NCH$_3$), 35.95 (CH$_2$), 31.22 (CH$_2$), 29.78 (CH$_2$), 29.03 (CH$_2$), 28.70 (CH$_2$), 28.65 (CH$_2$), 25.50 (CH$_2$), 22.06 (CH$_2$), 18.34 (CH$_2$), 13.93 (CH$_3$), 13.37 (CH$_3$).

MS m/z, 305.15 [M-OctOSO$_3{}^-$]$^+$

Heterogeneous & Homogenous Hydrogenation Reactions Using the Chiral ILs vs. Conventional Solvents The novel CILs were tested as solvents in both heterogeneous and homogeneous hydrogenation reactions. Four prochiral substrates were examined: dimethyl itaconate, tiglic acid, α-acetamido cinnamic acid and α-methyl-trans-cinnamaldehyde. Heterogeneous catalysis was investigated using the achiral catalyst, palladium on carbon, while homogeneous catalysis was attempted using Wilkinson's catalyst.

Hydrogenation Reaction Conditions at 1 atm of Hydrogen Gas

Heterogeneous hydrogenation of the panel of olefin substrates was investigated under 1 atmosphere of hydrogen gas in each of the chiral lactate based and chiral mandelate based ionic liquid solvents tested. Both Pd—C and $PtO_2$ hydrogenation catalysts were used and the results were compared with conventional solvents such as methanol, THF and DCM.

The prochiral olefins to be hydrogenated using the IL as solvent were chosen from the panel of literature test-substrates: dimethyl itaconate, 5 tiglic acid, 6 (Z)-α-(N-acetamido)cinnamic acid 7 (and subsequently its methyl ester) and α-methyl-trans-cinnamaldehyde 8.

Hydrogenation Substrates

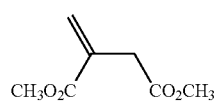

5

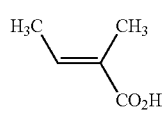

6

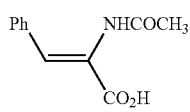

7

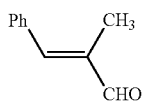

8

Hydrogenation Products

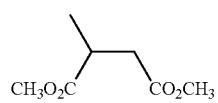

9

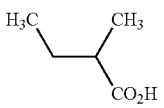

10

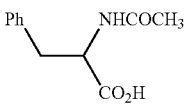

11

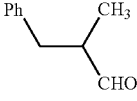

12

Hydrogenation Reactions of Dimethyl Itaconate 5

The catalytic hydrogenation of dimethyl itaconate 5 in the novel CILs led to one product, namely dimethyl 2-methylsuccinate 9. No stereoinduction was observed and the product 9 was formed as a racemic mixture.

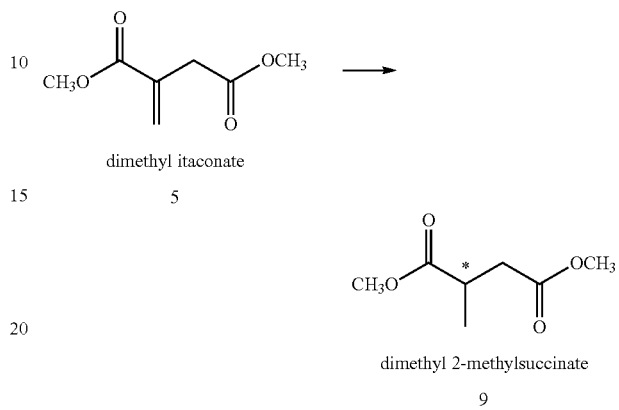

10% Palladium on carbon and Wilkinson's catalyst were separately investigated as catalysts for the hydrogenation of this prochiral substrate 5 in both achiral and chiral ILs.

General Procedure

Hydrogenation Reaction of Dimethyl Itaconate 5 in $[NTf_2]$ IL

Catalyst: 10% Pd—C/Tris(Triphenylphosphine)Rhodium(I) Chloride/Taniaphos

The catalyst [(10% Pd/C, 5.0 mg, 0.12 mol %), (Tris(triphenylphosphine)rhodium(I) chloride, 0.05 g, 1.35 mol %) (bis(norbornadiene)rhodium(I) $BF_4$, Taniaphos, 0.003 mmol, 0.75 mol %)] was weighed into a dry 2-neck round bottom flask. The predried CIL (2.0 mL) was then added to the flask, followed by dimethyl itaconate 5 (0.63 g, 4.00 mmol) and 3 $N_2$/vacuum cycles were performed. The reaction mixture was stirred for 10 minutes or until reaching 55° C. Hydrogen was then introduced to the reaction via a balloon, and the progress of the reaction was monitored by $^1H$ NMR. Upon termination of the reaction, the products were extracted using hexane (10×3 mL). The mass recovery after extraction from the CIL was 100% (0.63 g). Dimethyl 2-methylsuccinate 9 was obtained in 98% yield (0.63 g, 3.94 mmol) as a racemic mixture using either Pd—C (KG 813) or Wilkinson's catalyst (KG 834) and in 68% conversion using the Taniaphos catalyst (KG 813).

Recycle Procedure

Following extraction of the products from the IL, the IL (containing the catalyst) was dried via rotary evaporation and analysed by 1H NMR. Following confirmation that the IL was substrate/product-free and had not degraded, fresh substrate was then added to the system and the reactions repeated as described.

NMR: Dimethyl 2-Methylsuccinate 9 Product $^1$H NMR (400 MHz, CDCl$_3$) δ ppm 3.63 (s, 3H), 3.61 (s, 3H), 2.88-2.83 (m, 1H), 2.70 (dd, J=8.2, 8.2 Hz, 1H), 2.37 (dd, J=6.0, 6.0 Hz, 1H), 1.16 (d, J=7.2 Hz, 3H) $^{13}$C NMR (100 MHz, CDCl$_3$) δ ppm 175.98, 172.27, 51.89, 51.68, 37.15, 35.64, 16.96. Data consistent with literature values for 9

10% Palladium on carbon, Wilkinson's catalyst and Adams' catalyst were used to investigate the hydrogenation of this substrate in the novel CILs.

Catalyst: 10% Palladium on Carbon

Experiments were carried out at 55° C. using 0.22 mol % catalyst.

TABLE A

Lactate CILs Investigated in Hydrogenation of dimethyl itaconate 5

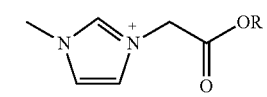

| R | Chirality of solvent | Conversion (%) to 9 |
|---|---|---|
| KG 802 (propyl lactate NTf$_2^-$) | +/− | 100 |
| KG 808 (propyl (S)-lactate NTf$_2^-$) | − | 100 |
| KG 803 (butyl lactate NTf$_2^-$) | +/− | 80 |
| KG 804 (pentyl lactate NTf$_2^-$) | +/− | 100 |

TABLE A-continued

Lactate CILs Investigated in Hydrogenation of dimethyl itaconate 5

| R | Chirality of solvent | Conversion (%) to 9 |
|---|---|---|
| KG 810 (pentyl (S)-lactate NTf$_2^-$) | − | 100 |
| KG 805 (2-ethoxyethyl lactate NTf$_2^-$) | +/− | 50 |

TABLE B

Mandelate CILs Investigated in Hydrogenation of dimethyl itaconate 5

| R | Chirality of solvent | Conversion (%) to 9 |
|---|---|---|
| KG 813 (ethyl mandelate NTf$_2^-$) | +/− | 100 |
| KG 400 (2-ethoxyethyl mandelate OctOSO$_3^-$) | +/− | 25 |

Catalyst: Wilkinson's Catalyst

The amount of catalyst deemed to be sufficient in order to induce relatively good percentage conversion was 1.26 mol % (50.0 mg).

TABLE C

Lactate and Mandelate ILs investigated in Hydrogenation of dimethyl itaconate 5

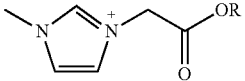

| R | Chirality of solvent | Catalyst amount Wilkinson's catalyst | Conversion (%) to 9 |
|---|---|---|---|
| KG 809 | − | 0.01 g | 15 |
| KG 825 | + | 0.01 g | 21 |
| KG 825 | + | 0.05 g | 100 |

Hydrogenation of Dimethyl Itaconate 5 in Conventional Organic Solvents

Using 0.05 g of Wilkinson's catalyst in common organic solvents yielded poor percentage conversions.

TABLE D

Conversion of 5 to 9 in Common Organic Solvents

| Solvent | Conversion (%) to 9 |
|---|---|
| Dichloromethane | 7 |
| Toluene | 7 |
| Methanol | 11 |

Catalyst Recycling Effect

TABLE E

Recycled Catalyst Activity

[KG821]

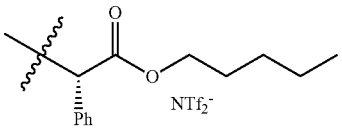

| Run | Conversion (%) |
|---|---|
| 1 | 36 |
| 2 | 56 |

TABLE E-continued

Recycled Catalyst Activity

[KG821]

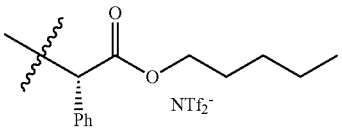

| Run | Conversion (%) |
|---|---|
| 3 | 71 |
| 4 | 75 |
| 5 | 76 |
| 6 | 85 |
| 7 | 73 |
| 8 | 73 |
| 9 | 69 |
| 10 | 64 |

It is possible that an activation period for the catalyst in the IL was necessary in this case to achieve high conversion which might explain why maximum conversion was only reached after 6 runs.

CIL as Additive to Achiral IL in Hydrogenation of Dimethyl Itaconate 5

The effect of CILs as additives was investigated. S(+) 3-methyl-1-(1-phenyl-1-pentoxycarbonyl)methyloxycarbonylmethylimidazolium bis(trifluoromethane)sulfonimide [KG 817] was investigated as an additive with 3-methyl-1-pentyloxycarbonylmethylimidazolium bis(trifluoromethane)sulfonimide achiral IL.

TABLE F

Conversion of 5 to 9 using CIL/IL Mixtures

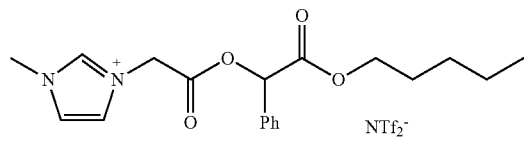

KG 817

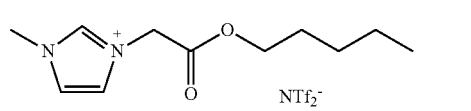

KG 48

| IL amount | CIL amount | Conversion (%) |
|---|---|---|
| 2 mL | — | 74 |
| — | 2 mL | 100 |
| 1.8 mL | 0.2 mL | 74 |
| 1.5 mL | 0.5 mL | 100 |

Hydrogenation Reactions of Acid 6
General Procedure
Hydrogenation Reaction of Tiglic Acid 6 in [NTf$_2$] IL [KG 831]

Reduction of tiglic acid led to the formation of chiral 2-methylbutanoic acid 10.

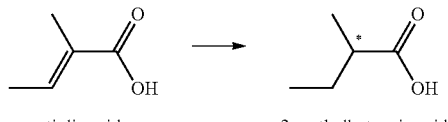

tiglic acid     2-methylbutanoic acid
6                10

Catalyst: 10% Pd—C or
Tris(triphenylphosphine)rhodium(I) Chloride
(Wilkinson's Catalyst) or PtO$_2$ (Adams' Catalyst)

The catalyst [(10% Pd/C, 5.0 mg, 0.12 mol %), (Tris(triphenylphosphine)rhodium(I) chloride, 0.05 g, 1.35 mol %), (PtO$_2$, 5.0 mg, 0.55 mol %)] was weighed into a dry 2-neck round bottom flask. The pre-dried IL [KG 831] (2.0 mL) was then added to the flask, followed by tiglic acid 6 (0.40 g, 4.00 mmol) and 3 N$_2$/vacuum cycles were performed.

The reaction mixture was stirred for 10 minutes or until reaching 55° C. (85° C. in the case of the Pd—C catalyst). Hydrogen was then introduced to the reaction via a balloon, and the progress of the reaction was monitored by $^1$H NMR. Upon termination of the reaction, the products were extracted using hexane (10×3 mL). The mass recovery after extraction from the IL was 100% (0.40 g). 2-Methylbutanoic acid was obtained in 81% yield (Pd—C), 22% conversion (Wilkinson's catalyst), or 98% yield (Adams' catalyst) (0.40 g, 3.92 mmol).

NMR: 2-Methylbutanoic Acid 10 Product $^1$H NMR (400 MHz, CDCl$_3$) δ ppm 11.58 (br s, 1H), 2.35 (q, J=7.2 Hz, 1H), 1.68-1.61 (m, 1H), 1.46-1.40 (m, 1H), 1.11 (d, J=7.2 Hz, 3H), 0.89 (t, J=7.4 Hz, 3H) $^{13}$C NMR (100 MHz, CDCl$_3$) δ ppm 183.71, 40.74, 26.51, 16.32, 11.51. Data consistent with literature values (M. Kawashima).

10% Palladium on carbon, Wilkinson's catalyst and Adams' catalyst were used to investigate the hydrogenation of this substrate 6 to product 10 in the novel CILs.

Catalyst: 10% Pd/C

TABLE G

Lactate CILs in Hydrogenation of Tiglic acid 6 to 2-methylbutanoic acid 10

| R | Chirality | Amount of catalyst 10% Pd/C | Temperature | Conversion (%) to 10 |
|---|---|---|---|---|
| KG 801 | +/− | 0.05 g | 55 | 0 |
|  |  | 0.05 g | 85 | 81 |
|  |  | 0.15 | 85 | 93 |

Catalyst: Wilkinson's Catalyst

TABLE H

Convention Solvents vs. Lactate CILs in Hydrogenation of Tiglic acid 6 to 2-methylbutanoic acid 10

| Solvent | Chirality | Conversion (%) to 10 |
|---|---|---|
| Methanol | − | 26 |
| Ethyl acetate | − | 8 |

TABLE H-continued

Convention Solvents vs. Lactate CILs in Hydrogenation of Tiglic acid 6 to 2-methylbutanoic acid 10

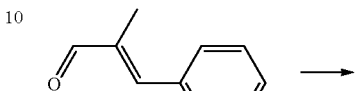

| Solvent | Chirality | Conversion (%) to 10 |
|---|---|---|
| KG 807 | − | 22 |

Catalyst: Adams' Catalyst

TABLE I

Mandelate CILs in Hydrogenation of Tiglic acid 6 to 12-methylbutanoic acid 10

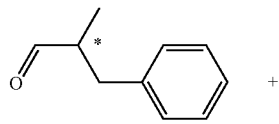

| R | Chirality | Conversion (%) to 10 |
|---|---|---|
| KG 823 | + | 100 |
| KG 821 | + | 100 |

Hydrogenation Reactions of α-Methyl-Trans-Cinnamaldehyde 8

The hydrogenation of this substrate led to a mixture of products.

α-methyl trans cinnamaldehyde
8

2-methyl-3-phenylpropanal
12

+

2-methyl-3-phenylpropanal-1-ol
13

Catalyst: 10% Pd/C

TABLE J

Hydrogenation Reactions of α-methyl-trans-cinnamaldehyde 8 in Achiral ILs:
(Selectivity refers to 2-methyl-3-phenylpropanal, 12)

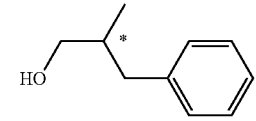

| R | Temperature | Selectivity (%) for 12 | Conversion (%) |
|---|---|---|---|
| Toluene | RT | 67 | 56 |
| KG 48 | 55 | 78 | 12 |

TABLE J-continued

Hydrogenation Reactions of α-methyl-trans-cinnamaldehyde 8 in Achiral ILs:
(Selectivity refers to 2-methyl-3-phenylpropanal, 12)

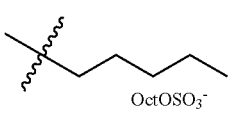

| R | Temperature | Selectivity (%) for 12 | Conversion (%) |
|---|---|---|---|
| 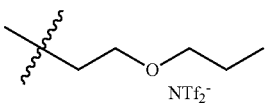<br>OctOSO$_3^-$<br>KG 35 | 80 | 100 | 11 |
| 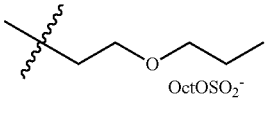<br>NTf$_2^-$<br>KG 51 | 55 | 0 | 0 |
| 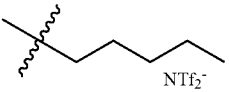<br>OctOSO$_2^-$<br>KG 38 | 55 | 0 | 0 |

Adams' Catalyst

TABLE K

Hydrogenation Reactions of α-methyl-trans-cinnamaldehyde 8 in CILs vs. Achiral IL:
(Selectivity refers to 2-methyl-3-phenylpropanal, 12)

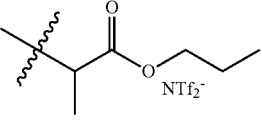

| R | Chirality | Selectivity (%) for 12 | Conversion (%) for 12 |
|---|---|---|---|
| 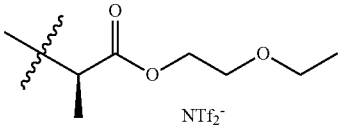<br>NTf$_2^-$<br>KG 48 |  | 55 | 77 |
| (structure)<br>NTf$_2^-$<br>KG 802 | +/− | 100 | 32 |
| (structure)<br>NTf$_2^-$<br>KG 811 | − | 100 | 22 |

TABLE K-continued

Hydrogenation Reactions of α-methyl-trans-cinnamaldehyde 8 in CILs vs. Achiral IL:
(Selectivity refers to 2-methyl-3-phenylpropanal, 12)

| R | Chirality Selectivity (%) for 12 | Conversion (%) for 12 |
|---|---|---|
| KG 821 | + | 0 | 0 |
| KG 831 | − | 100 | 22 |
| KG 817 | +/− | 100 | 34 |
| KG 835 | − | 100 | 4 |

Hydrogenation Reactions of α-acetamido cinnamic acid 7 to 2-acetamido-3-phenylpropanoic acid 11

The hydrogenation of α-acetamido cinnamic acid 7 led to a single product 2-acetamido-3-phenylpropanoic acid 11.

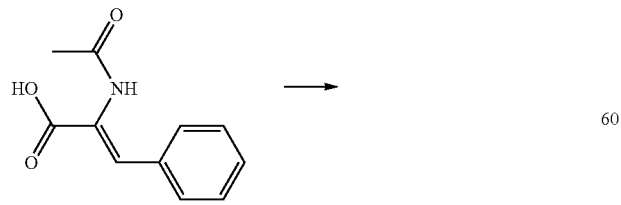

α-acetamido cinnamic acid
7

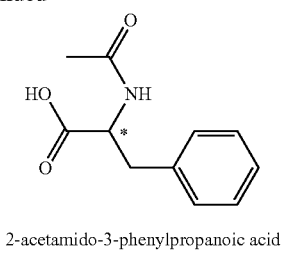

2-acetamido-3-phenylpropanoic acid
11

Catalyst: 10% Pd/C

After 48 hours using 10% Pd/C (0.22 mol %) catalyst, 100% conversion of substrate 7 to product 11 was obtained using all but one CIL tested thus far.

TABLE L

Hydrogenation Reactions of α-acetamide cinnamic acid 7 in CILs vs. Achiral IL vs Conventional Solvent:

| Solvent | Chirality | Conversion (%) to 11 |
|---|---|---|
| Ethyl acetate | – | 100 |
| 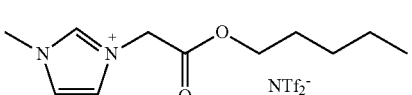 KG 48 | – | 100 |
| 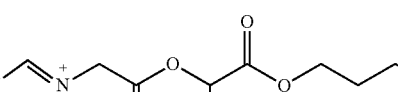 KG 804 | +/– | 100 |
| 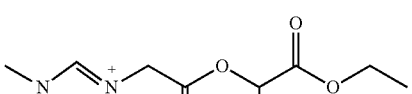 KG 821 | + | 0 |

Discussion of Hydrogenation Results (at 1 atm H₂ Gas Pressure)

Figure 1:
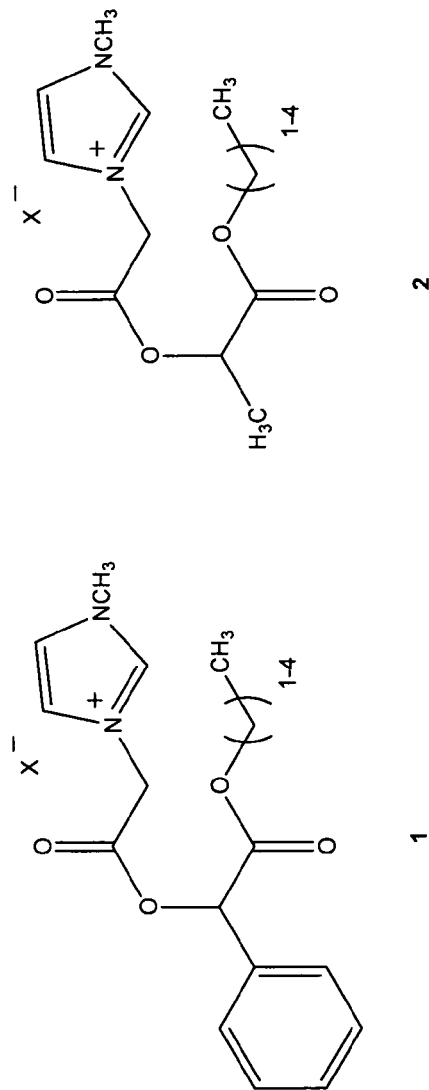
FIG. 1: Mandelate and Lactate CILs.

Ditriflimide (NTf$_2$), (low viscosity and high hydrophobicity) and also octylsulfate (OctOSO$_3$) (high biodegradability, low hydrophobicity) anions have been tested for catalytic stereo inducing ability in a hydrogenation reaction with each class of chiral lactate and mandelate ILs (1, 2 racemic and also enantiomerically pure forms) from the original library in FIG. 1. While the CILs tested did not give notable stereoinduction in all cases, substrate conversion and product selectivity where high in many cases using various prochiral substrates.

In the case of the lactate ILs 1, maximum conversion of substrate 5 to the reduced product 9 (100%) was achieved using either a propyl [KG 802, KG 808] or a pentyl [KG 804, KG 810] ester side chain and an NTf$_2$ counter anion at 55° C. in the presence of 22 mol % Pd—C catalyst.

With the mandelate chiral ILs, to achieve the same maximum conversion of 100% from substrate 5 to the reduced product 9, an ethyl ester side chain was used in conjunction with an NTf$_2$ counter anion. [KG 813]

Alternatively, under homogeneous conditions, Wilkinson's catalyst (chlorotris(triphenylphosphine)rhodium(I)— RhCl(PPh$_3$)$_3$) in conjunction with a mandelic acid based chiral IL containing a pentyl ester side chain and NTf$_2$ anion [KG 825] gave 9 in 100% conversion from substrate 5, with just 1.26 mol % catalyst.

Alternatively, under homogeneous conditions, Wilkinson's catalyst (chlorotris(triphenylphosphine)rhodium(I)— RhCl(PPh$_3$)$_3$) in conjunction with a mandelic acid based chiral IL containing a pentyl ester side chain and NTf$_2$ anion gave 9 in 100% conversion from substrate 5, with just 1.26 mol % catalyst.

Surprisingly, this conversion significantly surpassed that achieved in conventional solvents such as methanol (11%), DCM (7%) and toluene (7%). When the chiral IL was admixed with an economical achiral IL in a ratio of 3:1 (achiral/chiral) it was still possible to achieve 100% conversion to 9.

For the sterically hindered double bond of tiglic acid 6, a slightly lower conversion of 93% was achieved using Pd—C at 55° C., combining an ethyl ester side-chain with NTf$_2$ anion [lactate ILs] [KG 801] However, a PtO$_2$ catalyst increased the conversion of tiglic acid 6 into product 10 to 100% with either an ethyl [KG 821], or butyl ester side-chain [KG 823]. The excellent conversion was unexpected, since with this hindered substrate, Wilkinson's catalyst proved relatively ineffective at atmospheric hydrogen pressure (22% conversion/lactate IL, ethyl ester/NTf$_2$ [KG 807]).

With substrate α-methyl-trans-cinnamaldehyde 8 the reaction becomes more interesting because two possible products can be formed during the hydrogenation reaction, either that of carbon-carbon double bond reduction to provide product 12, or that of further reduction of the carbonyl group of substrate 8 to provide product 13.

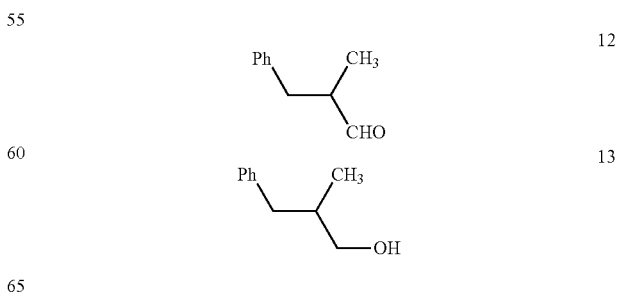

In practice, using Pd—C and hydrogen, it was possible to form only product 12 (as a racemic mixture) by a 100% selective reduction at 80° C. with 3-methyl-1-pentyloxycarbonylmethylimidazolium octylsulfate, an achiral ionic liquid [KG 35]. Nevertheless, while this selectivity exceeds that in the conventional solvent, toluene (67% selectivity for product 12), the conversion (11%) is lower than that seen in toluene (56% in toluene). However, using $PtO_2$ as catalyst it was possible to maintain 100% selectivity for product 12, yet increase the conversion to 34% with a mandelate-based IL as the pentyl ester, with an $NTf_2$ counter ion [KG 817].

(Z)-α-(N-acetamido)cinnamic acid 3 proved to be a relatively straightforward substrate, at least as far as conversion is concerned, with lactate (butyl side-chain) [KG 804] or the achiral ionic liquid with a pentyl ester chain, [KG 48] (both $NTf_2$ salts matching the 100% conversion achieved at atmospheric hydrogen pressure in ethyl acetate after 48 hours, using Pd—C as a heterogeneous catalyst.

Stereoselectivity and Aromatic Ring Reduction

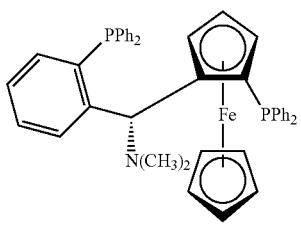

Taniaphos SL-T001-1
(2S)-1-[(R)-(Dimethylamino)[2-(diphenylphosphino)phenyl]methyl]-2-(diphenylphosphino)ferrocene In a further experiment, the methyl ester substrate of substrate 7, (methyl α-acetamidocinnamate 14) was successfully reduced to product 15 using the asymmetric homogeneous catalyst, derived from the ligand (S)-1-diphenylphosphino-2-[(R)-α-(dimethylamino)-2-(diphenylphosphino)benzyl] ferrocene (Taniaphos SL-T001-1) combined with bis(norbornadiene) rhodium(I) tetrafluoroborate. Chiral GC was used to determine the enantiomeric excess of product formed.

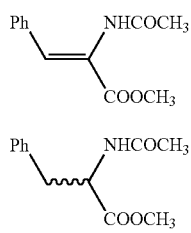

Generally pressures of 3 Atm or more may be required for this reaction. In this case though, (Taniaphos) reduction at 1 atm (the Taniaphos system has previously been demonstrated to be highly enantioselective at 1 atm in methanol, (Spindler et al.), it is a significant result because the products were produced enantiomerically enriched in the low toxicity and high biodegradability ionic liquid.

The enantiomeric excesses achieved when using the Taniaphos chiral catalyst system together with the panel of prochiral substrates were modest (at best 40% ee, in the reduction of dimethyl itaconate, 9, determined by chiral HPLC using a Daicel CHIRALPAK® IB column).

Chromatography Columns and Conditions Used for Product Analysis

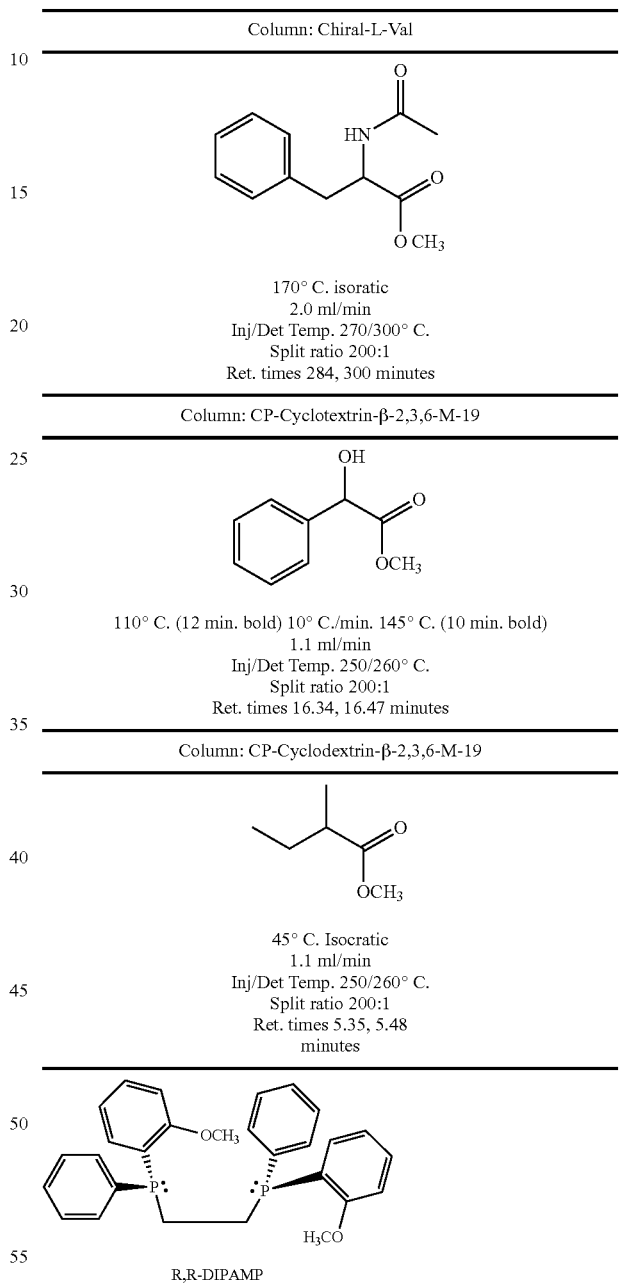

Asymmetric Hydrogenation Catalyst,
[(R,R)-DiPAMP-Rh(COD)][BF_4]

Figure 5:
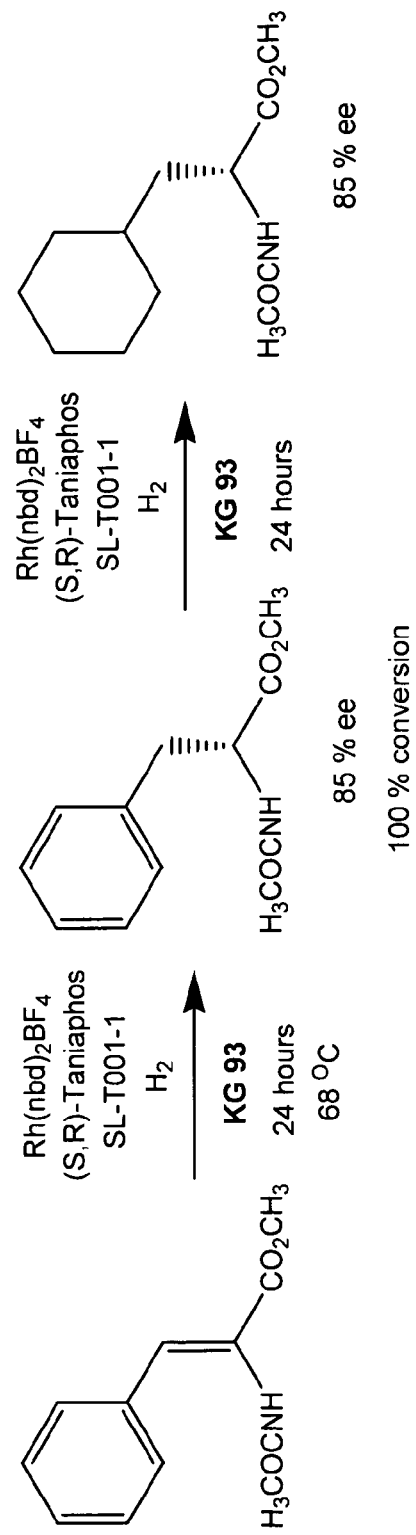
FIG. 5: Hydrogenation of Methyl α-acetoamidocinnamate in CIL derived from (R)-methyl mandelate as $NTf_2$ salt [KG 93]

Both Taniaphos and DiPAMP-based chiral catalysts give high enantiomeric excesses (76-93%) in the reduction of α-acetamido cinnamic acid methyl ester 14 (FIGS. 4, 5 and Table M).

GC analysis indicates the formation of a smaller co-product resulting from the surprising reduction of an aromatic system (in α-acetamido cinnamate methyl ester) under 1 atmosphere of hydrogen using the Taniaphos catalyst system (FIG. 5). This only occurs using either (S) or (R) 3-methyl-1-(methylmandelatecarbonylmethyl)imidazolium bis(trifluoromethane)sulfonlmide [KG 93/94] as a solvent. The hydrogenation of aromatic systems would normally be a very difficult transformation and has been reported to require the presence of Ru(0) nanoparticles of the catalyst to occur at atmospheric pressure (Prechtl). Only the combination of the Taniaphos system and the chiral IL gave the aromatic reduction product. This reaction, which requires one extra day's catalytic reduction, demonstrates a marked increase in reactivity when using a chiral ionic liquid, especially considering that it unusually occurs at only 1 atmosphere of hydrogen, potentially giving rise to industrial processes that are more energy-efficient, safer and greener.

Hydrogenation of methyl α-acetamidocinnamate 14 using Rh Taniaphos and Rh DiPAMP homogeneous chiral catalysts, gave conversions ranging from 0-100%, with an optimum ee of 75.6% at 87.8% conversion using Rh DiPAMP and (S)-3-methyl-1-(1-phenyl-1-methoxycarbonylmethyl)imidazolium bis(trifluoromethane)sulfonimide KG94 as solvent after 42 h reaction at 88° C. (Table M). The same reaction with Rh Taniaphos and either (S) or (R)-3-methyl-1-(1-phenyl-1-methoxycarbonylmethyl)imidazolium bis(trifluoromethane) sulfonlmide [KG 93/94] gave the opposite enantiomer in excess, together with a second product resulting from reduction of the aromatic ring (GC-MS analysis gives mass ions consistent with hydrogenation of the aromatic system to a substituted cyclohexane) when the reaction is run to high conversion. (FIGS. 4, 5 and Table M).

GC analysis indicated that along with the expected acetamide of D-phenylalanine methyl ester the reaction mixture contained two isomeric forms of the starting material (Retention Time=15.1 and 10.75 min) (Z and E-isomers) as well as two enantiomeric forms of the aromatic-reduced product, (Retention Time=8 and 9 min) in the same ratio as the desired product.

Discussion of Hydrogenation Reaction at Hydrogen Gas Pressure Above 1 Atmosphere (50 psi)

The CIL KG90 gave an increase in ee (93.2%) for the product compared to MeOH as the solvent (92.4%). This demonstrates that the chiral ionic liquid solvent can be tailored to a catalyst to give an improved enantioselectivity compared to MeOH. The other enteries in the table above show that the structure of the CIL is important for an increase in enantioselectivity. KG 56 and KG 806 show that opposite enantiomers can lead to different degrees of enantioinduction conferred by the catalyst. The achiral IL KG 56 gave the lowest level of enantioselectivity with the chiral catalyst in the table above. We submit that chiral ionic liquids contained within this patent can be useful solvents or additives for asymmetric induction.

TABLE M

Enantioselective Hydrogenation of methyl alpha-acetamidocinnamate 14 using CILs vs ILs

| Substrate | Catalyst | Solvent | Temp | Time | Conversion to 15 |
|---|---|---|---|---|---|
| methyl α-acetamidocinnamate 0.21 g (0.961 mmol) | (S)-Ru(OAc)$_2$ (T-BINAP) 4.2 mg 4.68 μmoles | Achiral IL: 3-methyl-1-(pentoxycarbonylmethyl) imidazolium NTf$_2$ KG 48 –0.75 ml | 83° C. | 4 days | No reaction |
| methyl α-acetamidocinnamate 0.163 g (0.75 mmol) | Rh Taniaphos SL-T001-1 2.0 mg Rh(nbd)$_2$BF$_4$ 4.3 mg SL-T001-1 5.35 μmoles | Achiral IL: 3-methyl-1-(pentoxycarbonylmethyl) imidazolium NTf$_2$ KG 48 0.75 ml | 86° C. | 5 days | 22% conversion ee: 80.2% (D enantiomer major product) |
| methyl α-acetamidocinnamate 0.074 g (0.34 mmol) | Rh Taniaphos SL-T001-1 2.2 mg Rh(nbd)$_2$BF$_4$ 4.2 mg SL-T001-1 5.88 μmoles | Chiral IL: (S)-3-methyl-1-(1-phenyl-1-methoxycarbonylmethyl)imidazolium NTf$_2$ KG 94 0.21 g | 68° C. | 42 hours | 100% conversion ee: 75.6% (D enantiomer major product) [also minor product of reduced aromatic ring] |
| methyl α-acetamidocinnamate 0.100 g (0.40 mmol) | Rh Taniaphos SL-T001-1 3.3 mg Rh(nbd)$_2$BF$_4$ 5.4 mg SL-T001-1 8.82 μmoles | Chiral IL: (R)-3-methyl-1-(1-phenyl-1-methoxycarbonylmethyl)imidazolium NTf$_2$ KG 93 0.43 g | 95° C. | 20 hours | 100% conversion ee: 85.0% (D enantiomer major product) [also minor product of reduced aromatic ring] |
| methyl α-acetamidocinnamate 0.109 g (0.50 mmol) | [(R,R)-DiPAMP-Rh(cod)] BF$_4$ 14 mg 18.54 μmoles | Chiral IL: (S)-3-methyl-1-(1-phenyl-1-methoxycarbonylmethyl)imidazolium NTf$_2$ KG 94 0.32 g | 88° C. | 42 hours | 94% conversion ee: 87.8% (L enantiomer major product) |
| methyl α-acetamidocinnamate 0.075 g (0.34 mmol) | [(R,R)-DiPAMP-Rh(cod)] BF$_4$ 4.3 mg 5.70 μmoles | Chiral IL: (R)-3-methyl-1-(1-phenyl-1-methoxycarbonylmethyl)imidazolium NTf$_2$ KG 93 0.56 g | 86° C. | 20 hours | 50% conversion ee: 80.8% (L enantiomer major product) |

T-BINAP: 2,2'-bis(diphenylphosphino)-1,1'-binaphthyl: Rh Taniaphos: [(S)-1-Diphenylphosphino-2-[(α-(R)-N,N-dimethylamino)-(o-diphenylphosphinophenyl)-methyl]-ferrocene-(1,5-cyclooctadiene)-rhodium(I)]-tetrafluoroborate Hydrogenation Reaction Conditions at Hydrogen
Gas Pressure Above 1 Atmosphere (50 psi)

| Substrate | Ionic Liquid | Temp/Pressure | Run Time | Conversion[a] | ee for 17[b,c] |
|---|---|---|---|---|---|
| 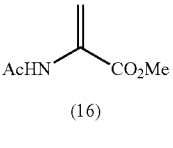 (16) | 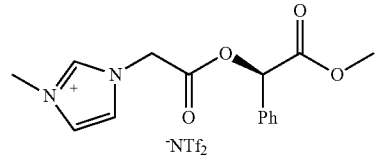 KG 93 | 80° C./50 psi | Complete (<0.5 h) | >95% | 93.2% (S) |
| | 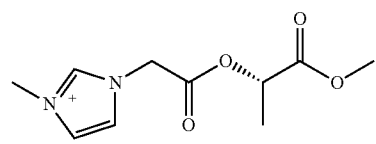 KG 2018 | 80° C./50 psi | Complete (<0.5 h) | >95% | 84.4% (S) |
| | 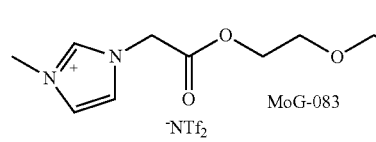 KG 56 | 80° C./50 psi | Complete (<0.5 h) | >95% | 82.0% (S) |
| | 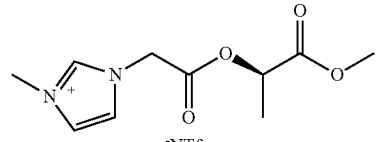 KG 806 | 80° C./50 psi | Cpmplete (<0.5 h) | >95% | 89.2% (S) |
| | MeOH | 80° C./50 psi | Complete (<0.5 h) | >95% | 92.4% (S) |

Notes:
[a]Conversion determined to by $^1$H NMR using integration of $CH_3$ of N—Ac group;
[b]ee at 210 nm determined using HPLC;
[c]major enantiomer assignment based on literature precedent

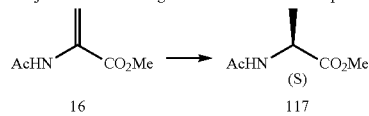

16 → 117

Conditions:
Catalyst: 0.5 mol % [((R,R)-DiPAMP)Rh(cod)]BF$_4$:
Solvent: 2 mL (2 g for solid IL)
Temp.: 80° C.
Substrate: α-acetamidocinnamic acid methyl ester, 1 mmol
H$_2$: 50 psi
Stirring: 400 rpm

Biodegradability & Toxicity

The biodegradability of the ILs can be evaluated applying the following standard methods: (i) Sturm Test (ii) Closed Bottle Test (OECD 301D) (iii) CO$_2$ Headspace Test (ISO 14593). Both tests (ii) and (iii) are included in the European Regulation (EC) No 648/2004 of biodegradability of detergent surfactants, the CO$_2$ Headspace Test being the reference method for laboratory testing of ultimate biodegradability. In the Closed Bottle and CO$_2$ Headspace tests, the compound to be evaluated is added to an aerobic aqueous medium inoculated with wastewater microorganisms and the depletion of dissolved O$_2$ or the CO$_2$ evolution is measured periodically and reported as a percentage of theoretical maximum. Sodium n-dodecyl sulfate (SDS) is generally used as a reference substance. An IL will be considered "readily biodegradable" and, therefore it will be assumed that such a chemical will be rapidly and completely biodegraded in an aquatic environment under aerobic conditions, if the biodegradation level measured according to one of the described tests is higher than 60% within 28 days.

IL toxicity tests are based on systems with different biological complexity levels. The toxicity of the ILs has been measured on a wide range of organisms from bacteria and fungi, to higher organisms such as zebrafish, the soil nematode and the freshwater snail. LC50, IC50, EC50 and MIC values are used as a measurement of the toxicity of the ILs on the organism. Growth inhibition studies have also been carried out on algae and terrestrial plants. Such tests indicate the levels at which the IL in a biological system prevents or disrupts growth. Data from such studies on ILs can then be compared to well known values for common organic solvents. In general the toxicity of ionic liquids tested to date is found to be some orders of magnitude higher than that of conventional solvents such as acetone and methanol. A common problem with the toxicity of ionic liquids is associated with the presence of an extended hydrocarbon chain. The length of the side chains was found to influence the dialkylimidazolium ionic liquid's toxicity, with longer chain length proving to be more toxic. In fact, Bodor et al. (9) have shown that the long chain ester derivatives of methyl imidazole show effective antimicrobial activity at ppm concentrations, clearly demonstrating the toxic effect of such ILs on microbes.

Biological Testing of Chiral Ionic Liquids

All the 12 bromide salts and 12 octylsulfate CILs in the table below were screened against fungi and bacteria.

CILs with bromide as anion have been screened against the following Fungi and bacteria:

| Fungi |
| --- |
| 1. CA1 *Candida albicans* ATCC 44859 |
| 2. CA2 *Candida albicans* ATCC 90028 |
| 3. CP *Candida parapsilosis* ATCC 22019 |
| 4. CK1 *Candida krusei* ATCC 6258 |
| 5. CK2 *Candida krusei* E28 |
| 6. CT *Candida tropicalis* 156 |
| 7. CG *Candida glabrata* 20/1 |
| 8. CL *Candida lusitaniae* 2446/1 |
| 9. TB *Trichosporon beigelii* 1188 |
| 10. AF *Aspergillus fumigatus* 231 |
| 11. AC *Absidia corymbifera* 272 |
| 12. TM *Trichophyton mentagrophytes* 445 |

| Bacteria | |
| --- | --- |
| 1. SA *Staphylococcus aureus* CCM 4516/08 | |
| 2. MRSA *Staphylococcus aureus* H 5996/08 | Methiciline-resistant |
| 3. SE *Staphylococcus epidermidis* H 6966/08 | |
| 4. EF *Enterococcus* sp. J 14365/08 | |
| 5. EC *Escherichia coli* CCM4517 | |
| 6. KP *Klebsiella pneumoniae* D 11750/08 | |
| 7. KP-E *Klebsiella pneumoniae* J 14368/08 | ESBL-positive |
| 8. PA *Pseudomonas aeruginosa* CCM 1961 | |

| Mandelate derivatives | IL no. | R | Configuration |
| --- | --- | --- | --- |
| (Br⁻, imidazolium-CH₂-C(O)O-CH(Ph)-C(O)OR) | KG818 | $C_2H_4OC_2H_5$ | RS |
| | KG833 | $C_5H_{11}$ | R |
| | KG826 | $C_2H_4OC_2H_5$ | S |
| | KG824 | $C_5H_{11}$ | S |
| | KG816 | $C_5H_{11}$ | RS |
| | KG90 | $CH_3$ | R |
| | KG89 | $CH_3$ | RS |
| | KG91 | $CH_3$ | S |
| | KG835 | $C_2H_4OC_2H_5$ | R |

| Lactate derivatives | IL no. | R | Configuration |
| --- | --- | --- | --- |
| (Br⁻, imidazolium-CH₂-C(O)O-CH(Me)-C(O)OR) | KG160 | $C_2H_4OC_2H_5$ | RS |
| | KG159 | $C_5H_{11}$ | R |
| | KG161 | $C_2H_4OC_2H_5$ | R |

| Mandelate derivatives | IL no. | R | Configuration |
| --- | --- | --- | --- |
| (OctOSO₃⁻, imidazolium-CH₂-C(O)O-CH(Ph)-C(O)OR) | KG400 | $C_2H_4OC_2H_5$ | RS |
| | KG303 | $C_5H_{11}$ | R |
| | KG305 | $C_2H_4OC_2H_5$ | S |
| | KG302 | $C_5H_{11}$ | S |
| | KG304 | $C_5H_{11}$ | RS |
| | KG87 | $CH_3$ | R |
| | KG86 | $CH_3$ | RS |
| | KG88 | $CH_3$ | S |
| | KG301 | $C_2H_4OC_2H_5$ | R |

| Lactate derivatives | IL no. | R | Configuration |
| --- | --- | --- | --- |
| (OctOSO₃⁻, imidazolium-CH₂-C(O)O-CH(Me)-C(O)OR) | KG172 | $C_2H_4OC_2H_5$ | RS |
| | KG171 | $C_5H_{11}$ | R |
| | KG173 | $C_2H_4OC_2H_5$ | R |

In vitro antifungal activities of the compounds were evaluated on the collection of fungal strains deposited at the Department of Biological and Medical Sciences, Faculty of Pharmacy, Charles University, Czech Republic. All the isolates were maintained on Sabouraud dextrose agar prior to being tested.

Minimum inhibitory concentrations (MICs) were determined by the microdilution format of the NCCLS M27-A guidelines. Dimethyl sulfoxide served as a diluent for all compounds; the final concentration did not exceed 2%. RPMI 1640 (Sevapharma, Prague) medium supplemented with L-glutamine and buffered with 0.165 M morpholinepropanesulfonic acid to pH 7.0 was used as the test medium. The wells of the microdilution tray contained 100 µl of the RPMI 1640 medium with 2-fold serial dilutions of the compounds (1000 to 0.24 µmol/l for the new compounds) and 100 µl of inoculum suspension. Fungal inoculum in RPMI 1640 was prepared to give a final concentration of $5\times10^3\pm0.2$ cfu·ml-1. The trays were incubated at 35° C. and MICs were read visually for filamentous fungi and photometrically for yeasts as an optical density (OD) at 540 nm after 24 h and 48 h. The MICs were defined as 80% inhibition of the growth of control. MICs were determined twice and in duplicate. The deviations from the usually obtained were no higher than the nearest concentration value up and down the dilution scale.

| Results against Fungi | | | | | | | | | | | | | |
|---|---|---|---|---|---|---|---|---|---|---|---|---|---|
| Fungi | | Samples-MIC/IC$_{80}$ (µmol·l$^{-1}$) | | | | | | | | | | | |
| | (hr) | KG89 | KG90 | KG91 | KG816 | KG833 | KG824 | KG835 | KG826 | KG818 | KG160 | KG159 | KG161 |
| CA1 | 24 h | >1000 | >1000 | >1000 | 500 | 500 | 500 | >1000 | >1000 | >1000 | >1000 | >1000 | >1000 |
| | 48 h | >1000 | >1000 | >1000 | 1000 | >1000 | >1000 | >1000 | >1000 | >1000 | >1000 | >1000 | >1000 |
| CA2 | 24 h | >1000 | >1000 | >1000 | 1000 | 1000 | 1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| CP | 24 h | >1000 | >1000 | >1000 | >1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| CK1 | 24 h | >1000 | >1000 | >1000 | 1000 | 1000 | 1000 | >1000 | >1000 | >1000 | >1000 | >1000 | >1000 |
| | 48 h | >1000 | >1000 | >1000 | 1000 | >1000 | >1000 | >1000 | >1000 | >1000 | >1000 | >1000 | >1000 |
| CK2 | 24 h | >1000 | >1000 | >1000 | 1000 | 1000 | 1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| CT | 24 h | >1000 | >1000 | >1000 | 1000 | 1000 | 1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| CG | 24 h | >1000 | >1000 | >1000 | 1000 | 1000 | 1000 | >1000 | >1000 | >1000 | >1000 | >1000 | >1000 |
| | 48 h | >1000 | >1000 | >1000 | 1000 | >1000 | >1000 | >1000 | >1000 | >1000 | >1000 | >1000 | >1000 |
| CL | 24 h | >1000 | >1000 | >1000 | >1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| TB | 24 h | >1000 | >1000 | >1000 | 1000 | 1000 | 1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| AF | 24 h | >1000 | >1000 | >1000 | 1000 | 1000 | 1000 | >1000 | >1000 | >1000 | >1000 | >1000 | >1000 |
| | 48 h | >1000 | >1000 | >1000 | 1000 | 1000 | 1000 | >1000 | >1000 | >1000 | >1000 | >1000 | >1000 |
| AC | 24 h | >1000 | >1000 | >1000 | 1000 | 1000 | 1000 | >1000 | >1000 | >1000 | >1000 | >1000 | >1000 |
| | 48 h | >1000 | >1000 | >1000 | 1000 | 1000 | 1000 | >1000 | >1000 | >1000 | >1000 | >1000 | >1000 |
| TM | 72 h | >1000 | >1000 | >1000 | 500 | 500 | 500 | >1000 | >1000 | >1000 | >1000 | >1000 | >1000 |
| | 120 h | >1000 | >1000 | >1000 | 500 | 500 | 500 | >1000 | >1000 | >1000 | >1000 | >1000 | >1000 |

Note:
X (µl) + Y (medium, ml):
Max concent. of sample mol.L−1/DMSO (%):
X = Amount (mg) + DMSO (l)

The CILs bromides have also been screened against the following bacteria:

| Results against Bacteria | | | | | | | | | | | | | |
|---|---|---|---|---|---|---|---|---|---|---|---|---|---|
| Bacteria | | Samples - MIC/IC$_{80}$ (µmol·l$^{-1}$) | | | | | | | | | | | |
| | (hrs) | KG89 | KG90 | KG91 | KG816 | KG833 | KG824 | KG835 | KG826 | KG818 | KG160 | KG159 | KG161 |
| SA | 24 h | >1000 | >1000 | >1000 | 1000 | 1000 | >1000 | >1000 | >1000 | >1000 | >1000 | >1000 | >1000 |
| | 48 h | >1000 | >1000 | >1000 | 1000 | >1000 | >1000 | >1000 | >1000 | >1000 | >1000 | >1000 | >1000 |
| MRSA | 24 h | >1000 | >1000 | >1000 | >1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| SE | 24 h | >1000 | >1000 | >1000 | >1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| EF | 24 h | >1000 | >1000 | >1000 | >1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| EC | 24 h | >1000 | >1000 | >1000 | >1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| KP | 24 h | >1000 | >1000 | >1000 | >1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| KP-E | 24 h | >1000 | >1000 | >1000 | >1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| PA | 24 h | >1000 | >1000 | >1000 | >1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |

The octylsulfate CILs have also been screen against all above fungi and bacteria. Results in Tables below:

Results against Fungi

| Fungi | | \multicolumn{12}{c}{Samples-MIC/IC$_{80}$ ($\mu mol \cdot l^{-1}$)} | | | | | | | | | | | |
|---|---|---|---|---|---|---|---|---|---|---|---|---|---|
| | (hr) | KG86 | KG87 | KG88 | KG303 | KG302 | KG304 | KG301 | KG305 | KG400 | KG172 | KG171 | KG173 |
| CA1 | 24 h | >1000 | >1000 | >1000 | 500 | 1000 | 1000 | >1000 | >1000 | >1000 | >1000 | >1000 | >1000 |
| | 48 h | >1000 | >1000 | >1000 | >1000 | 1000 | 1000 | >1000 | >1000 | >1000 | >1000 | >1000 | >1000 |
| CA2 | 24 h | >1000 | >1000 | >1000 | 1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| CP | 24 h | >1000 | >1000 | >1000 | >1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| CK1 | 24 h | >1000 | 1000 | >1000 | 1000 | >1000 | 1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| CK2 | 24 h | >1000 | 1000 | >1000 | 1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| CT | 24 h | >1000 | >1000 | >1000 | >1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| CG | 24 h | >1000 | >1000 | >1000 | >1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| CL | 24 h | >1000 | >1000 | >1000 | >1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| TB | 24 h | >1000 | >1000 | >1000 | 1000 | 1000 | 500 | >1000 | >1000 | >1000 | >1000 | >1000 | >1000 |
| | 48 h | >1000 | >1000 | >1000 | 1000 | >1000 | >1000 | >1000 | >1000 | >1000 | >1000 | >1000 | >1000 |
| AF | 24 h | >1000 | >1000 | >1000 | 1000 | 1000 | 500 | >1000 | >1000 | >1000 | >1000 | >1000 | >1000 |
| | 48 h | >1000 | >1000 | >1000 | 1000 | >1000 | >1000 | >1000 | >1000 | >1000 | >1000 | >1000 | >1000 |
| AC | 24 h | >1000 | >1000 | >1000 | 1000 | 1000 | 1000 | >1000 | >1000 | >1000 | >1000 | >1000 | >1000 |
| | 48 h | >1000 | >1000 | >1000 | 1000 | >1000 | 1000 | >1000 | >1000 | >1000 | >1000 | >1000 | >1000 |
| TM | 72 h | >1000 | 1000 | >1000 | 250 | 250 | 250 | >1000 | >1000 | >1000 | >1000 | >1000 | >1000 |
| | 120 h | >1000 | >1000 | >1000 | 500 | 500 | 500 | >1000 | >1000 | >1000 | >1000 | >1000 | >1000 |

Results against Bacteria

| Bacteria | | \multicolumn{12}{c}{Samples - MIC/IC$_{80}$ ($\mu mol \cdot l^{-1}$)} | | | | | | | | | | | |
|---|---|---|---|---|---|---|---|---|---|---|---|---|---|
| | (hrs) | KG86 | KG87 | KG88 | KG303 | KG302 | KG304 | KG301 | KG305 | KG400 | KG172 | KG171 | KG173 |
| SA | 24 h | >1000 | >1000 | >1000 | 1000 | >1000 | 1000 | >1000 | >1000 | >1000 | >1000 | >1000 | >1000 |
| | 48 h | >1000 | >1000 | >1000 | 1000 | >1000 | 1000 | >1000 | >1000 | >1000 | >1000 | >1000 | >1000 |
| MRSA | 24 h | >1000 | >1000 | >1000 | 1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| SE | 24 h | >1000 | >1000 | >1000 | 500 | 1000 | 1000 | >1000 | >1000 | >1000 | >1000 | >1000 | >1000 |
| | 48 h | >1000 | >1000 | >1000 | 1000 | >1000 | >1000 | >1000 | >1000 | >1000 | >1000 | >1000 | >1000 |
| EF | 24 h | >1000 | >1000 | >1000 | >1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| EC | 24 h | >1000 | >1000 | >1000 | >1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| KP | 24 h | >1000 | >1000 | >1000 | >1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| KP-E | 24 h | >1000 | >1000 | >1000 | >1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |
| PA | 24 h | >1000 | >1000 | >1000 | >1000 | >1000 | >1000 | >1000 | >1000 | >1000 | >1000 | >1000 | >1000 |
| | 48 h | >1000 | >1000 | >1000 | >1000 | >1000 | >1000 | >1000 | >1000 | >1000 | >1000 | >1000 | >1000 |

Toxicity of Imidazolium CILs

For all these chiral ionic liquids, only the pentyl side chain mandelate CILs (KG302, KG303 and KG304) were found to inhibit the growth of fungi and bacteria. Introducing oxygen functionality in side chain did not lead to increased toxicity. All lactate CILs were found to be non-toxic.

Toxicity of Pyridinium CILs

KG 2013 and KG 2015 screened against 5 bacteria strains: *Pseudomonas Putida* (CP1), *Pseudomonas Putida* (KT2440), *Escherichia Coli*, *Bacillus Subtilis*, and *Pseudomonas Fluorescens*. KG 1043 screened against 4 strains *Pseudomonas Putida* (CP1), *Pseudomonas Putida* (KT2440), *Escherichia Coli*, and *Pseudomonas Fluorescens*. All 3 pyridinium ionic liquids have low antimicrobial toxicity (IC50>1 mM).

| | IC50 values ($\mu M$) | | |
|---|---|---|---|
| Bacteria | KG 1043 | KG 2013 | KG 2015 |
| E. Coli | >1000 | >1000 | >1000 |
| B. Subtilis | nd[a] | >1000 | >1000 |
| P. Fluorescens | >1000 | >1000 | >1000 |
| P. Putida (CP1) | >1000 | >1000 | >1000 |
| P. Putida (KT2440) | >1000 | >1000 | >1000 |

[a]nd = not determined.

Biodegradable CIL

Figure 2:
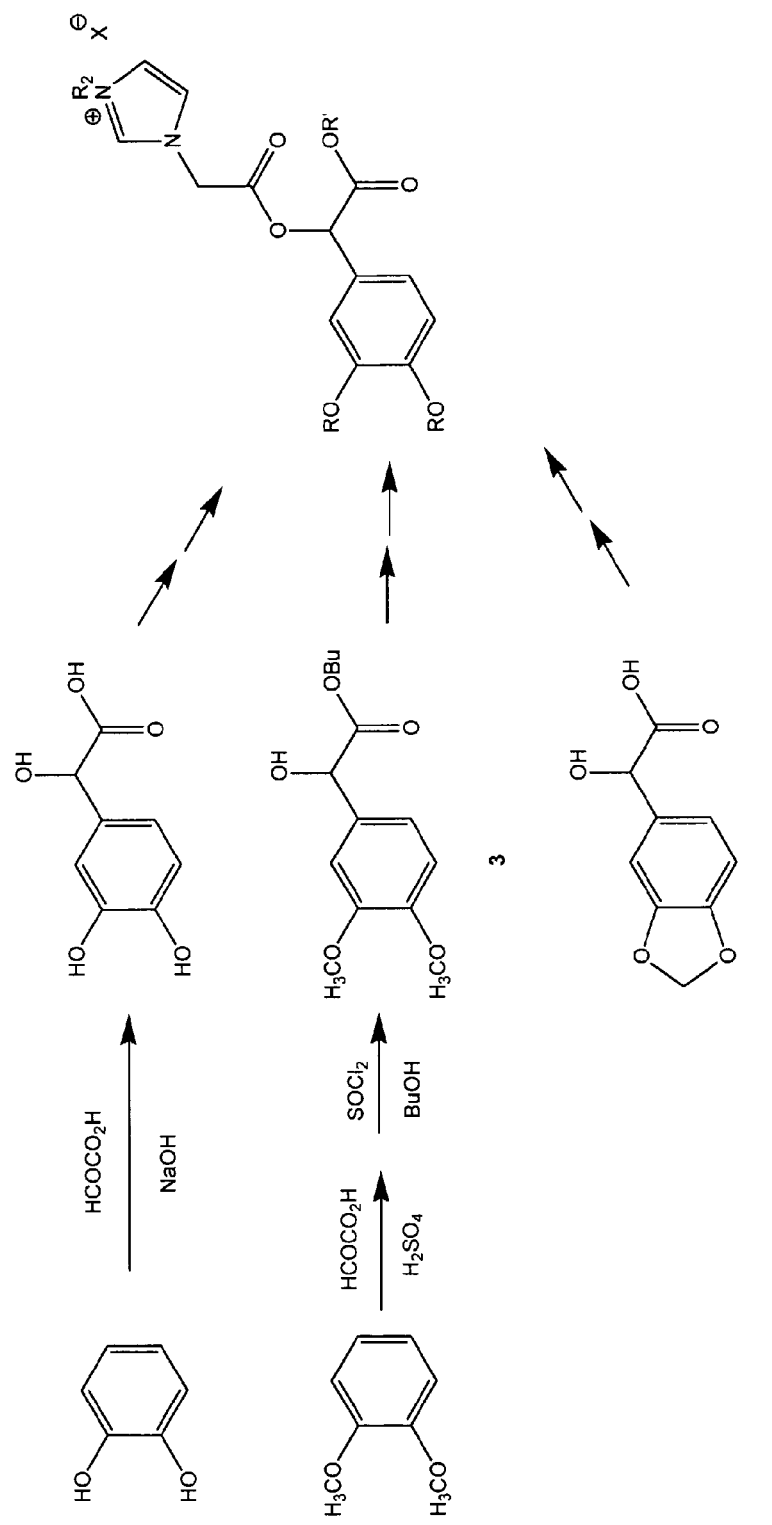
FIG. 2: Library of CILs.
Figure 3:
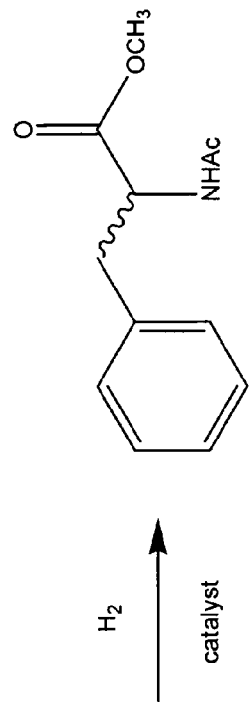
FIG. 3: Enantioselective Hydrogenation of Methyl α-acetoamidocinnamate.
Figure 3:
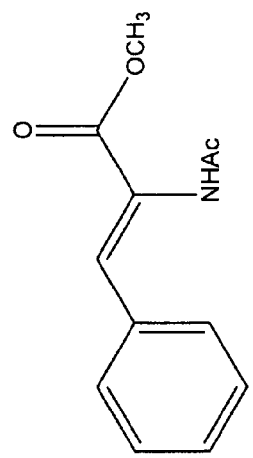

FIGS. 1 and 2 and Tables N and O demonstrate that all of the tested lactate and madelate based CILs compounds having $OctOSO_3^-$ anions are biodegradable, since they satisfy the requirement that biodegradability is higher than 60% within 28 days using the $CO_2$ Headspace Test.

TABLE N

| | % biodegradation lactate CILS | | | | |
|---|---|---|---|---|---|
| | | Days | | | |
| Compound | 0 | 6 | 14 | 21 | 28 |
| SDS | 0 | 81 | 88 | 90 | 92 |
| KG 162 | 0 | 46 | 57 | 61 | 64 |
| KG 163 | 0 | 49 | 60 | 63 | 67 |
| KG 166 | 0 | 50 | 63 | 66 | 67 |
| KG 167 | 0 | 51 | 62 | 69 | 69 |
| KG 170 | 0 | 52 | 65 | 72 | 72 |
| KG 171 | 0 | 54 | 67 | 70 | 71 |

TABLE N-continued

| | % biodegradation lactate CILS | | | | |
|---|---|---|---|---|---|
| | | Days | | | |
| Compound | 0 | 6 | 14 | 21 | 28 |
| KG 172 | 0 | 55 | 64 | 69 | 69 |
| KG 173 | 0 | 59 | 69 | 74 | 74 |

TABLE O

| | % biodegradation mandelate CILs | | | | |
|---|---|---|---|---|---|
| | | Days | | | |
| Compound | 0 | 6 | 14 | 21 | 28 |
| SDS | 0 | 84 | 87 | 90 | 88 |
| KG 301 | 0 | 63 | 73 | 78 | 80 |
| KG 302 | 0 | 66 | 76 | 81 | 79 |
| KG 303 | 0 | 62 | 72 | 77 | 79 |
| KG 304 | 0 | 64 | 78 | 79 | 82 |
| KG 305 | 0 | 73 | 77 | 85 | 83 |
| KG 306 | 0 | 66 | 75 | 83 | 82 |
| KG 308 | 0 | 62 | 71 | 78 | 78 |

TABLE P

Library of 118 Chiral salts prepared

| Ionic Liquid | $Br^-$ | $NTf_2^-$ | $OctOSO_3^-$ |
|---|---|---|---|
| (methyl lactate imidazolium structure) | KG 150 | KG 800 | KG 162 |
| (ethyl lactate imidazolium structure) | KG 152 | KG 801 | KG 164 |
| (propyl lactate imidazolium structure) | KG 154 | KG 802 | KG 166 |
| (butyl lactate imidazolium structure) | KG 156 | KG 803 | KG 168 |

TABLE P-continued

Library of 118 Chiral salts prepared

| Structure | | | |
|---|---|---|---|
| (1-methylimidazolium-N-CH₂-C(O)-O-CH(CH₃)-C(O)-O-pentyl) | KG 158 | KG 804 | KG 170 |
| (1-methylimidazolium-N-CH₂-C(O)-O-CH(CH₃)-C(O)-O-CH₂CH₂-O-ethyl) | KG 160 | KG 805 | KG 172 |
| (1-methylimidazolium-N-CH₂-C(O)-O-CH(CH₃)-C(O)-OCH₃) | KG 151 | KG 806 | KG 163 |
| (1-methylimidazolium-N-CH₂-C(O)-O-CH(CH₃)-C(O)-O-ethyl) | KG 153 | KG 807 | KG 165 |
| (1-methylimidazolium-N-CH₂-C(O)-O-CH(CH₃)-C(O)-O-propyl) | KG 155 | KG 808 | KG 167 |
| (1-methylimidazolium-N-CH₂-C(O)-O-CH(CH₃)-C(O)-O-butyl) | KG 157 | KG 809 | KG 169 |
| (1-methylimidazolium-N-CH₂-C(O)-O-CH(CH₃)-C(O)-O-pentyl) | KG 159 | KG 810 | KG 171 |

TABLE P-continued

Library of 118 Chiral salts prepared

| Structure | | | |
|---|---|---|---|
| 1-methylimidazolium with CH(CH₃)-O-C(O)- linked to lactate 2-ethoxyethyl ester | KG 161 | KG 811 | KG 173 |
| 1-methylimidazolium with CH(CH₃)-O-C(O)- methyl lactate, ⁻NTf₂ | KG 2017 | KG 2016 | — |
| 1-methylimidazolium with phenyl-CH(OC(O)CH₂-)-C(O)OCH₃ | KG 89 | KG 92 | KG 86 |
| 1-methylimidazolium with phenyl-CH(OC(O)CH₂-)-C(O)O-ethyl | KG 812 | KG 813 | KG 307 |
| 1-methylimidazolium with phenyl-CH(OC(O)CH₂-)-C(O)O-butyl | KG 814 | KG 815 | KG 308 |
| 1-methylimidazolium with phenyl-CH(OC(O)CH₂-)-C(O)O-pentyl | KG 816 | KG 817 | KG 304 |
| 1-methylimidazolium with phenyl-CH(OC(O)CH₂-)-C(O)O-2-ethoxyethyl | KG 818 | KG 819 | KG 400 |

TABLE P-continued
Library of 118 Chiral salts prepared
| Structure | | | |
|---|---|---|---|
| 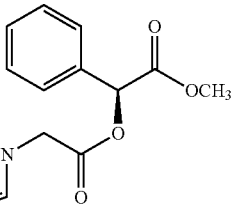 | KG 91 | KG 94 | KG 88 |
| 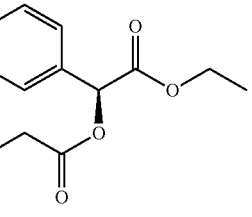 | KG 820 | KG 821 | KG 300 |
| 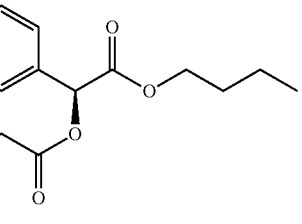 | KG 822 | KG 823 | KG 306 |
| 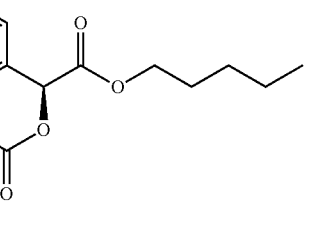 | KG 824 | KG 825 | KG 302 |
| 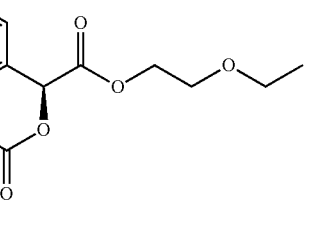 | KG 826 | KG 827 | KG 305 |
| 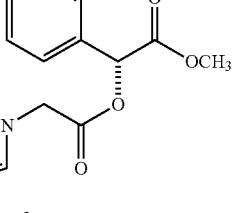 | KG 90 | KG 93 | KG 87 |
| 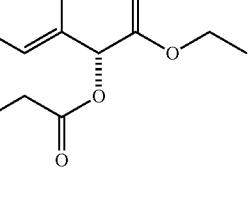 | KG 828 | KG 829 | KG 401 |

TABLE P-continued

Library of 118 Chiral salts prepared

| Structure | | | |
|---|---|---|---|
| phenyl-CH(COO-butyl)-O-C(O)-CH2-N(+)(methylimidazolium) | KG 830 | KG 831 | KG 832 |
| phenyl-CH(COO-pentyl)-O-C(O)-CH2-N(+)(methylimidazolium) | KG 833 | KG 834 | KG 303 |
| phenyl-CH(COO-CH2CH2-O-ethyl)-O-C(O)-CH2-N(+)(methylimidazolium) | KG 835 | KG 836 | KG 301 |
| methylenedioxyphenyl-CH(COOCH3)-O-C(O)-CH2-N(+)(methylimidazolium) | KG 2011 | (—) | (—) |
| methylenedioxyphenyl-CH(COO-butyl)-O-C(O)-CH2-N(+)(methylimidazolium) | KG 1022 | KG 1029 | KG 1026 |
| methylenedioxyphenyl-CH(COO-butyl)-O-C(O)-CH2-N(+)(butylimidazolium) | KG 1027 | KG 1037 | KG 1038 |
| 4-bromophenyl-CH(COOCH3)-O-C(O)-CH2-N(+)(methylimidazolium) | KG 1034 | (—) | (—) |

TABLE P-continued
Library of 118 Chiral salts prepared
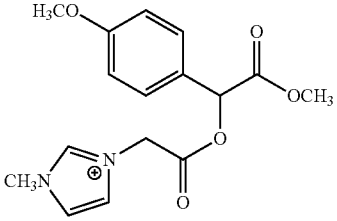
KG 1036    KG 1039    KG 1044
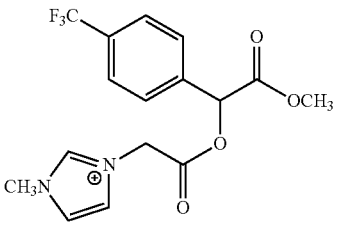
KG 1035    KG 1040    KG 1047
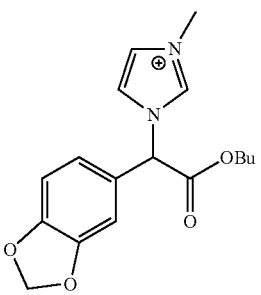
KG 1020    (−)    (−)
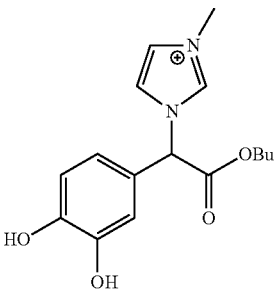
KG 1041    (−)    KG 1042
| Cation | Cl− | Ntf$_2^-$ | OctOSO$_3^-$ |
|---|---|---|---|
| 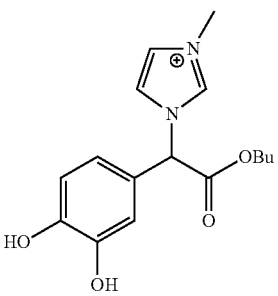 | KG 1025 | — | KG 1042 |

TABLE P-continued

Library of 118 Chiral salts prepared

| Structure | | | |
|---|---|---|---|
| (3,4-dimethoxyphenyl imidazolium methyl ester) | KG-2000 | KG-2002 | KG-2001 |
| (3,4-dimethoxyphenyl imidazolium butyl ester) | KG-2003 | KG-2005 | KG-2004 |
| (methylenedioxyphenyl imidazolium methyl ester) | KG-2006 | KG-2008 | KG-2007 |
| (3,4-dihydroxyphenyl imidazolium methyl ester) | KG 2012 | — | — |

| Ionic Liquid | Br⁻ | NTf₂⁻ | OctOSO₃⁻ |
|---|---|---|---|
| (pyridinium structure) | KG 1043 | KG 1046 | KG 1045 |

TABLE P-continued

Library of 118 Chiral salts prepared

| | | | |
|---|---|---|---|
| 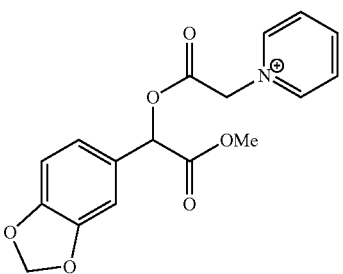 [SMILES: COC(=O)C(OC(=O)C[n+]1ccccc1)c1ccc2c(c1)OCO2] | KG 2016 | (−) | (−) |
| 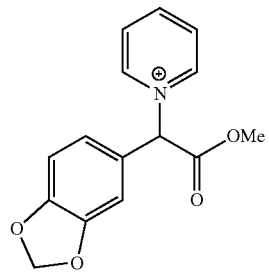 [SMILES: COC(=O)C(c1ccc2c(c1)OCO2)[n+]1ccccc1] | KG 2015 | (−) | (−) |

| Ionic Liquid | Cl⁻ | NTf₂⁻ | OctOSO₃⁻ |
|---|---|---|---|
| 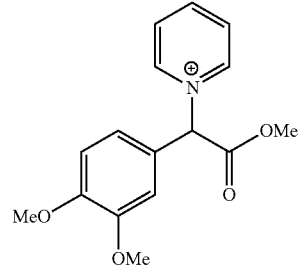 [SMILES: COC(=O)C(c1ccc(OC)c(OC)c1)[n+]1ccccc1] | KG 2013 | — | KG 2014 |

REFERENCES

N. Gathergood and P. J. Scammells, Aust. J. Chem., 2002, 55, 557

N. Gathergood, M. T. Garcia and P. J. Scammells, Green Chemistry, 2004, 6, 166

M. T. Garcia, N. Gathergood and P. J. Scammells, Green Chemistry, 2004, 7, 9

N. Gathergood, P. J. Scammells and M. T. Garcia, Green Chemistry, 2006, 8, 156

S. Bouquillon, T. Courant, D. Dean, N. Gathergood, S. Morrissey, B. Pegot, P. J. Scammells and R. Singer, Aust. J. Chem., 2007, 60, 843

Saibh Morrissey, Ian Beadham and Nicholas Gathergood, Green Chem., 2009, 11, 466-474

Xuewei Chen, a Xuehui Li, b,* Aixi Hua,* and Furong Wangb Tetrahedron: Asymmetry Volume 19, Issue 1, 30 Jan. 2008, Pages 1-14

Seebach, D.; Oei, H. A. Angew Chem Int Ed Engl 1975, 14, 634

Hüttenhain, S. H. Synth. Commun 37; 7, 1141-1146

Earle M J, McCormac P B & Seddon K R (1999) Diels-Alder reactions in ionic liquids—A safe recyclable alternative to lithium perchlorate-diethyl ether mixtures. Green Chemistry 1(1): 23 Andrew West (Chemistry World, March 2005, p 11

Suqin Hu, Tao Jiang, Zhaofu Zhang, Anlian Zhu, Buxing Han,* Jinliang Song, Ye Xie and Wenjing Li Tetrahedron Letters 48 (2007) 5613-5617

Pegot B, Vo-Thanh G, Gori D & Loupy A (2004) First application of chiral ionic liquids in asymmetric Baylis-Hillman reaction. Tetrahedron Letters 45(34): 6425

Howarth et al. (Tetrahedron Letts. 1997, 17, 3097-3100

Matos et al (Tetrahedron Letters, 49 (2008) 1652-1655

Prechtl M H, Scariot M, Scholten J D, Machado G, Teixeira S R, Dupont J., Inorg Chem. 2008 Oct. 6; 47(19):8995-9001

D. P. Curran, Journal of Fluorine Chemistry, Volume 129, Issue 10, October 2008, Pages 898-902

Veejendra K. Yadav* and K. Ganesh Babu, J. Org. Chem. 2004, 69, 577-580

M. Kawashima, T. Sato and T. Fujisawa, Tetrahedron, 1989, 45, 403

G. H. Song, Y. Q. Cai, Y. Q. Peng, J. Comb. Chem. 2005, 7, 56)

Ming Lei, Xiao-Le Tao, and Yan-Guang Wang, Helvetica Chimica Acta—Vol. 89 (2006)

Emmanuel Basle, Mickael Jean, Nicolas Gouault, Jacques Renault* and Philippe Uriac, Tetrahedron Letters 48 (2007) 8138-8140

Luo et al. Chem. J. Asian, 2009, 4, 1184-1195

Alfonso et al. Chem. Commun. 2006, 2371-2372

Felix Spindler, Christophe Malan, Matthias Lotz, Martin Kesselgruber, Ulrich Pittelkow, Andreas Rivas-Nass, Oliver Brielb and Hans-Ulrich Blaser, Tetrahedron: Asymmetry 15 (2004) 2299-2306

The invention claimed is:

1. A compound having general formula VII (VII)

wherein $R^1$ is a $C_1$-$C_4$ alkyl;
$R^2$ is —H or a $C_1$-$C_4$ alkyl;
R' is selected from the group consisting of —H and a $C_1$-$C_6$ alkyl, wherein the $C_1$-$C_6$ alkyl group may be branched or unbranched;
$R^3$ is a $C_1$-$C_6$ alkyl or a $C_1$-$C_6$ alkyl ether group, either the $C_1$-$C_6$ alkyl or the $C_1$-$C_6$ alkyl ether group may be branched or unbranched, and the alkyl ether group has at least one ether linkage in the alkyl chain; and
$R^4$, $R^5$, $R^6$, $R^7$, and $R^8$ are each independently selected from the group consisting of —H, hydroxy, $C_1$-$C_6$ alkyl, $C_1$-$C_6$ alkoxy, nitro, halo, acyl, phosphine ($PR_2$), diarylphosphine ($PAr_2$), phosphate, phosphite, sulfate, sulfite, phosphonamide, phosphinamide, sulfonamide, sulfonimide, sulfinamide, sulfinimide, carboxylic ester, carbonate, and carbamate, or two adjacent substitutions together form a $C_1$-$C_4$ alkylenedioxy ring; and
A is $OctOSO_3$, $NTf_2$ or $N(CN)_2$.

2. A compound according to claim 1 having general formula IX (IX)

wherein $R^1$ is a $C_1$-$C_4$ alkyl;
$R^2$ is —H or a $C_1$-$C_4$ alkyl;
R' is selected from the group consisting of —H and a $C_1$-$C_6$ alkyl, wherein the $C_1$-$C_6$ alkyl group may be branched or unbranched;
$R^3$ is a $C_1$-$C_6$ alkyl or a $C_1$-$C_6$ alkyl ether group, either the $C_1$-$C_6$ alkyl or the $C_1$-$C_6$ alkyl ether group may be branched or unbranched, and the alkyl ether group has at least one ether linkage in the alkyl chain; and
$R^4$ and $R^5$ are independently selected from the group consisting of —H, hydroxy, $C_1$-$C_6$ alkyl, $C_1$-$C_6$ alkoxy, nitro, halo, acyl, phosphine ($PR_2$), diarylphosphine ($PAr_2$), phosphate, phosphite, sulfate, sulfite, phosphonamide, phosphinamide, sulfonamide, sulfonimide, sulfinamide, sulfinimide, carboxylic ester, carbonate, and carbamate, or two adjacent substitutions together form a $C_1$-$C_4$ alkylenedioxy ring.

3. A compound according to claim 1 wherein R' is —H.

4. A compound according to claim 2 having general formula IX (IX)

wherein $R^1$ is a $C_1$-$C_4$ alkyl;
$R^2$ is —H or a $C_1$-$C_4$ alkyl;
$R^4$ and $R^5$ are independently selected from the group consisting of —H, a $C_1$-$C_6$ alkyl, and a $C_1$-$C_6$ alkoxy, or together form a methylenedioxy ring;
$R^3$ is a $C_1$-$C_6$ alkyl; and
A is $OctOSO_3$ or $NTf_2$.

5. A compound having general formula VII (VII)

wherein $R^1$ is a $C_1$-$C_4$ alkyl;
$R^2$ is —H or a $C_1$-$C_4$ alkyl;
R' is selected from the group consisting of —H and a $C_1$-$C_6$ alkyl, wherein the $C_1$-$C_6$ alkyl group may be branched or unbranched;
$R^3$ is a $C_1$-$C_6$ alkyl or a $C_1$-$C_6$ alkyl ether group, wherein the $C_1$-$C_6$ alkyl or the $C_1$-$C_6$ alkyl ether group may be branched or unbranched, and the alkyl ether group has at least one ether linkage in the alkyl chain; and
$R^4$, $R^5$, $R^6$, $R^7$, and $R^8$ are each independently selected from the group consisting of —H, hydroxy, $C_1$-$C_6$ alkyl, $C_1$-$C_6$ alkoxy, nitro, halo, acyl, phosphine ($PR_2$), diarylphosphine ($PAr_2$), phosphate, phosphite, sulfate, sulfite, phosphonamide, phosphinamide, sulfonamide, sulfonimide, sulfinamide, sulfinimide, carboxylic ester, carbonate, and carbamate, or two adjacent substitutions together form a $C_1$-$C_4$ alkylenedioxy ring; and
A is a counter anion.

6. A compound according to claim 2 wherein R' is —H.

7. A compound according to claim 5 selected from the group consisting of:
KG 86 RS-3-methyl-1-[1-(methoxycarbonyl)-1-phenyl-methoxycarbonylmethyl]imidazolium octyl sulphate
KG 87 R-3-methyl-1-[1-(methoxycarbonyl)-1-phenyl-methoxycarbonylmethyl]imidazolium octyl sulphate
KG 88 S-3-methyl-1-[1-(methoxycarbonyl)-1-phenyl-methoxycarbonylmethyl]imidazolium octyl sulphate KG 89 RS-3-methyl-1-[1-(methoxycarbonyl)-1-phenyl-methoxycarbonylmethyl]imidazolium bromide
KG 90 R-3-methyl-1-[1-(methoxycarbonyl)-1-phenyl-methoxycarbonylmethyl]imidazolium bromide
KG 91 S-3-methyl-1-[1-(methoxycarbonyl)-1-phenyl-methoxycarbonylmethyl]imidazolium bromide
KG 92 RS-3-methyl-1-[1-(methoxycarbonyl)-1-phenyl-methoxycarbonylmethyl]imidazolium bis(trifluoromethanesulphonyl)imide
KG 93 R-3-methyl-1-[1-(methoxycarbonyl)-1-phenyl-methoxycarbonylmethyl]imidazolium bis(trifluoromethanesulphonyl)imide
KG 94 S-3-methyl-1-[1-(methoxycarbonyl)-1-phenyl-methoxycarbonylmethyl]imidazolium bis(trifluoromethanesulphonyl)imide
KG 300 S-3-methyl-1-[1-(ethoxycarbonyl)-1-phenyl-methoxycarbonylmethyl]imidazolium octyl sulphate
KG 301 R-3-methyl-1-[1-(ethoxyethoxycarbonyl)-1-phenylmethoxycarbonylmethyl]imidazolium octyl sulphate
KG 302 S-3-methyl-1-[1-(pentoxycarbonyl)-1-phenyl-methoxycarbonylmethyl]imidazolium octyl sulphate
KG 303 R-3-methyl-1-[1-(pentoxycarbonyl)-1-phenyl-methoxycarbonylmethyl]imidazolium octyl sulphate
KG 304 RS-3-methyl-1-[1-(pentoxycarbonyl)-1-phenyl-methoxycarbonylmethyl]imidazolium octyl sulphate
KG 305 S-3-methyl-1-[1-(ethoxyethoxycarbonyl)-1-phenylmethoxycarbonylmethyl]imidazolium octyl sulphate
KG 306 S-3-methyl-1-[1-(butoxycarbonyl)-1-phenyl-methoxycarbonylmethyl]imidazolium octyl sulphate
KG 307 RS-3-methyl-1-[1-(ethoxycarbonyl)-1-phenyl-methoxycarbonylmethyl]imidazolium octyl sulphate
KG 308 RS-3-methyl-1-[1-(butoxycarbonyl)-1-phenyl-methoxycarbonylmethyl]imidazolium octyl sulphate
KG 400 RS-3-methyl-1-[1-(ethoxyethoxycarbonyl)-1-phenylmethoxycarbonylmethyl]imidazolium octyl sulphate
KG 401 R-3-methyl-1-[1-(ethoxycarbonyl)-1-phenyl-methoxycarbonylmethyl]imidazolium octyl sulphate
KG 812 RS-3-methyl-1-[1-(ethoxycarbonyl)-1-phenyl-methoxycarbonylmethyl]imidazolium bromide
KG 813 RS-3-methyl-1-[1-(ethoxycarbonyl)-1-phenyl-methoxycarbonylmethyl]imidazolium bis(trifluoromethanesulphonyl)imide
KG 814 RS-3-methyl-1-[1-(butoxycarbonyl)-1-phenyl-methoxycarbonylmethyl]imidazolium bromide
KG 815 RS-3-methyl-1-[1-(butoxycarbonyl)-1-phenyl-methoxycarbonylmethyl]imidazolium bis(trifluoromethanesulphonyl)imide
KG 816 RS-3-methyl-1-[1-(pentoxycarbonyl)-1-phenyl-methoxycarbonylmethyl]imidazolium bromide
KG 817 RS-3-methyl-1-[1-(pentoxycarbonyl)-1-phenyl-methoxycarbonylmethyl]imidazolium bis(trifluoromethanesulphonyl)imide
KG 818 RS-3-methyl-1-[1-(ethoxyethoxycarbonyl)-1-phenylmethoxycarbonylmethyl]imidazolium bromide
KG 819 RS-3-methyl-1-[1-(ethoxyethoxycarbonyl)-1-phenylmethoxycarbonylmethyl]imidazolium bis(trifluoromethanesulphonyl)imide
KG 820 S-3-methyl-1-[1-(ethoxycarbonyl)-1-phenyl-methoxycarbonylmethyl]imidazolium bromide
KG 821 S-3-methyl-1-[1-(ethoxycarbonyl)-1-phenyl-methoxycarbonylmethyl]imidazolium bis(trifluoromethanesulphonyl)imide
KG 822 S-3-methyl-1-[1-(butoxycarbonyl)-1-phenyl-methoxycarbonylmethyl]imidazolium bromide
KG 823 S-3-methyl-1-[1-(butoxycarbonyl)-1-phenyl-methoxycarbonylmethyl]imidazolium bis(trifluoromethanesulphonyl)imide
KG 824 S-3-methyl-1-[1-(pentoxycarbonyl)-1-phenyl-methoxycarbonylmethyl]imidazolium bromide
KG 825 S-3-methyl-1-[1-(pentoxycarbonyl)-1-phenyl-methoxycarbonylmethyl]imidazolium bis(trifluoromethanesulphonyl)imide
KG 826 S-3-methyl-1-[1-(ethoxyethoxycarbonyl)-1-phenylmethoxycarbonylmethyl]imidazolium bromide
KG 827 S-3-methyl-1-[1-(ethoxyethoxycarbonyl)-1-phenylmethoxycarbonylmethyl]imidazolium bis(trifluoromethanesulphonyl)imide
KG 828 R-3-methyl-1-[1-(ethoxycarbonyl)-1-phenyl-methoxycarbonylmethyl]imidazolium bromide
KG 829 R-3-methyl-1-[1-(ethoxycarbonyl)-1-phenyl-methoxycarbonylmethyl]imidazolium bis(trifluoromethanesulphonyl)imide
KG 830 R-3-methyl-1-[1-(butoxycarbonyl)-1-phenyl-methoxycarbonylmethyl]imidazolium bromide
KG 831 R-3-methyl-1-[1-(butoxycarbonyl)-1-phenyl-methoxycarbonylmethyl]imidazolium bis(trifluoromethanesulphonyl)imide
KG 832 R-3-methyl-1-[1-(butoxycarbonyl)-1-phenyl-methoxycarbonylmethyl]imidazolium octyl sulphate
KG 833 R-3-methyl-1-[1-(pentoxycarbonyl)-1-phenyl-methoxycarbonylmethyl]imidazolium bromide
KG 834 R-3-methyl-1-[1-(pentoxycarbonyl)-1-phenyl-methoxycarbonylmethyl]imidazolium bis(trifluoromethanesulphonyl)imide
KG 835 R-3-methyl-1-[1-(ethoxyethoxycarbonyl)-1-phenylmethoxycarbonylmethyl]imidazolium bromide
KG 836 R-3-methyl-1-[1-(ethoxyethoxycarbonyl)-1-phenylmethoxycarbonylmethyl]imidazolium bis(trifluoromethanesulphonyl)imide
KG 1022 RS-3-methyl-1-[1-(butoxycarbonyl)-1-(3,4-methylenedioxyphenyl)methoxycarbonylmethyl]imidazolium bromide
KG 1026 RS-3-methyl-1-[1-(butoxycarbonyl)-1-(3,4-methylenedioxyphenyl)methoxycarbonylmethyl]imidazolium octyl sulphate
KG 1027 RS-3-butyl-1-[1-(butoxycarbonyl)-1-(3,4-methylenedioxyphenyl)methoxycarbonylmethyl]imidazolium bromide
KG 1029 RS-3-methyl-1-[1-(butoxycarbonyl)-1-(3,4-methylenedioxyphenyl)methoxycarbonylmethyl]imidazolium bis(trifluoromethanesulphonyl)imide
KG 1034 RS-3-methyl-1-[1-(methoxycarbonyl)-1-(4-bromophenyl)methoxycarbonylmethyl]imidazolium bromide
KG 1035 RS-3-methyl-1-[1-(methoxycarbonyl)-1-(4-trifluoromethylphenyl)methoxycarbonylmethyl]imidazolium bromide
KG 1036 RS-3-methyl-1-[1-(methoxycarbonyl)-1-(4-methoxyphenyl)methoxycarbonylmethyl]imidazolium bromide
KG 1037 RS-3-butyl-1-[1-(butoxycarbonyl)-1-(3,4-methylenedioxyphenyl)methoxycarbonylmethyl]imidazolium bis(trifluoromethanesulphonyl)imide
KG 1038 RS-3-butyl-1-[1-(butoxycarbonyl)-1-(3,4-methylenedioxyphenyl)methoxycarbonylmethyl]imidazolium octyl sulphate
KG 1039 RS-3-methyl-1-[1-(methoxycarbonyl)-1-(4-methoxyphenyl)methoxycarbonylmethyl]imidazolium bis(trifluoromethanesulphonyl)imide KG 1040 RS-3-methyl-1-[1-(methoxycarbonyl)-1-(4-trifluoromethylphenyl)methoxycarbonylmethyl]imidazolium bis(trifluoromethanesulphonyl)imide KG 1044 RS-3-methyl-1-[1-(methoxycarbonyl)-1-(4-methoxyphenyl)methoxycarbonylmethyl]imidazolium octyl sulphate KG 1047 RS-3-methyl-1-[1-(methoxycarbonyl)-1-(4-trifluoromethylphenyl)methoxycarbonylmethyl]imidazolium octyl sulphate and KG 2011 RS-3-methyl-1-[1-(methoxycarbonyl)-1-(3,4-methylenedioxyphenyl)methoxycarbonylmethyl]imidazolium chloride.

* * * * *